(12) United States Patent
Herault et al.

(10) Patent No.: US 9,493,836 B2
(45) Date of Patent: Nov. 15, 2016

(54) METHOD FOR DIAGNOSING HEMATOLOGICAL DISORDERS

(75) Inventors: Olivier Herault, Veigne (FR); Christine Vignon, Chambray-les-Tours (FR)

(73) Assignee: UNIVERSITE FRANCOIS RABELAIS DE TOURS, Tours (FR)

( * ) Notice: Subject to any disclaimer, the term of this patent is extended or adjusted under 35 U.S.C. 154(b) by 0 days.

(21) Appl. No.: 13/997,450

(22) PCT Filed: Dec. 22, 2011

(86) PCT No.: PCT/EP2011/073757
§ 371 (c)(1),
(2), (4) Date: Jun. 24, 2013

(87) PCT Pub. No.: WO2012/085188
PCT Pub. Date: Jun. 28, 2012

(65) Prior Publication Data
US 2013/0288924 A1    Oct. 31, 2013

(30) Foreign Application Priority Data

Dec. 22, 2010 (EP) .................................. 10306483

(51) Int. Cl.
*C12Q 1/68* (2006.01)
*C07H 21/04* (2006.01)

(52) U.S. Cl.
CPC ........... *C12Q 1/6883* (2013.01); *C12Q 1/6886* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 5,990,299 | A | * 11/1999 | Ruzdijic | C12N 15/1138 536/23.1 |
| 2001/0051344 | A1 | * 12/2001 | Shalon | B01L 3/0244 435/6.11 |
| 2007/0154931 | A1 | 7/2007 | Radich et al. | |

FOREIGN PATENT DOCUMENTS

| | | |
|---|---|---|
| EP | 1947194 A1 | 7/2008 |
| WO | 2005080601 A2 | 9/2005 |
| WO | 2006125195 A2 | 11/2006 |
| WO | WO2006125195 | * 11/2006 |

OTHER PUBLICATIONS

Mills et al. Blood. 2009;114:1063-1072.*
Michiels (The Lancet 2005 vol. 365 pp. 488-492).*
Whitehead (Genome Biology 2005 vol. 6 Issue 2 Article R13).*
Hoshikawa et al (Physical Genomics 2003 vol. 12 pp. 209-219).*
Cheung (Nature Genetics 2003 vol. 33 pp. 422-425).*
Economopoulou et al., "Cell cycle and apoptosis regulatory gene expression in the bone marrow of patients with de novo myelodysplastic syndromes (MDS)", Ann Hematol, 2010, vol. 89, pp. 349-358, XP002636031.
Mills et al., "Microarray-based classifiers and prognosis models identify subgroups with distinct clinical outcomes and high risk of AML transformation of myelodysplastic syndrome", Blood, 2009, vol. 114, No. 5, pp. 1063-1072, XP002636030.
Miyazato et al., "Identification of myelodysplastic syndrome-specific genes by DNA microarray analysis with purified hematopoietic stem cell fraction", Blood, 2001, vol. 98, No. 2, pp. 422-427, XP-002952629.
Pellagatti et al., "Gene expression profiles of CD34+ cells in myelodysplastic syndromes: involvement of interferon-stimulated genes and correlation to FAB subtype and karyotype", Blood, 2006, vol. 108, No. 1, pp. 337-345.
Roela et al., "Gene stage-specific expression in the microenvironment of pediatric myelodysplastic syndromes", Leukemia Research, 2007, vol. 31, pp. 579-589.
Theilgaard-Monch et al., "Gene expression profiling in MDS and AML: potential and future avenues", Leukemia, 2011, vol. 25, pp. 909-920.
International Search Report, dated Mar. 6, 2012, from corresponding PCT application.

* cited by examiner

*Primary Examiner* — Amanda Haney
(74) *Attorney, Agent, or Firm* — Young & Thompson

(57) ABSTRACT

Disclosed is a method for the diagnosis, and/or the classification, of a hematological disorder, including the steps of: a). measuring, the expression level of at least the genes of a sub-group of 6 genes, b). comparing the expression level of each genes measured in step a)., with the expression level of the same genes in healthy control sample, and c). determining the status of the biological sample.

7 Claims, 8 Drawing Sheets

Fig. 5A
Fig. 5B
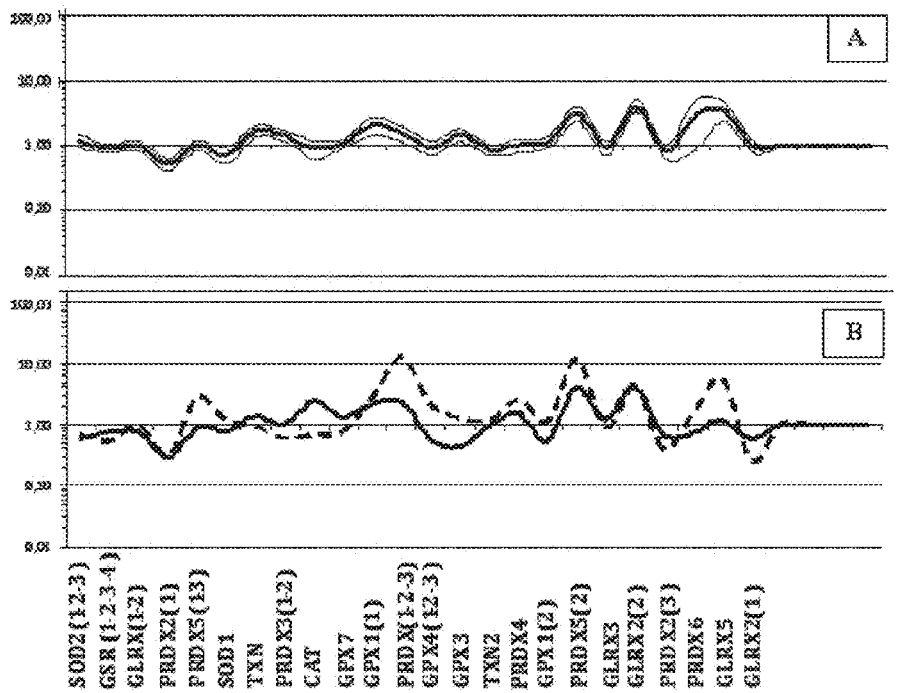
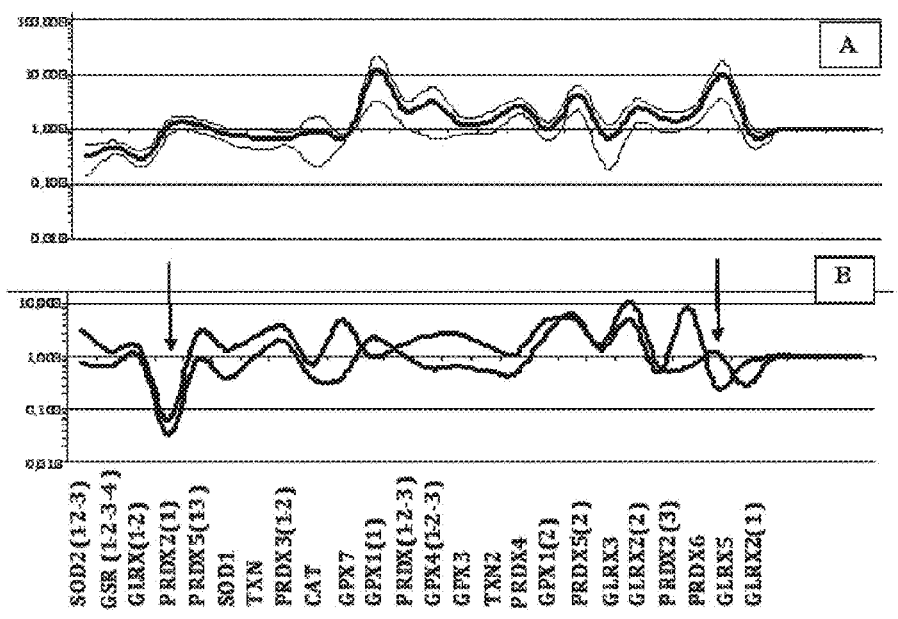
Fig. 6

SEQUENCE LISTING

<160> NUMBER OF SEQ ID NOS: 85

<210> SEQ ID NO 1
<211> LENGTH: 1779
<212> TYPE: DNA
<213> ORGANISM: Homo sapiens

<400> SEQUENCE: 1

```
gtcgcccgg gacggggagg tggggagctg agggcaagtc gcgcccgccc ctgaaatccc      60
agccgcctag cgattggctg caagggtctc ggcttggccg cggattggtc acacccgagg    120
gcttgaaagg tggctgggag cgccggacac ctcagacgga cggtggccag ggatcaggca    180
gcggctcagg cgaccctgag tgtgccccca ccccgccatg gcccggctgc tgcaggcgtc    240
ctgcctgctt tccctgctcc tggccggctt cgtctcgcag agccggggac aagagaagtc    300
gaagatggac tgccatggtg gcataagtgg caccatttac gagtacggag ccctcaccat    360
tgatggggag gagtacatcc ccttcaagca gtatgctggc aaatacgtcc tctttgtcaa    420
cgtggccagc tactgaggcc tgacgggcca gtacattgaa ctgaatgcac tacaggaaga    480
gcttgcacca ttcggtctgg tcattctggg ctttccctgc aaccaatttg gaaaacagga    540
accaggagag aactcagaga tccttcctac cctcaagtat gtccgaccag gtggaggctt    600
tgtccctaat ttccagctct ttgagaaagg ggatgtcaat ggagagaaag agcagaaatt    660
ctacactttc ctaaagaact cctgtcctcc cacctcggag ctcctgggta catctgaccg    720
cctcttctgg gaacccatga aggttcacga catccgctgg aactttgaga agttcctggt    780
ggggccagat ggtataccca tcatgcgctg gcaccaccgg accacggtca gcaacgtcaa    840
gatggacatc ctgtcctaca tgaggcggca ggcagccctg ggggtcaaga ggaagtaact    900
gaaggccgtc tcatcccatg tccaccatgt aggggaggga ctttgttcag gaagaaatcc    960
gtgtctccaa ccacactatc tacccatcac agacccctt cctatcactc aaggcccag    1020 cctggcacaa atggatgcat acagttctgt gtactgccag gcatgtgggt gtgggtgcat   1080
gtgggtgttt acacacatgc ctacaggtat gcgtgattgt gtgtgtgtgc atgggtgtac   1140
agccacgtgt ctacctatgt gtctttctgg gaatgtgtac catctgtgtg cctgcagctg   1200
tgtagtgctg gacagtgaca acccttctc tccagttctc cactccaatg ataatagttc   1260
acttacacct aaacccaaag gaaaaaccag ctctaggtcc aattgttctg ctctaactga   1320
tacctcaacc ttggggccag catctcccac tgcctccaaa tattagtaac tatgactgac   1380 gtcccccagaa gtttctgggt ctaccacact ccccaacccc ccactcctac ttcctgaagg   1440
gccctcccaa ggctacatcc ccaccccaca gttctccctg agagagatca acctccctga   1500
gatcaaccaa ggcagatgtg acagcaaggg ccacggaccc catggcaggg gtggcgtctt   1560
catgagggag gggcccaaag cccttgtggg cggacctccc ctgagcctgt ctgaggggcc   1620
```

```
agcccttagt gcattcaggc taaggcccct gggcagggat gccaccctg ctccttcgga       1680 ggacgtgccc tcaccctca ctggtccact ggcttgagac tcaccccgtc tgcccagtaa       1740
aagcctttct gcagcagctg aaaaaaaaaa aaaaaaaa                              1779

<210> SEQ ID NO 2
<211> LENGTH: 921
<212> TYPE: DNA
<213> ORGANISM: Homo sapiens

<400> SEQUENCE: 2
cagttaaaag gaggcgcctg ctggcctccc cttacagtgc ttgttcgggg cgctccgctg         60
gcttcttgga caattgcgcc atgtgtgctg ctcggctagc ggcggcggcg gcggcggccc        120
agtcggtgta tgccttctcg gcgcgcccgc tggccggcgg ggagcctgtg agcctgggct        180
ccctgcgggg caaggtacta cttatcgaga atgtggcgtc cctctgaggc accacggtcc        240
gggactacac ccagatgaac gagctgcagc ggcgcctcgg accccggggc tggtggtgc         300 tcggcttccc gtgcaaccag tttgggcatc aggagaacgc caagaacgaa gagattctga        360
attccctcaa gtacgtccgg cctggtggtg ggttcgagcc caacttcatg ctcttcgaga        420
agtgcgaggt gaacggtgcg ggggcgcacc ctctcttcgc cttcctgcgg gaggccctgc        480
cagctcccag cgacgacgcc accgcgctta tgaccgaccc caagctcatc acctggtctc        540
cggtgtgtcg caacgatgtt gcctggaact ttgagaagtt cctggtgggc cctgacggtg        600 tgccctacg caggtacagc cgccgcttcc agaccattga catcgagcct gacatcgaag         660
ccctgctgtc tcaagggccc agctgtgcct agggcgcccc tcctacccg gctgcttggc        720 agttgcagtg ctgctgtctc gggggggttt tcatctatga gggtgtttcc tctaaaccta       780
cgagggagga acacctgatc ttacagaaaa taccacctcg atgggtgc tggtcctgtt         840 gatcccagtc tctgccagac caaggcgagt ttccccacta taaagtgcc gggtgtcagc        900 agaaaaaaaa aaaaaaaaa a                                                  921

<210> SEQ ID NO 3
<211> LENGTH: 735
<212> TYPE: DNA
<213> ORGANISM: Homo sapiens

<400> SEQUENCE: 3
gcggtgtccg gcagtagagc tcgctgcaga tccgggctct gaccatgatt tggcgccgcg         60
cggcgctggc ggggacgcgg ctggtttgga gcaggagcgg ctcggcaggc tggcttgaca        120
gggcggcggg agctgcggga gctgcggcag ctgcggcctc tgggatggag agcaatacat        180
catcatcttt ggagaattta gcgacggcgc ctgtgaacca gatccaagaa acaatttctg        240
ataattgtgt ggtgattttc tcaaaaacat cctgttctta ctgtacaatg caaaaaagc         300 ttttccatga catgaatgtt aactataaag tggtggaact ggacctgctt gaatatggaa        360
accagttcca agatgctctt tacaaaatga ctggtgaaag aactgttcca gaatatttg         420 tcaatggtac ttttattgga ggtgcaactg acactcatag gcttcacaaa gaaggaaaat        480
tgctcccact agttcatcag tgttatttaa aaaaagtaa gaggaaagaa tttcagtgat        540
gtttatacta ataagtttgc tagtacagtg tcagttattt aaagtggtaa tgcccgataa        600
tgtcttttaa atgtttgagg atgttttaaa tacatgcatt gtcttcacga agaagatgta        660
aaaataatga acaataaatt gcggtggaaa cctcaaaaaa aaaaaaaaaa aaaaaaaaa         720
```

| | |
|---|---:|
| aaaaaaaaaa aaaaa | 735 |

<210> SEQ ID NO 4
<211> LENGTH: 2300
<212> TYPE: DNA
<213> ORGANISM: Homo sapiens

<400> SEQUENCE: 4

| | |
|---|---:|
| actcggggca acaggcagat ttgcctgctg agggtggaga cccacgagcc gaggcctcct | 60 |
| gcagtgttct gcacagcaaa ccgcacgcta tggctgacag ccgggatccc gccagcgacc | 120 |
| agatgcagca ctggaaggag cagcgggccg cgcagaaagc tgatgtcctg accactggag | 180 |
| ctggtaaccc agtaggagac aaacttaatg ttattacagt agggcccgt gggccccttc | 240 |
| ttgttcagga tgtggttttc actgatgaaa tggctcattt tgaccgagag agaattcctg | 300 |
| agagagttgt gcatgctaaa ggagcagggg cctttggcta ctttgaggtc acacatgaca | 360 |
| ttaccaaata ctccaaggca aaggtatttg agcatattgg aaagaagact cccatcgcag | 420 |
| ttcggttctc cactgttgct ggagaatcgg gttcagctga cacagttcgg gaccctcgtg | 480 |
| ggtttgcagt gaaattttac acagaagatg gtaactggga tctcgttgga aataacaccc | 540 |
| ccattttctt catcagggat cccatattgt ttccatcttt tatccacagc aaaagagaa | 600 |
| atcctcagac acatctgaag gatccggaca tggtctggga cttctggagc ctacgtcctg | 660 |
| agtctctgca tcaggtttct ttcttgttca gtgatcgggg gattccagat ggacatcgcc | 720 |
| acatgaatgg atatggatca catactttca agctggttaa tgcaaatggg gaggcagttt | 780 |
| attgcaaatt ccattataag actgaccagg gcatcaaaaa cctttctgtt gaagatgcgg | 840 |
| cgagactttc ccaggaagat cctgactatg gcatccggga tcttttttaac gccattgcca | 900 |
| caggaaagta cccctcctgg acttttttaca tccaggtcat gacatttaat caggcagaaa | 960 |
| ctttttccatt taatccattc gatctcacca aggtttggcc tcacaaggac taccctctca | 1020 |
| tcccagttgg taaactggtc ttaaaccgga atccagttaa ttactttgct gaggttgaac | 1080 |
| agatagcctt cgacccaagc aacatgccac ctggcattga ggccagtcct gacaaaatgc | 1140 |
| ttcagggccg cctttttgcc tatcctgaca ctcaccgcca tcgcctggga cccaattatc | 1200 |
| ttcatatacc tgtgaactgt ccctaccgtg ctcgagtggc caactaccag cgtgacggcc | 1260 |
| cgatgtgcat gcaggacaat cagggtggtc tccaaatta ctaccccaac agctttggtg | 1320 |
| ctccggaaca acagccttct gccctggagc acagcatcca atattctgga gaagtgcgga | 1380 |
| gattcaacac tgccaatgat gataacgtta ctcaggtgcg ggcattctat gtgaacgtgc | 1440 |
| tgaatgagga acagaggaaa cgtctgtgtg agaacattgc cggccacctg aaggatgcac | 1500 |
| aaattttcat ccagaagaaa gcggtcaaga acttcactga ggtccaccct gactacggga | 1560 |
| gccacatcca ggctcttctg gacaagtaca atgctgagaa gcctaagaat gcgattcaca | 1620 |
| cctttgtgca gtccggatct cacttggcgg caagggagaa ggcaaatctg tgaggccggg | 1680 |
| gccctgcacc tgtgcagcga agcttagcgt tcatccgtgt aacccgctca tcactggatg | 1740 |
| aagattctcc tgtgctagat gtgcaaatgc aagctagtgg cttcaaaata gagaatccca | 1800 |
| cttttctatag cagattgtgt aacaatttta atgctatttc cccagggaa aatgaaggtt | 1860 |
| aggattttaac agtcatttaa aaaaaaaatt tgttttgacg gatgattgga ttattcattt | 1920 |
| aaaatgatta gaaggcaagt ttctagctag aaatatgatt ttatttgaca aaatttgttg | 1980 |
| aaattatgta tgtttacata tcacctcatg gcctattata ttaaaatatg gctataaata | 2040 |
| tataaaaaga aaagataaag atgatctact cagaaatttt tattttttcta aggttctcat | 2100 |

| aggaaaagta catttaatac agcagtgtca tcagaagata acttgagcac cgtcatggct | 2160 |
| taatgtttat tcctgataat aattgatcaa attcattttt ttcactggag ttacattaat | 2220 |
| gttaattcag cactgatttc acaacagatc aatttgtaat tgcttacatt tttacaataa | 2280 |
| ataatctgta cgtaagaaca | 2300 |

<210> SEQ ID NO 5
<211> LENGTH: 1262
<212> TYPE: DNA
<213> ORGANISM: Homo sapiens

<400> SEQUENCE: 5

| actctcgcga gatccctact ggctataaag gcagcgcccc ggagagctct tgcgcgtctt | 60 |
| gttcttgcct ggtgtcggtg gttagtttct gcgacttgtg ttgggactgg tgagtgtggg | 120 |
| cagtgcggcc cctgcggagt gaggcgcggc gcgcccttct tgcctgttgc ctcttcctcc | 180 |
| tcctgtccgg ggcccgcccg cgctcggtg ggggtgctgt gatgcgtgag gcagccgggg | 240 |
| gaggcccgga gtccgagact gcttgagcgc tgcgcacacc cctctcgtgg gcccccacg | 300 |
| taggtgcggg aacctggttg aaccccaagc tgataggaag atgtcttcag gaaatgctaa | 360 |
| aattgggcac cctgccccca acttcaaagc cacagctgtt atgccagatg gtcagtttaa | 420 |
| agatatcagc ctgtctgact acaaaggaaa atatgttgtg ttcttctttt accctcttga | 480 |
| cttcaccttt gtgtgcccca cggagatcat tgctttcagt gatagggcag aagaatttaa | 540 |
| gaaactcaac tgccaagtga ttggtgcttc tgtggattct cacttctgtc atctagcatg | 600 |
| ggtcaataca cctaagaaac aaggaggact gggacccatg aacattcctt tggtatcaga | 660 |
| cccgaagcgc accattgctc aggattatgg ggtcttaaag gctgatgaag catctcgtt | 720 |
| caggggcctt tttatcattg atgataaggg tattcttcgg cagatcactg taaatgacct | 780 |
| ccctgttggc cgctctgtgg atgagacttt gagactagtt caggccttcc agttcactga | 840 |
| caaacatggg gaagtgtgcc cagctggctg gaaacctggc agtgatacca tcaagcctga | 900 |
| tgtccaaaag agcaaagaat atttctccaa gcagaagtga gcgctgggct gttttagtgc | 960 |
| caggctgcgg tgggcagcca tgagaacaaa acctcttctg tattttttt ttccattagt | 1020 |
| aaaacacaag acttcagatt cagccgaatt gtggtgtctt acaaggcagg cctttcctac | 1080 |
| aggggtgga gagaccagcc tttcttcctt tggtaggaat ggcctgagtt ggcgttgtgg | 1140 |
| gcaggctact ggtttgtatg atgtattagt agagcaaccc attaatcttt tgtagtttgt | 1200 |
| attaaacttg aactgagacc ttgatgagtc tttaaaaaaa aaaaaaaaaa aaaaaaaaa | 1260 |
| aa | 1262 |

<210> SEQ ID NO 6
<211> LENGTH: 827
<212> TYPE: DNA
<213> ORGANISM: Homo sapiens

<400> SEQUENCE: 6

| gcagtggagg cggcccaggc ccgccttccg cagggtgtcg ccgctgtgcc gctagcggtg | 60 |
| ccccgcctgc tgcggtggca ccagccagga ggcgagtgg aagtgccgt ggggcgggta | 120 |
| tgggactagc tggcgtgtgc gccctgagac gctcagcggg ctatatactc gtcggtgggg | 180 |
| ccggcggtca gtctgcggca gcggcagcaa gacggtgcag tgaaggagag tgggcgtctg | 240 |
| gcggggtccg cagtttcagc agagccgctg cagccatggc cccaatcaag gtgggagatg | 300 |

-continued

```
ccatcccagc agtggaggtg tttgaagggg agccagggaa caaggtgaac ctggcagagc      360
tgttcaaggg caagaagggt gtgctgtttg gagttcctgg ggccttcacc cctggatgtt      420
ccaaggttcg gctcctggct gatcccactg gggcctttgg gaaggagaca gacttattac      480
tagatgattc gctggtgtcc atctttggga atcgacgtct caagaggttc tccatggtgg      540
tacaggatgg catagtgaag gccctgaatg tggaaccaga tggcacaggc ctcacctgca      600
gcctggcacc caatatcatc tcacagctct gaggccctgg gccagattac ttcctccacc      660
cctccctatc tcacctgccc agccctgtgc tggggccctg caattggaat gttggccaga      720
tttctgcaat aaacacttgt ggtttgcggc caaaaaaaaa aaaaaaaaaa aaaaaaaaaa      780
aaaaaaaaaa aaaaaaaaaa aaaaaaaaaa aaaaaaaaaa aaaaaa                    827
```

<210> SEQ ID NO 7
<211> LENGTH: 1593
<212> TYPE: DNA
<213> ORGANISM: Homo sapiens

<400> SEQUENCE: 7

```
gcggtgccct tgcggcgcag ctggggtcgc ggccctgctc cccgcgcttt cttaaggccc       60
gcgggcggcg caggagcggc actcgtggct gtggtggctt cggcagcggc ttcagcagat      120
cggcggcatc agcggtagca ccagcactag cagcatgttg agccgggcag tgtgcggcac      180
cagcaggcag ctggctccgg ttttggggta tctgggctcc aggcagaagc acagcctccc      240
cgacctgccc tacgactacg gcgccctgga acctcacatc aacgcgcaga tcatgcagct      300
gcaccacagc aagcaccacg cggcctacgt gaacaacctg aacgtcaccg aggagaagta      360
ccaggaggcg ttggccaagg gagatgttac agcccagata gctcttcagc ctgcactgaa      420
gttcaatggt ggtggtcata tcaatcatag cattttctgg acaaacctca gccctaacgg      480
tggtggagaa cccaaagggg agttgctgga agccatcaaa cgtgactttg ttcctttga      540 caagtttaag gagaagctga cggctgcatc tgttggtgtc caaggctcag gttgggttg      600 gcttggtttc aataaggaac ggggacactt acaaattgct gcttgtccaa atcaggatcc      660
actgcaagga acaacaggcc ttattccact gctggggatt gatgtgtggg agcacgctta      720
ctaccttcag tataaaaatg tcaggcctga ttatctaaaa gctatttgga atgtaatcaa      780
ctgggagaat gtaactgaaa gatacatggc ttgcaaaaag taaaccacga tcgttatgct      840
gagtatgtta agctctttat gactgttttt gtagtggtat agagtactgc agaatacagt      900
aagctgctct attgtagcat tcttgatgt tgcttagtca cttatttcat aaacaactta      960
atgttctgaa taatttctta ctaaacattt tgttattggg caagtgattg aaaatagtaa     1020
atgctttgtg tgattgaatc tgattggaca ttttcttcag agagctaaat tacaattgtc     1080
atttataaaa ccatcaaaaa tattccatcc atatactttg gggacttgta gggatgcctt     1140
tctagtccta ttctattgca gttatagaaa atcagtctt tgccccagt tacttaaaaa     1200 taaaatatta acactttccc aagggaaaca ctcggctttc tatagaaaat tgcacttttt     1260
gtcgagtaat cctctgcagt gatacttctg gtagatgtca cccagtggtt tttgttaggt     1320
caaatgttcc tgtatagttt ttgcaaatag agctgtatac tgtttaaatg tagcaggtga     1380
actgaactgg ggtttgctca cctgcacagt aaaggcaaac ttcaacagca aaactgcaaa     1440
aaggtggttt ttgcagtagg agaaaggagg atgtttattt gcagggcgcc aagcaaggag     1500
aattgggcag ctcatgcttg agacccaatc tccatgatga cctacaagct agagtattta     1560
aaggcagtgg taaatttcag gaaagcagaa gtt                                 1593
```

<210> SEQ ID NO 8
<211> LENGTH: 3174
<212> TYPE: DNA
<213> ORGANISM: Homo sapiens

<400> SEQUENCE: 8

```
tcctcctggg tcttgcctag cggcgggcgc atgcttagtc accgtgaggc tgcgcttgcc      60
cggggcccgc gccccctac cccggggacc gccccgggc cgcccgcccc acttggcgcg       120
ccacttccgc gtgcatggcc ctgctgcccc gagccctgag cgccggcgcg ggaccgagct     180
ggcggcgggg ggcgcgcgcc ttccgaggct tcctgctgct tctgcccgag cccgcggccc     240
tcacgcgcgc cctctcccgt gccatggcct gcaggcagga gccgcagccg cagggcccgc    300
cgcccgctgc tggcgccgtg gcctcctatg actacctggt gatcggggc ggctcgggcg     360
ggctggccag cgcgcgcagg gcggccgagc tgggtgccag ggccgccgtg gtggagagcc   420
acaagctggg tggcacttgc gtgaatgttg atgtgtacc caaaaaggta atgtggaaca    480
cagctgtcca ctctgaattc atgcatgatc atgctgatta tggctttcca agttgtgagg    540
gtaaattcaa ttggcgtgtt attaaggaaa agcgggatgc ctatgtgagc cgcctgaatg   600
ccatctatca aaacaatctc accaagtccc atatagaaat catccgtggc catgcagcct   660
tcacgagtga tcccaagccc acaatagagg tcagtgggaa aaagtacacc gccccacaca    720
tcctgatcgc cacaggtggt atgccctcca cccctcatga gagccagatc cccggtgcca   780
gcttaggaat aaccagcgat ggattttttc agctggaaga attgcccggc cgcagcgtca   840
ttgttggtgc aggttacatt gctgtggaga tggcagggat cctgtcagcc ctgggttcta   900
agacatcact gatgatacgg catgataagg tacttagaag ttttgattca atgatcagca   960
ccaactgcac ggaggagctg gagaacgctg gcgtggaggt gctgaagttc tcccaggtca  1020
aggaggttaa aaagactttg tcgggcttgg aagtcagcat ggttactgca gttcccggta  1080
ggctaccagt catgaccatg attccagatg ttgactgcct gctctgggcc attgggcggg  1140
tcccgaatac caaggacctg agtttaaaca aactggggat tcaaaccgat gacaagggtc  1200
atatcatcgt agacgaattc cagaatacca acgtcaaagg catctatgca gttggggatg  1260
tatgtgaaaa agctcttctt actccagttg caatagctgc tggccgaaaa cttgcccatc  1320
gacttttga atataaggaa gattccaaat tagattataa caacatccca actgtggtct  1380
tcagccaccc ccctattggg acagtgggac tcacggaaga tgaagccatt cataaatatg   1440
gaatagaaaa tgtgaagacc tattcaacga gctttacccc gatgtatcac gcagttacca   1500
aaaggaaaac aaaatgtgtg atgaaaatgg tctgtgctaa caaggaagaa aaggtggttg   1560
ggatccatat gcagggactt gggtgtgatg aaatgctgca gggttttgct gttgcagtga   1620
agatgggagc aacgaaggca gactttgaca cacagtcgc cattcaccct acctcttcag   1680
aagagctggt cacacttcgt tgagaaccag gagacacgtg tggcgggcag tgggacccat  1740
agatcttctg aaatgaaaca ataatcaca ttgacttact gtttgagttt tatgtatttc    1800
tttattttaa tcaggatctt ctgatagtgg aaattttag tacataatag aacttattta   1860
tggagttaga aatttgtagt gttatccagg attgattttc atttgatcac atctcacagt   1920
aattaatatt ttcaagtttt tttttattta acagctctgt gctagttttt tttttctgtt    1980
ttagcctcat cccaaatata aagctttgtg aagtacaatt aacttaatgt acttgaatga  2040
atagaacttg ctactttttt ttttttttt tttgagacag agttttgctc tcattgccca    2100
```

| | |
|---|---|
| ggctggagtg cggtggtgct atttcagctc accacaacct ctgcctcctg ggttcaagtg | 2160 |
| attctcctgc cttagcctcc cgaatagctg gaattacagg cacgcaccac catgcctgac | 2220 |
| taattttgta ttttagtag acatgggtt tctccatgtt ggtcaggctg gtctcaaact | 2280 |
| cccaccttca ggtgatccgc ccacctcggc ctcctgaggt gctgagatta caggcgtgag | 2340 |
| ccactgtgcc agcttgctaa ttttcacaga agttgatggc aattcttcac atgtaaacag | 2400 |
| tgccagtgca cagaaccttt atatattttt tgaagccagt actgtgctct gcatataaca | 2460 |
| aagctgcttc aaggatgaga ccttttctta aaagcatgta atgtgagaag ccggcctgcc | 2520 |
| ttatttctt ttttctttt taatgattaa aaatagtttg tggcaaggca cggtggctca | 2580 |
| ggcctgtaat tctagcactt tgggaggccg aggcaggagg attacttgag cctacaagtt | 2640 |
| tgaggccagc atgcacagca tagcaagact gcatctctac agagagtaaa aaaaattacc | 2700 |
| cgagtgtggt gatgtgcatc tgtaatctca gctacttggg aggctgaggt gagaggatca | 2760 |
| cttgagcttg ggtgaggtga ggctgcagtg agtcctgatc atgctgctgc actcaatctt | 2820 |
| ggacaacaga gcaagaccct gtctcaaaaa aaaaaaaaa aatatatat atatatat | 2880 |
| attattttta tgaggtgaag tgcatcaaac ttgggaaaga tttgaggagg ctgggaacct | 2940 |
| cctggaaaac cactccttga agaaagatat gagagacatt tagaagtgat tcctgctttc | 3000 |
| agaaggaggt ggattcaaat acatcaaaag tcccttcctc tgctaagtgt ttatagttca | 3060 |
| atgaataatt tcaatatttg tatgtgttct tgtcatttta ttttttctg aaaaacttcc | 3120 |
| aaaaatttga aaataaaatt acagcctttt cttcttataa aaaaaaaaa aaaa | 3174 |

<210> SEQ ID NO 9
<211> LENGTH: 1661
<212> TYPE: DNA
<213> ORGANISM: Homo sapiens

<400> SEQUENCE: 9

| | |
|---|---|
| attgcattcc tgggcattgc taactagtga agtataccag atggaaatgt cttcgaagct | 60 |
| gtccctttaa aactcgagca agctaccagg caaactccgc ctccagggag gttccttatt | 120 |
| aaataggagc caactggctg ggtcggggct caataccca agcaataccct gcaactgagg | 180 |
| attcttcccg gggagaccgc agcccatcgg catggctcaa gagtttgtga actgcaaaat | 240 |
| ccagcctggg aagtggttg tgttcatcaa gcccacctgc ccgtactgca ggagggccca | 300 |
| agagatcctc agtcaattgc ccatcaaaca agggcttctg gaatttgtcg atatcacagc | 360 |
| caccaaccac actaacgaga ttcaagatta tttgcaacag ctcacgggag caagaacggt | 420 |
| gcctcgagtc tttattggta aagattgtat aggcggatgc agtgatctag tctcttttgca | 480 |
| acagagtggg gaactgctga cgcggctaaa gcagattgga gctctgcagt aaccacagaa | 540 |
| caggccccat gctgacgtcc ctcctcaaga gctggatggc attgcaaatg atgacagcac | 600 |
| ttctggtgga tgaatttggg ggcacaaaca gcttttttcc tcttttggct cagtatttaa | 660 |
| aagtggacca acttgctctt aatcacaggg ccaagaaggt tgacgggcca tcttggtttt | 720 |
| cttctggatg tgctctttgg ttttcagaag actgtgacaa gttctggccc aggattcgct | 780 |
| cactgacct caattgtcct cttttggcatg cgtttcttac tgttctccat gtgtcggcat | 840 |
| gtctctacct ctaagccagt gttttcaac tatgtttatc cagactcctt ctccacaatg | 900 |
| atgaatccac agttggttat ctgctactgc ccattagcta aaatcatttt gctgcttgac | 960 |
| tttatgagt ttgtattatg aaatcagtgg gtattttgaa tgtgttcttt ctaactacat | 1020 |
| gcatctctcc actcaactcc accccatccc atcccacctt gaaaatcact gctctgaacc | 1080 |

| | |
|---|---|
| agtgttctcc accttgtcct ccacagatct cataggaaat gttcaacaat tctgtgaaag | 1140 |
| gtcacaggac ccaattggag aaatcatatg aaaagcatag ttggtcttgg tgtcatatgg | 1200 |
| atcagaggca caagtgcaga ggctgtggtc atgcggaaca ctctgttatt taagatggct | 1260 |
| atccagataa tcctgaacac tgtgtattta ttttatttag actaccagca aagattaaag | 1320 |
| catgaaatgt aaaacatctg ataaaactta cagcccccta caccaagagt gtatctgtga | 1380 |
| aagagctcct acactttgaa aacttaagaa tcccttatca tgaagtttgc ctgttctaga | 1440 |
| attgtaagat tgttaatttc cttcaatctc tagtgacaac acttaatttc ttttctaata | 1500 |
| aaaaaaacct atagatgatt cagtgatttt tgtccaattc atttgcatgt tctcaagaca | 1560 |
| ttaaggaatg ttatgcgaaa tacactaact taaaactgtg tttatatttg gccctgccat | 1620 |
| tataaataaa gacacgtgct gctgtcaaaa aaaaaaaaa a | 1661 |

<210> SEQ ID NO 10
<211> LENGTH: 1039
<212> TYPE: DNA
<213> ORGANISM: Homo sapiens

<400> SEQUENCE: 10

| | |
|---|---|
| gctcgtccgc tccctccccc gcgccgtgca cgtcttggtt cgggccgggc ataaaaggct | 60 |
| tcgcggccca gggctcactt ggcgctgaga acgcgggtcc acgcgtgtga tcgtccgtgc | 120 |
| gtctagcctt tgcccacgca gctttcagtc atggcctccg gtaacgcgcg catcggaaag | 180 |
| ccagcccctg acttcaaggc cacagcggtg gttgatggcg ccttcaaaga ggtgaagctg | 240 |
| tcggactaca aagggaagta cgtggtcctc ttttttctacc ctctggactt cacttttgtg | 300 |
| tgccccaccg agatcatcgc gttcagcaac cgtgcagagg acttccgcaa gctgggctgt | 360 |
| gaagtgctgg gcgtctcggt ggactctcag ttcacccacc tggcttggat caacaccccc | 420 |
| cggaaagagg gaggcttggg cccccttgaac atcccctgc ttgctgacgt gaccagacgc | 480 |
| ttgtctgagg attacggcgt gctgaaaaca gatgagggca ttgcctacag gggcctcttt | 540 |
| atcatcgatg gcaagggtgt ccttcgccag atcactgtta atgatttgcc tgtgggacgc | 600 |
| tccgtggatg aggctctgcg gctggtccag gccttccagt acacagacga gcatgggaa | 660 |
| gtttgtcccg ctggctggaa gcctggcagt gacacgatta agcccaacgt ggatgacagc | 720 |
| aaggaatatt tctccaaaca caattaggct ggctaacgga tagtgagctt gtgccctgc | 780 |
| ctaggtgcct gtgctgggtg tccacctgtg ccccacctg ggtgccctat gctgacccag | 840 |
| gaaaggccag acctgcccct ccaaactcca cagtatggga ccctggaggg ctaggccaag | 900 |
| gccttctcat gcctccacct agaagctgaa tagtgacgcc ctcccccaag cccacccagc | 960 |
| cgcacacagg cctagaggta accaataaag tattagggaa aggtgtgaaa aaaaaaaaa | 1020 |
| aaaaaaaaa aaaaaaaa | 1039 |

<210> SEQ ID NO 11
<211> LENGTH: 2799
<212> TYPE: DNA
<213> ORGANISM: Homo sapiens

<400> SEQUENCE: 11

| | |
|---|---|
| acgtgtgcgg gagggaagca ggaagtgact gcgggagtgg agccggcgag agagtggcag | 60 |
| cgggggctga tggaagtgca gtgggggctg gagagggcac cctactgtat ccagcatgct | 120 |
| ccaaggccac agctctgtgt tccaggcctt gctggggacc ttcttcacct gggggatgac | 180 |

```
agcagctggg gcagctctcg tgttcgtatt ctctagtgga cagaggcgga tcttagatgg    240
aagtcttggc tttgctgcag gggtcatgtt ggcagcttcc tattggtctc ttctggcccc    300
agcagttgag atggccacgt cctctggggg cttcggtgcc tttgccttct tccctgtggc    360
tgttggcttc acccttggag cggcttttgt ctacttggct gacctcctga tgcctcactt    420
gggtgcagca gaagaccccc agacgaccct ggcactgaac ttcggctcta cgttgatgaa    480
gaagaagtct gatcctgagg gtcccgcgct gctcttccct gagagtgaac tttccatccg    540
gataggtaga gctgggcttc tttcagacaa gagtgagaat ggtgaggcat atcagagaaa    600
gaaggcggca gccactggcc ttccagaggg tcctgctgtc cctgtgcctt ctcgagggaa    660
tctggcacag cccggcggca gcagctggag gaggatcgca ctgctcatct tggccatcac    720
tatacacaac gttccagagg gtctcgctgt tggagttgga tttggggcta tagaaaagac    780
ggcatctgct acctttgaga gtgccaggaa tttggccatt ggaatcggga tccagaattt    840
ccccgagggc ctggctgtca gccttcoctt gcgaggggca ggcttctcca cctggagagc    900
tttctggtat gggcagctga gcggcatggt ggagccoctg gccggggtct ttggtgcctt    960
tgccgtggtg ctggctgagc ccatcctgcc ctacgctctg gcctttgctg ccggtgccat   1020
ggtctacgtg gtcatggacg acatcatccc cgaagcccag atcagtggta atgggaaact   1080
ggcatcctgg gcctccatcc tgggatttgt agtgatgatg tcactggacg ttggcctggg   1140
ctagggctga gacgcttcgg accccgggaa aggccatacg aagaaacagc agtggttggc   1200
ttctatggga caacaagctt ctttcttcac attaaaactt tttccttcc tctcttcttc    1260 atctcattat cctgattgac tctgattata atagaaccat ttttactttg ctttgaggga   1320 gattttttgat ttaatgggga attttaaggt gtcatggaaa tacagattct ttgttttggc   1380
cactgaatgg actctctctt cagtgggatt atcaaggaac ttcagatcag ggaaatctcc   1440
acttcgggac cttctatctg cctcccaact cctcaaggtc acctatagaa gcgagctacc   1500
aaaagacgtc tcctaagcat tttggtggcc tagtgactca gggcagagtg gccagcacac   1560
ctctcatccg cccctcctgc tccatcactg ctgagcctct ccccatctag aatgttggaa   1620
ctggagcatc ataaagatag caagctacct tccaaggccg agccagccca gagaggagca   1680
tgtcttcctt tacctccccc taaggagata ctacatggga gggggacaca gaaaaaggga   1740
aggaaattgg ctagtctggc ttttttttttt tttttttttta aaggcaaaga ttgacattat   1800
tgaaggaaag gggatgagga caactgtgaa ctcacagtga gccctgtgga aagaagagac   1860
agacagagtg tgggtttgtt cggaggcctc tgctgtcaat ggattccagg agcaaggcca   1920
tttgtcgcgc tttccaaatt tcttaggcat ttattttgat aagtttatag ccatcatgtt   1980
tctaagagac ttggagacac cagcaaactg ctagaactca aactcttcaa ttactcaaag   2040
aaggagccat ttcagttaac tcaagtgaat gaaagagttt tggaatctgc tgtgggtcct   2100
tccctgttga ccatttggta acttataatc tgacaaaaac tcttgagctg caacaggcct   2160
tgccagaggg ctcaggatgg gaaaggaaga agggatagg aaaagaagag gtaattttac   2220 atttccccctt taaagtaaat tttagccaac tcatcattct gaaatgtccc tataaagaat   2280
gagtcgaact agaccagaag ccagcctact ccttcttaca tagcttctcc aacagggta   2340 gcaatgacct gtccacttca aacacagata aggcctgcca tcctcattgg ttaaaggcac   2400
acgtgagact ttcagtgggc tctgctgaga aggaaggcag cccaggagtc aggtatgcag   2460
gcattgcatt gtcagtgtct gctctcagag tttacacatt caattgcttc caagggtgaa   2520
tctcctgctc tgtgaatgct atcagacccc aaaggccaac cttgggctgg gtctatgtac   2580
```

```
gttcttccga agcactgatg atcaaaattg aagacacatt cagaggtttg attggttgag    2640
attaactggt gtggtggttg gtgtatgtat gttttatttt tatgtctttg tatgtagttc    2700
tacataatgc aaattgtgct ttctgatgga caagacctca taactgtgat taatatcaat    2760
aaaaagggga tgttgtggat gaaaaaaaaa aaaaaaaaa                           2799

<210> SEQ ID NO 12
<211> LENGTH: 981
<212> TYPE: DNA
<213> ORGANISM: Homo sapiens

<400> SEQUENCE: 12
gtttggggcc agagtgggcg aggcgcggag gtctggccta taaagtagtc gcggagacgg      60
ggtgctggtt tgcgtcgtag tctcctgcag cgtctgggt ttccgttgca gtcctcggaa     120
ccaggacctc ggcgtggcct agcgagttat ggcgacgaag gccgtgtgcg tgctgaaggg    180
cgacggccca gtgcagggca tcatcaattt cgagcagaag gaaagtaatg gaccagtgaa    240
ggtgtgggga agcattaaag gactgactga aggcctgcat ggattccatg ttcatgagtt    300
tggagataat acagcaggct gtaccagtgc aggtcctcac tttaatcctc tatccagaaa    360
acacggtggg ccaaggatg aagagaggca tgttggagac ttgggcaatg tgactgctga     420
caaagatggt gtgccgatg tgtctattga agattctgtg atctcactct caggagacca     480
ttgcatcatt ggccgcacac tggtggtcca tgaaaaagca gatgacttgg gcaaaggtgg    540
aaatgaagaa agtacaaaga caggaaacgc tggaagtcgt ttggcttgtg gtgtaattgg    600
gatcgcccaa taaacattcc cttggatgta gtctgaggcc cttaactca tctgttatcc     660 tgctagctgt agaaatgtat cctgataaac attaaacact gtaatcttaa aagtgtaatt    720
gtgtgacttt ttcagagttg cttaaagta cctgtagtga gaaactgatt tatgatcact     780
tggaagattt gtatagtttt ataaaactca gttaaaatgt ctgtttcaat gacctgtatt    840
ttgccagact taaatcacag atgggtatta aacttgtcag aatttctttg tcattcaagc    900
ctgtgaataa aaaccctgta tggcacttat tatgaggcta ttaaaagaat ccaaattcaa    960
actaaaaaaa aaaaaaaaa a                                               981

<210> SEQ ID NO 13
<211> LENGTH: 508
<212> TYPE: DNA
<213> ORGANISM: Homo sapiens

<400> SEQUENCE: 13
tttggtgctt tggatccatt tccatcggtc cttacagccg ctcgtcagac tccagcagcc      60
aagatggtga agcagatcga gagcaagact gcttttcagg aagccttgga cgctgcaggt    120
gataaacttg tagtagttga cttctcagcc acgtggtgtg ggccttgcaa aatgatcaag    180
cctttctttc attccctctc tgaaaagtat tccaacgtga tattccttga agtagatgtg    240
gatgactgtc aggatgttgc ttcagagtgt gaagtcaaat gcatgccaac attccagttt    300
tttaagaagg gacaaaaggt gggtgaattt tctggagcca ataaggaaaa gcttgaagcc    360
accattaatg aattagtcta atcatgtttt ctgaaaatat aaccagccat ggctatttta    420
aaacttgtaa ttttttttaat ttacaaaaat ataaatatg aagacataaa cccagttgcc    480
atctgcgtga caataaaaca ttaatgct                                        508

<210> SEQ ID NO 14
```

```
<211> LENGTH: 1591
<212> TYPE: DNA
<213> ORGANISM: Homo sapiens

<400> SEQUENCE: 14
ccctgcgtct ctgcccgccc cgtggcgccc gagtgcactg aagatggcgg ctgctgtagg      60
acggttgctc cgagcgtcgg ttgcccgaca tgtgagtgcc attccttggg gcatttctgc     120
cactgcagcc ctcaggcctg ctgcatgtgg aagaacgagc ttgacaaatt tattgtgttc     180
tggttccagt caagcaaaat tattcagcac cagttcctca tgccatgcac ctgctgtcac     240
ccagcatgca ccctatttta agggtacagc cgttgtcaat ggagagttca agacctaag      300
ccttgatgac tttaagggga atatttggt gcttttcttc tatcctttgg atttcacctt      360
tgtgtgtcct acagaaattg ttgcttttag tgacaaagct aacgaatttc acgacgtgaa     420
ctgtgaagtt gtcgcagtct cagtggattc ccactttagc catcttgcct ggataaatac     480
accaaggaag aatggtggtt tgggccacat gaacatcgca ctcttgtcag acttaactaa     540
gcagatttcc cgagactacg gtgtgctgtt agaaggttct ggtcttgcac taagaggtct     600
cttcataatt gaccccaatg gagtcatcaa gcatttgagc gtcaacgatc tcccagtggg     660
ccgaagcgtg gaagaaaccc tccgcttggt gaaggcgttc cagtatgtag aaacacatgg     720
agaagtctgc ccagcgaact ggacaccgga ttctcctacg atcaagccaa gtccagctgc     780
ttccaaagag tactttcaga aggtaaatca gtagatcacc catgtgtatc tgcaccttct     840
caactgagag aagaaccaca gttgaaacct gcttttatca ttttcaagat ggttatttgt     900
agaaggcaag gaaccaatta tgcttgtatt cataagtatt actctaaatg ttttgttttt     960
gtaattctgg ctaagacctt ttaaacatgg ttagttgcta gtacaaggaa tcctttattg    1020
gtaacatctt ggtggctggc tagctagttt ctacagaaca taatttgcct ctatagaagg    1080
ctattcttag atcatgtctc aatggaaaca ctcttctttc ttagccttac ttgaatcttg    1140
cctataataa agtagagcaa cacacattga aagcttctga tcaacggtcc tgaaattttc    1200
atcttgaatg tctttgtatt aaactgaatt ttcttttaag ctaacaaaga tcataatttt    1260
caatgattag ccgtgtaact cctgcaatga atgtttatgt gattgaagca aatgtgaatc    1320
gtattatttt aaaaagtggc agagtgactt aactgatcat gcatgatccc tcatccctga    1380
aattgagttt atgtagtcat tttacttatt ttattcatta gctaactttg tctatgtata    1440
tttctagata ttgattagtg taatcgatta taaaggatat ttatcaaatc cagggattgc    1500
attttgaaat tataattatt ttctttgctg aagtattcat tgtaaaacat acaaaataaa    1560
catatttaa aacatttgca tttaccacc a                                     1591

<210> SEQ ID NO 15
<211> LENGTH: 1246
<212> TYPE: DNA
<213> ORGANISM: Homo sapiens

<400> SEQUENCE: 15
gtctttgccc tcgcgacgcc gccacctccg gaacaagcca tggtggcggc gacggtggca      60
gcggcgtggc tgctcctgtg ggctgcggcc tgcgcgcagc aggagcagga cttctacgac     120
ttcaaggcgg tcaacatccg gggcaaactg gtgtcgctgg agaagtaccg cggatcggtg     180
tccctggtgg tgaatgtggc cagcgagtgc ggcttcacag accagcacta ccgagccctg     240
cagcagctgc agcgagacct gggcccccac cactttaacg tgctcgcctt ccctgcaac     300
cagtttggcc aacaggagcc tgacagcaac aaggagattg agagctttgc ccgccgcacc     360
```

```
tacagtgtct cattccccat gtttagcaag attgcagtca ccggtactgg tgcccatcct    420
gccttcaagt acctggccca gacttctggg aaggagccca cctggaactt ctggaagtac    480
ctagtagccc cagatggaaa ggtggtaggg gcttgggacc caactgtgtc agtggaggag    540
gtcagacccc agatcacagc gctcgtgagg aagctcatcc tactgaagcg agaagactta    600
taaccaccgc gtctcctcct ccaccacctc atcccgccca cctgtgtggg gctgaccaat    660
gcaaactcaa atggtgcttc aaagggagag acccactgac tctccttcct ttactcttat    720
gccattggtc ccatcattct tgtggggaaa aaattctagt attttgatta tttgaatctt    780
acagcaacaa ataggaactc ctggccaatg agagctcttg accagtgaat caccagccga    840
tacgaacgtc ttgccaacaa aaatgtgtgg caaatagaag tatatcaagc aataatctcc    900
cacccaaggc ttctgtaaac tgggaccaat gattacctca tagggctgtt gtgaggatta    960
ggatgaaata cctgtgaaag tgcctaggca gtgccagcca ataggaggc attcaatgaa    1020 cattttttgc atataaacca aaaaataact tgttatcaat aaaaacttgc atccaacatg   1080
aatttccagc cgatgataat ccaggccaaa ggtttagttg ttgttatttc ctctgtatta   1140
ttttcttcat tacaaaagaa atgcaagttc attgtaacaa tccaaacaat acctcacgat   1200
ataaaataaa aatgaaagta tcctcctcaa aaaaaaaaaa aaaaaa                  1246
```

<210> SEQ ID NO 16
<211> LENGTH: 942
<212> TYPE: DNA
<213> ORGANISM: Homo sapiens

<400> SEQUENCE: 16

```
gagcgctctg gagggcgtgg ccgtggggaaa ggaggcgcgg aaagccgacg cgcgtccatt    60
ggtcggctgg acgaggggag gagccgctgg ctcccagccc cgccgcgatg agcctcggcc   120
gcctttgccg cctactgaag ccggcgctgc tctgtggggc tctggccgcg cctggcctgg   180
ccgggaccat gtgcgcgtcc cgggacgact ggcgctgtgc gcgctccatg cacgagtttt   240
ccgccaagga catcgacggg cacatggtta acctggacaa gtaccggggc ttcgtgtgca   300
tcgtcaccaa cgtggcctcc cagtgaggca agaccgaagt aaactacact cagctcgtcg   360
acctgcacgc ccgatacgct gagtgtggtt tgcggatcct ggccttcccg tgtaaccagt   420
tcgggaagca ggagccaggg agtaacgaag agatcaaaga gttcgccgcg ggctacaacg   480
tcaaattcga tatgttcagc aagatctgcg tgaacgggga cgacgcccac ccgctgtgga   540
agtggatgaa gatccaaccc aagggcaagg gcatcctggg aaatgccatc aagtggaact   600
tcaccaagtt cctcatcgac aagaacggct gcgtggtgaa gcgctacgga cccatggagg   660 agccctggt gatagagaag gacctgcccc actatttcta gctccacaag tgtgtggccc    720
cgcccgagcc cctgcccacg cccttggagc cttccaccgg cactcatgac ggcctgcctg   780
caaacctgct ggtggggcag acccgaaaat ccagcgtgca ccccgccgga ggaaggtccc   840
atggcctgct gggcttggct cggcgccccc accctggct accttgtggg aataaacaga    900
caaattagcc tgctggaaaa aaaaaaaaa aaaaaaaaaa aa                       942
```

<210> SEQ ID NO 17
<211> LENGTH: 1342
<212> TYPE: DNA
<213> ORGANISM: Homo sapiens

<400> SEQUENCE: 17

| | |
|---|---|
| gaggaagtga cgacaggcgt gcccttgaca ggcagggagg gctaggctgt gcatccctcc | 60 |
| gctcgcattg cagggagatg gctcagcgac ttcttctgag gaggttcctg gcctctgtca | 120 |
| tctccaggaa gccctctcag ggtcagtggc caccccctcac ttccagagcc ctgcagaccc | 180 |
| cacaatgcag tcctggtggc ctgactgtaa cacccaaccc agcccggaca atatacacca | 240 |
| cgaggatctc cttgacaacc tttaatatcc aggatggacc tgactttcaa gaccgagtgg | 300 |
| tcaacagtga gacaccagtg gttgtggatt tccacgcaca gtggtgtgga ccctgcaaga | 360 |
| tcctggggcc gaggttagag aagatggtgg ccaagcagca cgggaaggtg gtgatggcca | 420 |
| aggtggatat tgatgaccac acagacctcg ccattgagta tgaggtgtca gcggtgccca | 480 |
| ctgtgctggc catgaagaat ggggacgtgg tggacaagtt tgtgggcatc aaggatgagg | 540 |
| atcagttgga ggccttcctg aagaagctga ttggctgaca agcagggatg agtcctggtt | 600 |
| cccttgcccg cgtgggaccc caatagaact cagcccttcc atgccagccc ttcctgctgc | 660 |
| ctccctcctg tctggctcct ggggcccatg cttagagccc aggctccagc cctgagtgct | 720 |
| tccgagctgg cggactgccc aggggccatc agaggatggt ggtgctgctg ctgatccggg | 780 |
| gaccgctgtc ttccctccca tacgcctttc atccctcctt ctagggccta tggcagttct | 840 |
| cccaggatgt gtggcgagag cctgggccag cccacagcgt tcctagtcag gcagccacac | 900 |
| cttggtcctc atcttggtcc cttccaatct gaaacctcgt gcctggctcg tctgccacct | 960 |
| acatttctct ttccagctgc tgttttgtaa aagaaaaag aaaaagaag cccaaactag | 1020 |
| tgagagtaat atctaattat ctcatttttt gtaggtctgt gataaagaac ttagtcatcc | 1080 |
| cttccacctc ctactgtgaa gaacagaccc tgggtcccac actgaaatcc cctctagtca | 1140 |
| cccattccca ccccccaggg agctgcctcc caggcagggg gtgcagaaaa tgattgatgg | 1200 |
| gctggggaac cctggagagc ctcgactccg gaagtctcaa ggtgcctcct cctctcctta | 1260 |
| gctggcccgt tggttttctg agcaggggggc tgaactgtga acaagtcaga caaataaagc | 1320 |
| aagggtctgc accatcaaaa aa | 1342 |

<210> SEQ ID NO 18
<211> LENGTH: 921
<212> TYPE: DNA
<213> ORGANISM: Homo sapiens

<400> SEQUENCE: 18

| | |
|---|---|
| gcggcgctcg cgccaaggga cgtgtttctg cgctcgcgtg gtcatggagg cgctgccgct | 60 |
| gctagccgcg acaactccgg accacggccc ccaccgaagg ctgcttctgc tgccgctact | 120 |
| gctgttcctg ctgccggctg gagctgtgca gggctggag acagaggaga ggccccggac | 180 |
| tcgcgaagag gagtgccact tctacgcggg tggacaagtg tacccgggag aggcatcccg | 240 |
| ggtatcggtc gccgaccact ccctgcacct aagcaaagcg aagatttcca gccagcgcc | 300 |
| ctactgggaa ggaacagctg tgatcgatgg agaatttaag gagctgaagt taactgatta | 360 |
| tcgtgggaaa tacttggttt tcttcttcta cccacttgat ttcacatttg tgtgtccaac | 420 |
| tgaaattatc gcttttggcg acagacttga agaattcaga tctataaata ctgaagtggt | 480 |
| agcatgctct gttgattcac agtttaccca tttggcctgg attaatacccc ctcgaagaca | 540 |
| aggaggactt gggccaataa ggattccact tctttcagat ttgacccatc agatctcaaa | 600 |
| ggactatggt gtatacctag aggactcagg ccacactctt agaggtctct tcattattga | 660 |
| tgacaaagga atcctaagac aaattactct gaatgatctt cctgtgggta gatcagtgga | 720 |
| tgagacacta cgtttggttc aagcattcca gtacactgac aaacacggag aagtctgccc | 780 | tgctggctgg aaacctggta gtgaaacaat aatcccagat ccagctggaa agctgaagta    840 tttcgataaa ctgaattgag aaatacttct tcaagttatg atgcttgaaa gttctcaata    900 aagttcacgg tttcattacc a                                              921

<210> SEQ ID NO 19
<211> LENGTH: 1200
<212> TYPE: DNA
<213> ORGANISM: Homo sapiens

<400> SEQUENCE: 19
cagttaaaag gaggcgcctg ctggcctccc cttacagtgc ttgttcgggg cgctccgctg     60
gcttcttgga caattgcgcc atgtgtgctg ctcggctagc ggcggcggcg gcggcggccc    120
agtcggtgta tgccttctcg gcgcgcccgc tggccggcgg ggagcctgtg agcctgggct    180
ccctgcgggg caaggtacta cttatcgaga atgtggcgtc cctctgaggc accacggtcc    240
gggactacac ccagatgaac gagctgcagc ggcgcctcgg accccggggc ctggtggtgc    300
tcggcttccc gtgcaaccag tttgggcatc aggtgcgccg ggcggagcgg ggcggggcgg    360
gggcggacgt gcagtagtgg ctgggggcgc cggcggtgtg ctggtgggtg ccgtcggctc    420
catgcgcgga gagtctggct actctctcgt ttcctttctg ttgctcgtag ctgctgaaat    480
tcctctccgc ccttgggatt gcgcatggag ggcaaaatcc cggtgactca tagaaaatct    540
cccttgtttg tggttagaac gtttctctcc tcctcttgac cccgggttct agctgccctt    600
ctctcctgta ggagaacgcc aagaacgaag agattctgaa ttccctcaag tacgtccggc    660
ctggtggtgg gttcgagccc aacttcatgc tcttcgagaa gtgcgaggtg aacggtgcgg    720
gggcgcaccc tctcttcgcc ttcctgcggg aggccctgcc agctcccagc gacgacgcca    780
ccgcgcttat gaccgacccc aagctcatca cctggtctcc ggtgtgtcgc aacgatgttg    840
cctggaactt tgagaagttc ctggtgggcc ctgacggtgt gccccacgc aggtacagcc    900 gccgcttcca gaccattgac atcgagcctg acatcgaagc cctgctgtct caagggccca    960
gctgtgccta gggcgcccct cctacccccgg ctgcttggca gttgcagtgc tgctgtctcg   1020 gggggggtttt catctatgag ggtgtttcct ctaaacctac gagggaggaa cacctgatct   1080
tacagaaaat accacctcga gatgggtgct ggtcctgttg atcccagtct ctgccagacc   1140
aaggcgagtt tccccactaa taaagtgccg ggtgtcagca gaaaaaaaaa aaaaaaaaaa   1200

<210> SEQ ID NO 20
<211> LENGTH: 1274
<212> TYPE: DNA
<213> ORGANISM: Homo sapiens

<400> SEQUENCE: 20
gcttctgtct ggcggcggca gcatggcggc gggggcggct gaggcagctg tagcggccgt     60
ggaggaggtc ggctcagccg ggcagtttga ggagctgctg cgcctcaaag ccaagtccct    120
ccttgtggtc catttctggg caccatgggc tccacagtgt gcacagatga acgaagttat    180
ggcagagtta gctaaagaac tccctcaagt ttcatttgtg aagttggaag ctgaaggtgt    240
tcctgaagta tctgaaaaat atgaaattag ctctgttccc acttttctgt ttttcaagaa    300
ttctcagaaa atcgaccgat tagatggtgc acatgcccca gagttgacca aaaaagttca    360
gcgacatgca tctagtggct ccttcctacc cagcgctaat gaacatctta agaagatct    420 caaccttcgc ttgaagaaat tgactcatgc tgcccctgc atgctgttta tgaaaggaac    480

```
tcctcaagaa ccacgctgtg gtttcagcaa gcagatggtg gaaattcttc acaaacataa      540
tattcagttt agcagttttg atatcttctc agatgaagag gttcgacagg gactcaaagc      600
ctattccagt tggcctacct atcctcagct ctatgtttct ggagagctca taggaggact      660
tgatataatt aaggagctag aagcatctga agaactagat acaatttgtc ccaaagctcc      720
caaattagag gaaaggctca aagtgctgac aaataaagct tctgtgatgc tctttatgaa      780
aggaaacaaa caggaagcaa aatgtggatt cagcaaacaa attctggaaa tactaaatag      840
tactggtgtt gaatatgaaa cattcgatat attggaggat gaagaagttc ggcaaggatt      900
aaaagcttac tcaaattggc caacataccc tcagctgtat gtgaaagggg agctggtggg      960
aggattggat attgtgaagg aactgaaaga aaatggtgaa ttgctgccta tactgagagg     1020
agaaaattaa taaatcttaa acttggtgcc aactattgt aagaaatatt taattacatt     1080
gggagcagtt catgatttag tcctcagaaa tggactagga atagaaaatt cctgctttct     1140
cagttacatg tttttgtgtat ttcacaatgt cgtgctaaat aaatgtatgt tacatttttt     1200
tcccaccaaa aatagaatgc aataaacatc ttcaaattat taacgaaaaa aaaaaaaaaa     1260
aaaaaaaaaa aaaa                                                      1274
```

<210> SEQ ID NO 21
<211> LENGTH: 710
<212> TYPE: DNA
<213> ORGANISM: Homo sapiens

<400> SEQUENCE: 21

```
gctcgtccgc tccctccccc gcgccgtgca cgtcttggtt cgggccgggc ataaaaggct       60
tcgcggccca gggctcactt ggcgctgaga acgcgggtcc acgcgtgtga tcgtccgtgc      120
gtctagcctt tgcccacgca gctttcagtc atggcctccg gtaacgcgcg catcggaaag      180
ccagcccctg acttcaaggc cacagcggtg gttgatggcg ccttcaaaga ggtgaagctg      240
tcggactaca aagggaagta cgtggtcctc ttttctacc ctctggactt cacttttgtg      300
tgccccaccg agatcatcgc gttcagcaac cgtgcagagg acttccgcaa gctgggctgt      360
gaagtgctgg cgtctcggt ggactctcag ttcacccacc tggcttggta tgagcagggg      420
ccaaagaggg aggttgcagc taagctcaca ccctcaggtc ctagcagtgt ggcttcgtgg      480
ccattgctca acctctggaa cctgcgtttc cccatcgtga aaataatgga acattgccg      540 cccaagtctt taaggatgat gacagtaatt agcatttgac aactagttgc ctggtatata      600
gagttgcaga tgcaactcag atgcaactct atctactcta tgtacttagt tcccaggagg      660
gaggctgtgc tgccctattt catgaagatg gaaactccag ttcaccgaag                 710
```

<210> SEQ ID NO 22
<211> LENGTH: 1715
<212> TYPE: DNA
<213> ORGANISM: Homo sapiens

<400> SEQUENCE: 22

```
gaaccaaccg gttgcttgct gtcccagcgg cgccccctca tcaccgtcgc catgcccgga       60
ggtctgcttc tcggggacgt ggctcccaac tttgaggcca ataccaccgt cggccgcatc      120
cgtttccacg actttctggg agactcatgg ggcattctct ctcccaccc tcgggacttt      180 accccagtgt gcaccacaga gcttggcaga gctgcaaagc tggcaccaga atttgccaag      240
aggaatgtta agttgattgc ccttttcaata gacagtgttg aggaccatct tgcctggagc      300
aaggatatca atgcttacaa ttgtgaagag cccacagaaa agttaccttt tcccatcatc      360
```

```
gatgatagga atcgggagct tgccatcctg ttgggcatgc tggatccagc agagaaggat      420
gaaaagggca tgcctgtgac agctcgtgtg gtgtttgttt ttggtcctga taagaagctg      480
aagctgtcta tcctctaccc agctaccact ggcaggaact tgatgagat tctcagggta       540 gtcatctctc tccagctgac agcagaaaaa agggttgcca ccccagttga ttggaaggat      600
ggggatagtg tgatggtcct tccaaccatc cctgaagaag aagccaaaaa acttttcccg      660
aaaggagtct tcaccaaaga gctcccatct ggcaagaaat acctccgcta cacccccag       720 ccttaagtct cttggagaag ctggtgctgt gagccagagg atgtcagctg ccaattgtgt      780
tttcctgcag caattccata aacacatcct ggtgtcatca cagccaaggt ttttaggttg      840
ctataccaat ggcttattaa atgaaaatgg cactaaaagt ttcttgagat tctttatact      900
ctctgccttc agcaatcaat tccattcata catcagcact ctgctggttc tgtttgaaat      960
atgttctgta tttaaaactc aaatcttgtt ggatctctgc agggcttgtg accaatgaag     1020
tcatatttgt tgatggttga caaagcttgc ttcactccat cagagaatga ctatcaattt     1080 tttttaact gtcctatcac gtcctctcct gtcacccatt ttgaagagtg gcagaacttg      1140
aagttcaact tcctctgtaa atatccaagt ataaagccca ggaacttcta gaataaccca     1200
gatgcgcttt aattttttt aatatgtttt gatcacagaa cttctagaat aacccagatg      1260
ctctttcata ttcttttaat acatcttgat cacagctggg ggaaaaaaag cttttttaatt     1320 ctataccttc ctagtagata agtgaagagc agggaaagag acctttaaat attttgctat     1380
aaaaaaattt gtgataagtt tctatcaaaa tggggagatt gcagaaaagg cttcccttgg     1440
ctcccaagga ggtgtagcag gtgtgagcaa tattagtgcc atgtgccttt cacacagggt     1500
ttgcatttat cagtctgttt tccgatgatg tgtacatgaa agagtacacc atgtgaagag     1560
aagagagaat gattgaaaat gttttagtat agaactcttc ttgcagtggg ttgctatttt     1620
ctagatttta cttttaggg aacaaaataa aatcctttgt taaaactggg aaaaaaaaaa     1680
aaaaaaaaaa aaaaaaaaaa aaaaaaaaaa aaaaa                                1715
```

<210> SEQ ID NO 23
<211> LENGTH: 1182
<212> TYPE: DNA
<213> ORGANISM: Homo sapiens

<400> SEQUENCE: 23

```
aatgagggcc tccaggggc gggtcggact gccgcgggcc ggggagcgct ctgggtggcc       60
agctgtgggc ccgggccgtc gtgggctccg gcttgcgtgc ggagatgagc gggtccctcg     120
gccgagctgc ggcggctctg ctccgctggg ggcgcggcgc gggcggcggt ggcctttggg     180
gtccgggcgt gcgggcggcg ggctcggcg cgggcggcgg cggctcggcg gagcagttgg      240
acgcgctggt gaagaaggac aaggtggtgg tcttcctcaa ggggacgccg gagcagcccc     300
agtgcggctt cagcaacgcc gtggtgcaga tcctgcggct gcacggcgtc gcgattacg      360 cggcctacaa cgtgctggac gacccggagc tccgacaagg cattaaagac tattccaact      420
ggcccaccat cccgcaagtg tacctcaatg gcgagtttgt aggggctgt gacattcttc       480 tgcagatgca ccagaatggg gacttggtgg aagaactgaa aaagctgggg atccactccg      540
cccttttaga tgaaaagaaa gaccaagact ccaagtgagg gcggccaagt cctcgctgag      600
cagagaggga gccgttcatg tcagagactc actgccagaa aagccttacc cattttggtt      660
ttcactattg agaccgcaac tgcttgcact gatcattttg gttcgtgagc agttggtgat     720
```

```
tttagttggt ctggtgttcg ggctaagaat attttattgt ggacttaatt acaaccactg      780
cactgtaatg attcaatgct gtattatgat attgctgtaa acaaaattca ttcttatatt      840
gtcacttatt ctttgcctga ttcagaagtt aaataggagc tttggaatca ttattcatga      900
cccctctgca aatgtgtcag tctccaaaga gagtatctcc ccccaaattt tgtgtagctt      960
cttttgttat ggaaaatggt gaacaaaaaa agaaactgtg ataactgggg cgttgttttt     1020
taaaataaac tccagcacag ggatgctgtg catgcctgag ttgattccga agtgcatatg     1080
tctgtaagga tttggagtgc ctgcagtgtt ttatgtgtgg gaagtaaggg tgagtctcat     1140
attcttctat taaatttgcc acaagaattg caaaaaaaaa aa                        1182
```

<210> SEQ ID NO 24
<211> LENGTH: 1170
<212> TYPE: DNA
<213> ORGANISM: Homo sapiens

<400> SEQUENCE: 24

```
aaggctatta ttaccaccac tgagtggctt aaataatcct gtcaacagca atcgcccatt       60
tccaaagcca tggtgaaaca tctctgtgct aatttctttt gttttgtttc ctaattttt      120 ttttttggca ggtggtggga aataatcttt gtcttctttg gagtaaacct tcaacaccgg      180 atttttctt ttaattatgg atgtaaaccc caatatcccc ataatttaca ttgggtctcg       240
accaattgcc taattataag aggatatatt taggctctta tttcatccac acaaaaactt      300
gtgtaacagg tagttggaaa catctgaggc accactttga ttctgttttg gatggtcatg      360
ttttttctcc tccgtttccc cagcatgtct gccaccatcc tcatgcactg cttccaagtg      420
cctgggagcc tttatgagcg tccctaaacc taaaagaatc cagaggcggg gctcggatga      480
accctcgaga taagcaagtg agccgcttct cccctctaaa ggatgtttac acgtgggtgg      540
cactcgctgg aatccagcgc tcgggcagcc ctgggaggac gcgctcagct gcgaggagga      600
tggagagcaa tacatcatca tctttggaga atttagcgac ggcgcctgtg aaccagatcc      660
aagaaacaat ttctgataat tgtgtggtga ttttctcaaa aacatcctgt tcttactgta      720
caatggcaaa aaagcttttc catgacatga atgttaacta taagtggtg gaactggacc      780 tgcttgaata tggaaaccag ttccaagatg ctctttacaa aatgactggt gaaagaactg      840
ttccaagaat atttgtcaat ggtactttta ttggaggtgc aactgacact cataggcttc      900
acaaagaagg aaaattgctc ccactagttc atcagtgtta tttaaaaaaa agtaagagga      960
aagaatttca gtgatgttta tactaataag tttgctagta cagtgtcagt tatttaaagt     1020
ggtaatgccc gataatgtct tttaaatgtt tgaggatgtt ttaaatacat gcattgtctt     1080
cacgaagaag atgtaaaaat aatgaacaat aaattgcggt ggaaacctaa aaaaaaaaa     1140 aaaaaaaaaa aaaaaaaaaa aaaaaaaaaa                                     1170
```

<210> SEQ ID NO 25
<211> LENGTH: 18
<212> TYPE: DNA
<213> ORGANISM: Artificial sequence
<220> FEATURE:
<223> OTHER INFORMATION: oligonucleotide sens

<400> SEQUENCE: 25

```
gggagctgag ggcaagtc                                                    18
```

<210> SEQ ID NO 26
<211> LENGTH: 19

```
<212> TYPE: DNA
<213> ORGANISM: Artificial sequence
<220> FEATURE:
<223> OTHER INFORMATION: oligonucleotide antisens

<400> SEQUENCE: 26
gagacccttg cagccaatc                                                    19

<210> SEQ ID NO 27
<211> LENGTH: 19
<212> TYPE: DNA
<213> ORGANISM: Artificial sequence
<220> FEATURE:
<223> OTHER INFORMATION: oligonucleotide sens

<400> SEQUENCE: 27
caaccagttt gggcatcag                                                    19

<210> SEQ ID NO 28
<211> LENGTH: 19
<212> TYPE: DNA
<213> ORGANISM: Artificial sequence
<220> FEATURE:
<223> OTHER INFORMATION: oligonucleotide antisens

<400> SEQUENCE: 28
gttcacctcg cacttctcg                                                    19

<210> SEQ ID NO 29
<211> LENGTH: 18
<212> TYPE: DNA
<213> ORGANISM: Artificial sequence
<220> FEATURE:
<223> OTHER INFORMATION: oligonucleotide sens

<400> SEQUENCE: 29
gctggtttgg agcaggag                                                     18

<210> SEQ ID NO 30
<211> LENGTH: 24
<212> TYPE: DNA
<213> ORGANISM: Artificial sequence
<220> FEATURE:
<223> OTHER INFORMATION: oligonucleotide antisens

<400> SEQUENCE: 30
ccaaagatga tgatgtattg ctct                                              24

<210> SEQ ID NO 31
<211> LENGTH: 18
<212> TYPE: DNA
<213> ORGANISM: Artificial sequence
<220> FEATURE:
<223> OTHER INFORMATION: oligonucleotide sens

<400> SEQUENCE: 31
cgcagttcgg ttctccac                                                     18

<210> SEQ ID NO 32
<211> LENGTH: 18
<212> TYPE: DNA
<213> ORGANISM: Artificial sequence
<220> FEATURE:
<223> OTHER INFORMATION: oligonucleotide antisens

<400> SEQUENCE: 32
```

```
gggtcccgaa ctgtgtca                                                     18

<210> SEQ ID NO 33
<211> LENGTH: 21
<212> TYPE: DNA
<213> ORGANISM: Artificial sequence
<220> FEATURE:
<223> OTHER INFORMATION: oligonucleotide sens

<400> SEQUENCE: 33
cactgacaaa catggggaag t                                                 21

<210> SEQ ID NO 34
<211> LENGTH: 21
<212> TYPE: DNA
<213> ORGANISM: Artificial sequence
<220> FEATURE:
<223> OTHER INFORMATION: oligonucleotide antisens

<400> SEQUENCE: 34
tttgctcttt tggacatcag g                                                 21

<210> SEQ ID NO 35
<211> LENGTH: 18
<212> TYPE: DNA
<213> ORGANISM: Artificial sequence
<220> FEATURE:
<223> OTHER INFORMATION: oligonucleotide sens

<400> SEQUENCE: 35
cacccctgga tgttccaa                                                     18

<210> SEQ ID NO 36
<211> LENGTH: 22
<212> TYPE: DNA
<213> ORGANISM: Artificial sequence
<220> FEATURE:
<223> OTHER INFORMATION: oligonucleotide antisens

<400> SEQUENCE: 36
ggacaccagc gaatcatcta gt                                                22

<210> SEQ ID NO 37
<211> LENGTH: 20
<212> TYPE: DNA
<213> ORGANISM: Artificial sequence
<220> FEATURE:
<223> OTHER INFORMATION: oligonucleotide sens

<400> SEQUENCE: 37
tccactgcaa ggaacaacag                                                   20

<210> SEQ ID NO 38
<211> LENGTH: 19
<212> TYPE: DNA
<213> ORGANISM: Artificial sequence
<220> FEATURE:
<223> OTHER INFORMATION: oligonucleotide antisens

<400> SEQUENCE: 38
taagcgtgct cccacacat                                                    19

<210> SEQ ID NO 39
<211> LENGTH: 21
<212> TYPE: DNA
<213> ORGANISM: Artificial sequence
```

```
<220> FEATURE:
<223> OTHER INFORMATION: oligonucleotide sens

<400> SEQUENCE: 39
tgccagctta ggaataacca g                                              21

<210> SEQ ID NO 40
<211> LENGTH: 18
<212> TYPE: DNA
<213> ORGANISM: Artificial sequence
<220> FEATURE:
<223> OTHER INFORMATION: oligonucleotide antisens

<400> SEQUENCE: 40
cctgcaccaa caatgacg                                                  18

<210> SEQ ID NO 41
<211> LENGTH: 20
<212> TYPE: DNA
<213> ORGANISM: Artificial sequence
<220> FEATURE:
<223> OTHER INFORMATION: oligonucleotide sens

<400> SEQUENCE: 41
ggcttctgga atttgtcgat                                                20

<210> SEQ ID NO 42
<211> LENGTH: 21
<212> TYPE: DNA
<213> ORGANISM: Artificial sequence
<220> FEATURE:
<223> OTHER INFORMATION: oligonucleotide antisens

<400> SEQUENCE: 42
tgcatccgcc tatacaatct t                                              21

<210> SEQ ID NO 43
<211> LENGTH: 21
<212> TYPE: DNA
<213> ORGANISM: Artificial sequence
<220> FEATURE:
<223> OTHER INFORMATION: oligonucleotide sens

<400> SEQUENCE: 43
gccttccagt acacagacga g                                              21

<210> SEQ ID NO 44
<211> LENGTH: 21
<212> TYPE: DNA
<213> ORGANISM: Artificial sequence
<220> FEATURE:
<223> OTHER INFORMATION: oligonucleotide antisens

<400> SEQUENCE: 44
gttgggctta atcgtgtcac t                                              21

<210> SEQ ID NO 45
<211> LENGTH: 18
<212> TYPE: DNA
<213> ORGANISM: Artificial sequence
<220> FEATURE:
<223> OTHER INFORMATION: oligonucleotide sens

<400> SEQUENCE: 45
tcctggctga tcccactg                                                  18
```

<210> SEQ ID NO 46
<211> LENGTH: 20
<212> TYPE: DNA
<213> ORGANISM: Artificial sequence
<220> FEATURE:
<223> OTHER INFORMATION: oligonucleotide antisens

<400> SEQUENCE: 46
atgccatcct gtaccaccat                                          20

<210> SEQ ID NO 47
<211> LENGTH: 20
<212> TYPE: DNA
<213> ORGANISM: Artificial sequence
<220> FEATURE:
<223> OTHER INFORMATION: oligonucleotide sens

<400> SEQUENCE: 47
gcatcatcaa tttcgagcag                                          20

<210> SEQ ID NO 48
<211> LENGTH: 20
<212> TYPE: DNA
<213> ORGANISM: Artificial sequence
<220> FEATURE:
<223> OTHER INFORMATION: oligonucleotide antisens

<400> SEQUENCE: 48
caggccttca gtcagtcctt                                          20

<210> SEQ ID NO 49
<211> LENGTH: 18
<212> TYPE: DNA
<213> ORGANISM: Artificial sequence
<220> FEATURE:
<223> OTHER INFORMATION: oligonucleotide sens

<400> SEQUENCE: 49
ttacagccgc tcgtcaga                                            18

<210> SEQ ID NO 50
<211> LENGTH: 21
<212> TYPE: DNA
<213> ORGANISM: Artificial sequence
<220> FEATURE:
<223> OTHER INFORMATION: oligonucleotide antisens

<400> SEQUENCE: 50
ggcttcctga aaagcagtct t                                        21

<210> SEQ ID NO 51
<211> LENGTH: 20
<212> TYPE: DNA
<213> ORGANISM: Artificial sequence
<220> FEATURE:
<223> OTHER INFORMATION: oligonucleotide sens

<400> SEQUENCE: 51
ctggacaccg gattctccta                                          20

<210> SEQ ID NO 52
<211> LENGTH: 25
<212> TYPE: DNA
<213> ORGANISM: Artificial sequence
<220> FEATURE:
<223> OTHER INFORMATION: oligonucleotide antisens

<400> SEQUENCE: 52
gggtgatcta ctgatttacc ttctg                                    25

<210> SEQ ID NO 53
<211> LENGTH: 20
<212> TYPE: DNA
<213> ORGANISM: Artificial sequence
<220> FEATURE:
<223> OTHER INFORMATION: oligonucleotide sens

<400> SEQUENCE: 53
ccatcctgcc ttcaagtacc                                          20

<210> SEQ ID NO 54
<211> LENGTH: 20
<212> TYPE: DNA
<213> ORGANISM: Artificial sequence
<220> FEATURE:
<223> OTHER INFORMATION: oligonucleotide antisens

<400> SEQUENCE: 54
ttccatctgg ggctactagg                                          20

<210> SEQ ID NO 55
<211> LENGTH: 18
<212> TYPE: DNA
<213> ORGANISM: Artificial sequence
<220> FEATURE:
<223> OTHER INFORMATION: oligonucleotide sens

<400> SEQUENCE: 55
tacggaccca tggaggag                                            18

<210> SEQ ID NO 56
<211> LENGTH: 22
<212> TYPE: DNA
<213> ORGANISM: Artificial sequence
<220> FEATURE:
<223> OTHER INFORMATION: oligonucleotide antisens

<400> SEQUENCE: 56
ccacacactt gtggagctag aa                                       22

<210> SEQ ID NO 57
<211> LENGTH: 20
<212> TYPE: DNA
<213> ORGANISM: Artificial sequence
<220> FEATURE:
<223> OTHER INFORMATION: oligonucleotide sens

<400> SEQUENCE: 57
gagacaccag tggttgtgga                                          20

<210> SEQ ID NO 58
<211> LENGTH: 19
<212> TYPE: DNA
<213> ORGANISM: Artificial sequence
<220> FEATURE:
<223> OTHER INFORMATION: oligonucleotide antisens

<400> SEQUENCE: 58
gcttggccac catcttctc                                           19

<210> SEQ ID NO 59

```
<211> LENGTH: 20
<212> TYPE: DNA
<213> ORGANISM: Artificial sequence
<220> FEATURE:
<223> OTHER INFORMATION: oligonucleotide sens

<400> SEQUENCE: 59
gcacctaagc aaagcgaaga                                              20

<210> SEQ ID NO 60
<211> LENGTH: 21
<212> TYPE: DNA
<213> ORGANISM: Artificial sequence
<220> FEATURE:
<223> OTHER INFORMATION: oligonucleotide antisens

<400> SEQUENCE: 60
aaattctcca tcgatcacag c                                            21

<210> SEQ ID NO 61
<211> LENGTH: 21
<212> TYPE: DNA
<213> ORGANISM: Artificial sequence
<220> FEATURE:
<223> OTHER INFORMATION: oligonucleotide sens

<400> SEQUENCE: 61
cccttgtttg tggttagaac g                                            21

<210> SEQ ID NO 62
<211> LENGTH: 21
<212> TYPE: DNA
<213> ORGANISM: Artificial sequence
<220> FEATURE:
<223> OTHER INFORMATION: oligonucleotide antisens

<400> SEQUENCE: 62
gagagaaggg cagctagaac c                                            21

<210> SEQ ID NO 63
<211> LENGTH: 19
<212> TYPE: DNA
<213> ORGANISM: Artificial sequence
<220> FEATURE:
<223> OTHER INFORMATION: oligonucleotide sens

<400> SEQUENCE: 63
tcctcaagaa ccacgctgt                                               19

<210> SEQ ID NO 64
<211> LENGTH: 27
<212> TYPE: DNA
<213> ORGANISM: Artificial sequence
<220> FEATURE:
<223> OTHER INFORMATION: oligonucleotide antisens

<400> SEQUENCE: 64
tgagaagata tcaaaactgc taaactg                                      27

<210> SEQ ID NO 65
<211> LENGTH: 26
<212> TYPE: DNA
<213> ORGANISM: Artificial sequence
<220> FEATURE:
<223> OTHER INFORMATION: oligonucleotide sens

<400> SEQUENCE: 65
```
gcaactcaga tgcaactcta tctact                                              26

<210> SEQ ID NO 66
<211> LENGTH: 23
<212> TYPE: DNA
<213> ORGANISM: Artificial sequence
<220> FEATURE:
<223> OTHER INFORMATION: oligonucleotide antisens

<400> SEQUENCE: 66
tgaactggag tttccatctt cat                                                 23

<210> SEQ ID NO 67
<211> LENGTH: 24
<212> TYPE: DNA
<213> ORGANISM: Artificial sequence
<220> FEATURE:
<223> OTHER INFORMATION: oligonucleotide sens

<400> SEQUENCE: 67
caatagacag tgttgaggac catc                                                24

<210> SEQ ID NO 68
<211> LENGTH: 20
<212> TYPE: DNA
<213> ORGANISM: Artificial sequence
<220> FEATURE:
<223> OTHER INFORMATION: oligonucleotide antisens

<400> SEQUENCE: 68
tttctgtggg ctcttcacaa                                                     20

<210> SEQ ID NO 69
<211> LENGTH: 20
<212> TYPE: DNA
<213> ORGANISM: Artificial sequence
<220> FEATURE:
<223> OTHER INFORMATION: oligonucleotide sens

<400> SEQUENCE: 69
gtgataactg gggcgttgtt                                                     20

<210> SEQ ID NO 70
<211> LENGTH: 18
<212> TYPE: DNA
<213> ORGANISM: Artificial sequence
<220> FEATURE:
<223> OTHER INFORMATION: oligonucleotide antisens

<400> SEQUENCE: 70
actcaggcat gcacagca                                                       18

<210> SEQ ID NO 71
<211> LENGTH: 18
<212> TYPE: DNA
<213> ORGANISM: Artificial sequence
<220> FEATURE:
<223> OTHER INFORMATION: oligonucleotide sens

<400> SEQUENCE: 71
gtggcactcg ctggaatc                                                       18

<210> SEQ ID NO 72
<211> LENGTH: 22
<212> TYPE: DNA

<213> ORGANISM: Artificial sequence
<220> FEATURE:
<223> OTHER INFORMATION: oligonucleotide antisens

<400> SEQUENCE: 72

```
cgtcgctaaa ttctccaaag at                                              22
```

<210> SEQ ID NO 73
<211> LENGTH: 1236
<212> TYPE: DNA
<213> ORGANISM: Homo sapiens

<400> SEQUENCE: 73

```
actctcgcga gatccctact ggctataaag gcagcgcccc ggagagctct tgcgcgtctt     60
gttcttgcct ggtgtcggtg gttagtttct gcgacttgtg ttgggactgg tgagtgtggg    120
cagtgcggcc cctgcggagt gaggcgcggc gcgcccttct tgcctgttgc ctcttcctcc    180
tcctgtccgg ggcccgcccg cgctcgggtg ggggtgctgt gatgcgtgag gcagccgggg    240
gaggcccgga gtccgagact gcttgagcgc tgcgcacacc cctctcgtgg gcccccacg     300
tagctgatag gaagatgtct tcaggaaatg ctaaaattgg gcaccctgcc cccaacttca    360
aagccacagc tgttatgcca gatggtcagt ttaaagatat cagcctgtct gactacaaag    420
gaaatatgt tgtgttcttc ttttaccctc ttgacttcac ctttgtgtgc cccacggaga    480
tcattgcttt cagtgatagg gcagaagaat taagaaact caactgccaa gtgattggtg    540
cttctgtgga ttctcacttc tgtcatctag catgggtcaa tacacctaag aaacaaggag    600
gactgggacc catgaacatt cctttggtat cagacccgaa gcgcaccatt gctcaggatt    660
atgggtctt aaaggctgat gaaggcatct cgttcagggg ccttttatc attgatgata    720
agggtattct tcggcagatc actgtaaatg acctccctgt tggccgctct gtggatgaga    780
ctttgagact agttcaggcc ttccagttca ctgacaaaca tggggaagtg tgcccagctg    840
gctgaaaacc tggcagtgat accatcaagc ctgatgtcca aaagagcaaa gaatatttct    900
ccaagcagaa gtgagcgctg ggctgttta gtgccaggct gcggtgggca gccatgagaa    960
caaaacctct tctgtatttt tttttttccat tagtaaaaca caagacttca gattcagccg   1020
aattgtggtg tcttacaagg caggccttc ctacaggggg tggagagacc agcctttctt   1080
cctttggtag gaatgcctg agttggcgtt gtgggcaggc tactggtttg tatgatgtat   1140
tagtagagca acccattaat cttttgtagt ttgtattaaa cttgaactga gaccttgatg   1200
agtcttaaa aaaaaaaaaa aaaaaaaaa aaaaaa                               1236
```

<210> SEQ ID NO 74
<211> LENGTH: 1042
<212> TYPE: DNA
<213> ORGANISM: Homo sapiens

<400> SEQUENCE: 74

```
actctcgcga gatccctact ggctataaag gcagcgcccc ggagagctct tgcgcgtctt     60
gttcttgcct ggtgtcggtg gttagtttct gcgacttgtg ttgggactgc tgataggaag    120
atgtcttcag gaaatgctaa aattgggcac cctgccccca acttcaaagc cacagctgtt    180
atgccagatg gtcagtttaa agatatcagc ctgtctgact acaaaggaaa atatgttgtg    240
ttcttctttt accctcttga cttcaccttt gtgtgcccca cggagatcat tgctttcagt    300
gatagggcag aagaatttaa gaaactcaac tgccaagtga ttggtgcttc tgtggattct    360
cacttctgtc atctagcatg ggtcaataca cctaagaaac aaggaggact gggacccatg    420
```

```
aacattcctt tggtatcaga cccgaagcgc accattgctc aggattatgg ggtcttaaag    480
gctgatgaag gcatctcgtt caggggcctt tttatcattg atgataaggg tattcttcgg    540
cagatcactg taaatgacct ccctgttggc cgctctgtgg atgagacttt gagactagtt    600
caggccttcc agttcactga caaacatggg gaagtgtgcc cagctggctg gaaacctggc    660
agtgatacca tcaagcctga tgtccaaaag agcaagaat atttctccaa gcagaagtga     720
gcgctgggct gttttagtgc caggctgcgg tgggcagcca tgagaacaaa acctcttctg    780 tattttttt ttccattagt aaaacacaag acttcagatt cagccgaatt gtggtgtctt     840
acaaggcagg cctttcctac aggggtggaa gagaccagcc tttcttcctt tggtaggaat    900
ggcctgagtt ggcgttgtgg gcaggctact ggtttgtatg atgtattagt agagcaaccc    960
attaatcttt tgtagtttgt attaaacttg aactgagacc ttgatgagtc tttaaaaaaa   1020
aaaaaaaaaa aaaaaaaaa aa                                             1042

<210> SEQ ID NO 75
<211> LENGTH: 1035
<212> TYPE: DNA
<213> ORGANISM: Homo sapiens

<400> SEQUENCE: 75
gcggtgccct tgcggcgcag ctggggtcgc ggccctgctc cccgcgcttt cttaaggccc     60
gcgggcggcg caggagcggc actcgtggct gtggtggctt cggcagcggc ttcagcagat    120
cggcggcatc agcggtagca ccagcactag cagcatgttg agccgggcag tgtgcggcac    180
cagcaggcag ctggctccgg ttttggggta tctgggctcc aggcagaagc acagcctccc    240
cgacctgccc tacgactacg cgcccctgga acctcacatc aacgcgcaga tcatgcagct    300
gcaccacagc aagcaccacg cggcctacgt gaacaacctg aacgtcaccg aggagaagta    360
ccaggaggcg ttggccaagg gagatgttac agcccagata gctcttcagc ctgcactgaa    420
gttcaatggt ggtggtcata tcaatcatag cattttctgg acaaacctca gccctaacgg    480
tggtggagaa cccaaagggg agttgctgga agccatcaaa cgtgactttg gttcctttga    540
caagtttaag gagaagctga cggctgcatc tgttggtgtc caaggctcag gttggggttg    600
gcttggtttc aataaggaac ggggacactt acaaattgct gcttgtccaa atcaggatcc    660
actgcaagga acaacaggcc ttattccact gctgggggatt gatgtgtggg agcacgctta   720
ctaccttcag tataaaaatg tcaggcctga ttatctaaaa gctatttgga atgtaatcaa    780
ctgggagaat gtaactgaaa gatacatggc ttgcaaaaag taaaccacga tcgttatgct    840
gatcataccc taatgatccc agcaagataa tgtcctgtct tctaagatgt gcatcaagcc    900
tggtacatac tgaaacccct ataaggtcct ggataatttt tgtttgatta ttcattgaag    960
aaacatttat tttccaattg tgtgaagttt ttgactgtta ataaaagaat ctgtcaacca   1020
tcaaaaaaaa aaaaa                                                    1035

<210> SEQ ID NO 76
<211> LENGTH: 918
<212> TYPE: DNA
<213> ORGANISM: Homo sapiens

<400> SEQUENCE: 76
gcggtgccct tgcggcgcag ctggggtcgc ggccctgctc cccgcgcttt cttaaggccc     60
gcgggcggcg caggagcggc actcgtggct gtggtggctt cggcagcggc ttcagcagat    120
```

| | |
|---|---|
| cggcggcatc agcggtagca ccagcactag cagcatgttg agccgggcag tgtgcggcac | 180 |
| cagcaggcag ctggctccgg ttttggggta tctgggctcc aggcagaagc acagcctccc | 240 |
| cgacctgccc tacgactacg gcgccctgga acctcacatc aacgcgcaga tcatgcagct | 300 |
| gcaccacagc aagcaccacg cggcctacgt gaacaacctg aacgtcaccg aggagaagta | 360 |
| ccaggaggcg ttggccaagg gggagttgct ggaagccatc aaacgtgact ttggttcctt | 420 |
| tgacaagttt aaggagaagc tgacggctgc atctgttggt gtccaaggct caggttgggg | 480 |
| ttggcttggt ttcaataagg aacggggaca cttacaaatt gctgcttgtc caaatcagga | 540 |
| tccactgcaa ggaacaacag gccttattcc actgctgggg attgatgtgt gggagcacgc | 600 |
| ttactacctt cagtataaaa atgtcaggcc tgattatcta aaagctattt ggaatgtaat | 660 |
| caactgggag aatgtaactg aaagatacat ggcttgcaaa aagtaaacca cgatcgttat | 720 |
| gctgatcata ccctaatgat cccagcaaga taatgtcctg tcttctaaga tgtgcatcaa | 780 |
| gcctggtaca tactgaaaac cctataaggt cctggataat ttttgtttga ttattcattg | 840 |
| aagaaacatt tattttccaa ttgtgtgaag tttttgactg ttaataaaag aatctgtcaa | 900 |
| ccatcaaaaa aaaaaaaa | 918 |

<210> SEQ ID NO 77
<211> LENGTH: 3087
<212> TYPE: DNA
<213> ORGANISM: Homo sapiens

<400> SEQUENCE: 77

| | |
|---|---|
| tcctcctggg tcttgcctag cggcgggcgc atgcttagtc accgtgaggc tgcgcttgcc | 60 |
| cggggcccgc gcccccctac cccggggacc gccccgggc cgcccgcccc acttggcgcg | 120 |
| ccacttccgc gtgcatggcc ctgctgcccc gagccctgag cgccggcgcg ggaccgagct | 180 |
| ggcggcgggc ggcgcgcgcc ttccgaggct tcctgctgct tctgcccgag cccgcggccc | 240 |
| tcacgcgcgc cctctcccgt gccatggcct gcaggcagga gccgcagccg cagggccccgc | 300 |
| cgcccgctgc tggcgccgtg gcctcctatg actacctggt gatcggggc ggctcgggcg | 360 |
| ggctggccag cgcgcgcagg gcggccgagc tgggtgccag ggccgccgtg gtggagagcc | 420 |
| acaagctggg tggcacttgc gtgaatgttg gatgtgtacc caaaaaggta atgtggaaca | 480 |
| cagctgtcca ctctgaattc atgcatgatc atgctgatta tggctttcca agttgtgagg | 540 |
| gtaaattcaa ttggcgtgtt attaaggaaa agcgggatgc ctatgtgagc cgcctgaatg | 600 |
| ccatctatca aaacaatctc accaagtccc atatagaaat catccgtggc catgcagcct | 660 |
| tcacgagtga tcccaagccc acaatagagg tcagtgggaa aaagtacacc gccccacaca | 720 |
| tcctgatcgc cacaggtggt atgccctcca cccctcatga gagccagatc cccggtgcca | 780 |
| gcttaggaat aaccagcgat ggattttttc agctggaaga attgcccggc cgcagcgtca | 840 |
| ttgttggtgc aggttacatt gctgtggaga tggcagggat cctgtcagcc ctgggttcta | 900 |
| agacatcact gatgatacgg catgataagg tcaaggaggt taaaaagact ttgtcgggct | 960 |
| tggaagtcag catggttact gcagttcccg gtaggctacc agtcatgacc atgattccag | 1020 |
| atgttgactg cctgctctgg gccattgggc gggtcccgaa taccaaggac tgagtttaa | 1080 |
| acaaactggg gattcaaacc gatgacaagg gtcatatcat cgtagacgaa ttccagaata | 1140 |
| ccaacgtcaa aggcatctat gcagttgggg atgtatgtgg aaaagctctt cttactccag | 1200 |
| ttgcaatagc tgctggccga aaacttgccc atcgactttt tgaatataag gaagattcca | 1260 |
| aattagatta taacaacatc ccaactgtgg tcttcagcca cccccctatt gggacagtgg | 1320 |

```
gactcacgga agatgaagcc attcataaat atggaataga aaatgtgaag acctattcaa    1380
cgagctttac cccgatgtat cacgcagtta ccaaaaggaa aacaaaatgt gtgatgaaaa    1440
tggtctgtgc taacaaggaa gaaaaggtgg ttgggatcca tatgcaggga cttgggtgtg    1500
atgaaatgct gcagggtttt gctgttgcag tgaagatggg agcaacgaag gcagactttg    1560
acaacacagt cgccattcac cctacctctt cagaagagct ggtcacactt cgttgagaac    1620
caggagacac gtgtggcggg cagtgggacc catagatctt ctgaaatgaa acaaataatc    1680
acattgactt actgtttgag ttttatgtat ttctttattt taatcaggat cttctgatag    1740
tggaaatttt tagtacataa tagaactttat ttatggagtt agaaatttgt agtgttatcc    1800
aggattgatt ttcatttgat cacatctcac agtaattaat attttcaagt ttttttttta    1860
ttaacagctc tgtgctagtt ttttttttct gttttagcct catcccaaat ataaagcttt    1920
gtgaagtaca attaacttaa tgtacttgaa tgaatagaac ttgctacttt ttttttttt     1980 tttttgaga cagagttttg ctctcattgc ccaggctgga gtgcggtggt gctatttcag    2040
ctcaccacaa cctctgcctc ctgggttcaa gtgattctcc tgccttagcc tcccgaatag    2100
ctggaattac aggcacgcac caccatgcct gactaatttt gtatttttag tagacatggg    2160
gtttctccat gttggtcagg ctggtctcaa actcccacct tcaggtgatc cgcccacctc    2220
ggcctcctga ggtgctgaga ttacaggcgt gagccactgt gccagcttgc taattttcac    2280
agaagttgat ggcaattctt cacatgtaaa cagtgccagt gcacagaacc tttatatatt    2340
ttttgaagcc agtactgtgc tctgcatata acaaagctgc ttcaaggatg agaccttttt    2400
ctaaaagcat gtaatgtgag aagccggcct gccttatttt ctttttttctt ttttaatgat    2460 taaaaatagt ttgtggcaag gcacggtggc tcaggcctgt aattctagca ctttgggagg    2520
ccgaggcagg aggattactt gagcctacaa gtttgaggcc agcatgcaca gcatagcaag    2580
actgcatctc tacagagagt aaaaaaaatt acccgagtgt ggtgatgtgc atctgtaatc    2640
tcagctactt gggaggctga ggtgagagga tcacttgagc ttgggtgagg tgaggctgca    2700
gtgagtcctg atcatgctgc tgcactcaat cttggacaac agagcaagac cctgtctcaa    2760
aaaaaaaaaa aaaaaatata tatatatata tatattattt ttatgaggtg aagtgcatca    2820
aacttgggaa agatttgagg aggctgggaa cctcctggaa aaccactcct tgaagaaaga    2880
tatgagagac atttagaagt gattcctgct ttcagaagga ggtggattca aatacatcaa    2940
aagtcccttc ctctgctaag tgtttatagt tcaatgaata atttcaatat ttgtatgtgt    3000
tcttgtcatt ttatttttttt ctgaaaaact tccaaaaatt tgaaataaa attacagcct    3060 tttcttctta taaaaaaaaa aaaaaa                                         3087
```

<210> SEQ ID NO 78
<211> LENGTH: 3014
<212> TYPE: DNA
<213> ORGANISM: Homo sapiens

<400> SEQUENCE: 78

```
tcctcctggg tcttgcctag cggcgggcgc atgcttagtc accgtgaggc tgcgcttgcc      60
cggggcccgc gccccctac cccggggacc gccccgggc cgcccgcccc acttggcgcg      120
ccacttccgc gtgcatggcc ctgctgcccc gagccctgag cgccggcgcg ggaccgagct     180
ggcggcgggg ggcgcgcgcc ttccgaggct tcctgctgct tctgcccgag cccgcggccc     240
tcacgcgcgc cctctcccgt gccatggcct gcaggcagga gccgcagccg cagggcccgc     300
```

| | |
|---|---|
| cgcccgctgc tggcgccgtg gcctcctatg actacctggt gatcggggc ggctcgggcg | 360 |
| ggctggccag cgcgcgcagg gcggccgagc tgggtgccag ggccgccgtg gtggagagcc | 420 |
| acaagctggg tggcacttgc gtgaatgttg gatgtgtacc caaaaaggta atgtggaaca | 480 |
| cagctgtcca ctctgaattc atgcatgatc atgctgatta tggctttcca agttgtgagg | 540 |
| gtaaattcaa ttggcgtgtt attaaggaaa agcgggatgc ctatgtgagc cgcctgaatg | 600 |
| ccatctatca aaacaatctc accaagtccc atatagaaat catccgtggc catgcagcct | 660 |
| tcacgagtga tcccaagccc acaatagagg tcagtgggaa aaagtacacc gccccacaca | 720 |
| tcctgatcgc cacaggtggt atgccctcca cccctcatga gagccagatc cccggtgcca | 780 |
| gcttaggaat aaccagcgat ggattttttc agctggaaga attgcccggc cgcagcgtca | 840 |
| ttgttggtgc aggttacatt gctgtggaga tggcagggat cctgtcagcc ctgggttcta | 900 |
| agacatcact gatgatacgg catgataagg tacttagaag ttttgattca atgatcagca | 960 |
| ccaactgcac ggaggagctg gagaacgctg gcgtggaggt gctgaagttc tcccagggga | 1020 |
| ttcaaaccga tgacaagggt catatcatcg tagacgaatt ccagaatacc aacgtcaaag | 1080 |
| gcatctatgc agttggggat gtatgtggaa aagctcttct tactccagtt gcaatagctg | 1140 |
| ctggccgaaa acttgcccat cgactttttg aatataagga agattccaaa ttagattata | 1200 |
| acaacatccc aactgtggtc ttcagccacc ccctattgg gacagtggga ctcacggaag | 1260 |
| ataagccatt cataaatatg gaatagaaaa tgtgaagacc tattcaacga ctttaccccc | 1320 |
| gatgtatcac gcagttacca aaaggaaaac aaaatgtgtg atgaaaatgg tctgtgctaa | 1380 |
| caaggaagaa aaggtggttg ggatccatat gcagggactt gggtgtgatg aaatgctgca | 1440 |
| gggttttgct gttgcagtga agatgggagc aacgaaggca gactttgaca acacagtcgc | 1500 |
| cattcaccct acctcttcag aagagctggt cacacttcgt tgagaaccag gagacacgtg | 1560 |
| tggcgggcag tgggacccat agatcttctg aaatgaaaca ataatcaca ttgacttact | 1620 |
| gtttgagttt tatgtatttc tttattttaa tcaggatctt ctgatagtgg aaattttag | 1680 |
| tacataatag aacttattta tggagttaga aatttgtagt gttatccagg attgattttc | 1740 |
| atttgatcac atctcacagt aattaatatt ttcaagtttt tttttttatta acagctctgt | 1800 |
| gctagttttt tttttctgtt ttagcctcat cccaaatata aagctttgtg aagtacaatt | 1860 |
| aacttaatgt acttgaatga atagaacttg ctactttttt ttttttttttt tttgagacag | 1920 |
| agttttgctc tcattgccca ggctggagtg cggtggtgct atttcagctc accacaacct | 1980 |
| ctgcctcctg ggttcaagtg attctcctgc cttagcctcc cgaatagctg gaattacagg | 2040 |
| cacgcaccac catgcctgac taattttgta ttttagtag acatggggtt tctccatgtt | 2100 |
| ggtcaggctg gtctcaaact cccaccttca ggtgatccgc ccacctcggc ctcctgaggt | 2160 |
| gctgagatta caggcgtgag ccactgtgcc agcttgctaa ttttcacaga agttgatggc | 2220 |
| aattcttcac atgtaaacag tgccagtgca cagaaccttt atatattttt tgaagccagt | 2280 |
| actgtgctct gcatataaca aagctgcttc aaggatgaga ccttttttcta aaagcatgta | 2340 |
| atgtgagaag ccggcctgcc ttattttctt ttttctttttt taatgattaa aaatagtttg | 2400 |
| tggcaaggca cggtggctca ggcctgtaat tctagcactt tgggaggccg aggcaggagg | 2460 |
| attacttgag cctacaagtt tgaggccagc atgcacagca tagcaagact gcatctctac | 2520 |
| agagagtaaa aaaaattacc cgagtgtggt gatgtgcatc tgtaatctca gctacttggg | 2580 |
| aggctgaggt gagaggatca cttgagcttg ggtgaggtga ggctgcagtg agtcctgatc | 2640 |
| atgctgctgc actcaatctt ggacaacaga gcaagaccct gtctcaaaaa aaaaaaaaaa | 2700 |

| | |
|---|---|
| aaatatatat atatatatat attatttta tgaggtgaag tgcatcaaac ttgggaaaga | 2760 |
| tttgaggagg ctgggaacct cctggaaaac cactccttga agaaagatat gagagacatt | 2820 |
| tagaagtgat tcctgctttc agaaggaggt ggattcaaat acatcaaaag tcccttcctc | 2880 |
| tgctaagtgt ttatagttca atgaataatt tcaatatttg tatgtgttct tgtcatttta | 2940 |
| ttttttctg aaaaacttcc aaaaatttga aaataaaatt acagcctttt cttcttataa | 3000 |
| aaaaaaaaaa aaaa | 3014 |

<210> SEQ ID NO 79
<211> LENGTH: 2928
<212> TYPE: DNA
<213> ORGANISM: Homo sapiens

<400> SEQUENCE: 79

| | |
|---|---|
| tcctcctggg tcttgcctag cggcgggcgc atgcttagtc accgtgaggc tgcgcttgcc | 60 |
| cggggcccgc gccccctac cccgggacc gccccgggc cgcccgcccc acttggcgcg | 120 |
| ccacttccgc gtgcatggcc ctgctgcccc gagccctgag cgccggcgcg ggaccgagct | 180 |
| ggcggcgggg ggcgcgcgcc ttccgaggct cctgctgct tctgcccgag cccgcggccc | 240 |
| tcacgcgcgc cctctcccgt gccatggcct gcaggcagga gccgcagccg cagggcccgc | 300 |
| cgcccgctgc tggcgccgtg gcctcctatg actacctggt gatcggggc ggctcgggcg | 360 |
| ggctggccag cgcgcgcagg gcggccgagc tgggtgccag ggccgccgtg gtggagagcc | 420 |
| acaagctggg tggcacttgc gtgaatgttg gatgtgtacc caaaaaggta atgtggaaca | 480 |
| cagctgtcca ctctgaattc atgcatgatc atgctgatta tggcttttcca agttgtgagg | 540 |
| gtaaattcaa ttggcgtgtt attaaggaaa agcgggatgc ctatgtgagc cgcctgaatg | 600 |
| ccatctatca aaacaatctc accaagtccc atatagaaat catccgtggc catgcagcct | 660 |
| tcacgagtga tcccaagccc acaatagagg tcagtgggaa aaagtacacc gccccacaca | 720 |
| tcctgatcgc cacaggtggt atgccctcca cccctcatga gagccagatc cccggtgcca | 780 |
| gcttaggaat aaccagcgat ggattttttc agctggaaga attgcccggc cgcagcgtca | 840 |
| ttgttggtgc aggttacatt gctgtggaga tggcagggat cctgtcagcc ctgggttcta | 900 |
| agacatcact gatgatacgg catgataagg ggattcaaac cgatgacaag ggtcatatca | 960 |
| tcgtagacga attccagaat accaacgtca aaggcatcta tgcagttggg gatgtatgtg | 1020 |
| gaaaagctct tcttactcca gttgcaatag ctgctggccg aaaacttgcc catcgacttt | 1080 |
| ttgaatataa ggaagattcc aaattagatt ataacaacat cccaactgtg gtcttcagcc | 1140 |
| acccccctat tgggacagtg ggactcacgg aagatgaagc cattcataaa tatggaatag | 1200 |
| aaaatgtgaa gacctattca acgagcttta ccccgatgta tcacgcagtt accaaaagga | 1260 |
| aaacaaaatg tgtgatgaaa atggtctgtg ctaacaagga agaaaggtg gttgggatcc | 1320 |
| atatgcaggg acttggtgt gatgaaatgc tgcagggttt tgctgttgca gtgaagatgg | 1380 |
| gagcaacgaa ggcagacttt gacaacacag tcgccattca ccctacctct tcagaagagc | 1440 |
| tggtcacact tcgttgagaa ccaggagaca cgtgtggcgg gcagtgggac ccatagatct | 1500 |
| tctgaaatga aacaaataat cacattgact tactgtttga gttttatgta tttcttattt | 1560 |
| ttaatcagga tcttctgata gtggaaattt ttagtacata atagaactta tttatggagt | 1620 |
| tagaaatttg tagtgttatc caggattgat tttcatttga tcacatctca cagtaattaa | 1680 |
| tatttcaag tttttttttt attaacagct ctgtgctagt ttttttttc tgttttagcc | 1740 |

```
tcatcccaaa tataaagctt tgtgaagtac aattaactta atgtacttga atgaatagaa    1800
cttgctactt ttttttttt ttttttgag acagagtttt gctctcattg cccaggctgg      1860
agtgcggtgg tgctatttca gctcaccaca acctctgcct cctgggttca agtgattctc   1920
ctgccttagc ctcccgaata gctggaatta caggcacgca ccaccatgcc tgactaattt   1980 tgtatttta gtagacatgg ggtttctcca tgttggtcag gctggtctca aactcccacc    2040
ttcaggtgat ccgcccacct cggcctcctg aggtgctgag attacaggcg tgagccactg   2100
tgccagcttg ctaattttca cagaagttga tggcaattct tcacatgtaa acagtgccag   2160
tgcacagaac ctttatatat tttttgaagc cagtactgtg ctctgcatat aacaaagctg   2220
cttcaaggat gagacctttt tctaaaagca tgtaatgtga aagccggcc tgccttattt    2280 tcttttttct tttttaatga ttaaaaatag tttgtggcaa ggcacggtgg ctcaggcctg   2340
taattctagc actttgggag gccgaggcag gaggattact tgagcctaca agtttgaggc   2400
cagcatgcac agcatagcaa gactgcatct ctacagagag taaaaaaat tacccgagtg    2460 tggtgatgtg catctgtaat ctcagctact tgggaggctg aggtgagagg atcacttgag   2520
cttgggtgag gtgaggctgc agtgagtcct gatcatgctg ctgcactcaa tcttggacaa   2580
cagagcaaga ccctgtctca aaaaaaaaaa aaaaaatat atatatatat atatattatt    2640
tttatgaggt gaagtgcatc aaacttggga aagatttgag gaggctggga acctcctgga   2700
aaaccactcc ttgaagaaag atatgagaga catttagaag tgattcctgc tttcagaagg   2760
aggtggattc aaatacatca aaagtcccctt cctctgctaa gtgtttatag ttcaatgaat  2820
aatttcaata tttgtatgtg ttcttgtcat tttattttt tctgaaaaac ttccaaaaat    2880
ttgaaaataa aattacagcc ttttcttctt ataaaaaaaa aaaaaaaa                 2928

<210> SEQ ID NO 80
<211> LENGTH: 1093
<212> TYPE: DNA
<213> ORGANISM: Homo sapiens

<400> SEQUENCE: 80
attgcattcc tgggcattgc taactagtga agtataccag atggaaatgt cttcgaagct     60 gtcccttaa aactcgagca agctaccagg caaactccgc ctccagggag gttccttatt     120
aaataggagc caactggctg ggtcggggct caataccca agcaataccT gcaactgagg     180
attcttcccg gggagaccgc agcccatcgg catggctcaa gagtttgtga actgcaaaat    240
ccagcctggg aaggtggttg tgttcatcaa gcccacctgc ccgtactgca ggagggccca    300
agagatcctc agtcaattgc ccatcaaaca agggcttctg gaatttgtcg atatcacagc    360
caccaaccac actaacgaga ttcaagatta tttgcaacag ctcacgggag caagaacggt    420
gcctcgagtc tttattggta aagattgtat aggcggatgc agtgatctag tctctttgca    480
acagagtggg gaactgctga cgcggctaaa gcagattgga gctctgcagt aaccacagat    540
ctcataggaa atgttcaaca attctgtgaa aggtcacagg acccaattgg agaaatcata    600
tgaaaagcat agttggtctt ggtgtcatat ggatcagagg cacaagtgca gaggctgtgg    660
tcatgcggaa cactctgtta tttaagatgg ctatccagat aatcctgaac actgtgtatt    720 tatttattt agactaccag caaagattaa agcatgaaat gtaaacatc tgataaaact      780 tacagccccc tacaccaaga gtgtatctgt gaaagagctc ctacactttg aaaacttaag    840
aatcccttat catgaagtttt gcctgttcta gaattgtaag attgttaatt tccttcaatc   900
tctagtgaca acacttaatt tcttttctaa taaaaaaac ctatagatga ttcagtgatt    960
```

```
tttgtccaat tcatttgcat gttctcaaga cattaaggaa tgttatgcga aatacactaa    1020
cttaaaactg tgtttatatt tggccctgcc attataaata aagacacgtg ctgctgtcaa    1080
aaaaaaaaaa aaa                                                       1093

<210> SEQ ID NO 81
<211> LENGTH: 827
<212> TYPE: DNA
<213> ORGANISM: Homo sapiens

<400> SEQUENCE: 81
gcagtggagg cggcccaggc ccgccttccg cagggtgtcg ccgctgtgcc gctagcggtg      60
ccccgcctgc tgcggtggca ccagccagga ggcggagtgg aagtggccgt ggggcgggta     120
tgggactagc tggcgtgtgc gccctgagac gctcagcggg ctatatactc gtcggtgggg     180
ccggcggtca gtctgcggca gcggcagcaa gacggtgcag tgaaggagag tgggcgtctg     240
gcggggtccg cagtttcagc agagccgctg cagccatggc cccaatcaag gtgggagatg     300
ccatcccagc agtggaggtg tttgaagggg agccagggaa caaggtgaac ctggcagagc     360
tgttcaaggg caagaagggt gtgctgtttg gagttcctgg ggccttcacc cctggatgtt     420
ccaaggttcg gctcctggct gatcccactg gggcctttgg gaaggagaca gacttattac     480
tagatgattc gctggtgtcc atctttggga atcgacgtct caagaggttc tccatggtgg     540
tacaggatgg catagtgaag gccctgaatg tggaaccaga tggcacaggc ctcacctgca     600
gcctggcacc caatatcatc tcacagctct gaggccctgg gccagattac ttcctccacc     660
cctccctatc tcacctgccc agccctgtgc tggggccctg caattggaat gttggccaga     720
tttctgcaat aaaacacttgt ggtttgcggc caaaaaaaaa aaaaaaaaaa aaaaaaaaa     780 aaaaaaaaaa aaaaaaaaaa aaaaaaaaaa aaaaaaaaaa aaaaaa                    827

<210> SEQ ID NO 82
<211> LENGTH: 692
<212> TYPE: DNA
<213> ORGANISM: Homo sapiens

<400> SEQUENCE: 82
gcagtggagg cggcccaggc ccgccttccg cagggtgtcg ccgctgtgcc gctagcggtg      60
ccccgcctgc tgcggtggca ccagccagga ggcggagtgg aagtggccgt ggggcgggta     120
tgggactagc tggcgtgtgc gccctgagac gctcagcggg ctatatactc gtcggtgggg     180
ccggcggtca gtctgcggca gcggcagcaa gacggtgcag tgaaggagag tgggcgtctg     240
gcggggtccg cagtttcagc agagccgctg cagccatggc cccaatcaag gttcggctcc     300
tggctgatcc cactggggcc tttgggaagg agacagactt attactagat gattcgctgg     360
tgtccatctt tgggaatcga cgtctcaaga ggttctccat ggtggtacag gatggcatag     420
tgaaggccct gaatgtggaa ccagatggca caggcctcac ctgcagcctg cacccaata     480 tcatctcaca gctctgaggc cctgggccag attacttcct ccacccctcc ctatctcacc     540
tgcccagccc tgtgctgggg ccctgcaatt ggaatgttgg ccagatttct gcaataaaca     600
cttgtggttt gcggccaaaa aaaaaaaaaa aaaaaaaaaa aaaaaaaaaa aaaaaaaaaa     660
aaaaaaaaaa aaaaaaaaaa aaaaaaaaaa aa                                   692

<210> SEQ ID NO 83
<211> LENGTH: 1537
<212> TYPE: DNA
```

<213> ORGANISM: Homo sapiens

<400> SEQUENCE: 83

| | | | | | |
|---|---|---|---|---|---|
| ccctgcgtct | ctgcccgccc | cgtggcgccc | gagtgcactg | aagatggcgg | ctgctgtagg | 60 |
| acggttgctc | cgagcgtcgg | ttgcccgaca | tgtgagtgcc | attccttggg | gcatttctgc | 120 |
| cactgcagcc | ctcaggcctg | ctgcatgtgg | aagaacgagc | ttgacaaatt | tattgtgttc | 180 |
| tggttccagt | caagcaccct | attttaaggg | tacagccgtt | gtcaatggag | agttcaaaga | 240 |
| cctaagcctt | gatgacttta | aggggaaata | tttggtgctt | ttcttctatc | ctttggattt | 300 |
| cacctttgtg | tgtcctacag | aaattgttgc | ttttagtgac | aaagctaacg | aatttcacga | 360 |
| cgtgaactgt | gaagttgtcg | cagtctcagt | ggattcccac | tttagccatc | ttgcctggat | 420 |
| aaatacacca | aggaagaatg | gtggtttggg | ccacatgaac | atcgcactct | tgtcagactt | 480 |
| aactaagcag | atttcccgag | actacggtgt | gctgttagaa | ggttctggtc | ttgcactaag | 540 |
| aggtctcttc | ataattgacc | ccaatggagt | catcaagcat | ttgagcgtca | acgatctccc | 600 |
| agtgggccga | agcgtggaag | aaaccctccg | cttggtgaag | gcgttccagt | atgtagaaac | 660 |
| acatggagaa | gtctgcccag | cgaactggac | accggattct | cctacgatca | agccaagtcc | 720 |
| agctgcttcc | aaagagtact | ttcagaaggt | aaatcagtag | atcacccatg | tgtatctgca | 780 |
| ccttctcaac | tgagagaaga | accacagttg | aaacctgctt | ttatcatttt | caagatggtt | 840 |
| atttgtagaa | ggcaaggaac | caattatgct | tgtattcata | agtattactc | taaatgtttt | 900 |
| gtttttgtaa | ttctggctaa | gaccttttaa | acatggttag | ttgctagtac | aaggaatcct | 960 |
| ttattggtaa | catcttggtg | gctggctagc | tagtttctac | agaacataat | ttgcctctat | 1020 |
| agaaggctat | tcttagatca | tgtctcaatg | gaaacactct | tctttcttag | ccttacttga | 1080 |
| atcttgccta | taataaagta | gagcaacaca | cattgaaagc | ttctgatcaa | cggtcctgaa | 1140 |
| attttcatct | tgaatgtctt | tgtattaaac | tgaattttct | tttaagctaa | caaagatcat | 1200 |
| aattttcaat | gattagccgt | gtaactcctg | caatgaatgt | ttatgtgatt | gaagcaaatg | 1260 |
| tgaatcgtat | tattttaaaa | agtggcagag | tgacttaact | gatcatgcat | gatccctcat | 1320 |
| ccctgaaatt | gagtttatgt | agtcatttta | cttattttat | tcattagcta | actttgtcta | 1380 |
| tgtatatttc | tagatattga | ttagtgtaat | cgattataaa | ggatatttat | caaatccagg | 1440 |
| gattgcattt | tgaaattata | attatttttct | ttgctgaagt | attcattgta | aaacatacaa | 1500 |
| aataaacata | ttttaaaaca | tttgcatttt | accacca | | | 1537 |

<210> SEQ ID NO 84
<211> LENGTH: 964
<212> TYPE: DNA
<213> ORGANISM: Homo sapiens

<400> SEQUENCE: 84

| | | | | | |
|---|---|---|---|---|---|
| gagcgctctg | gagggcgtgg | ccgtgggaaa | ggaggcgcgg | aaagccgacg | cgcgtccatt | 60 |
| ggtcggctgg | acgaggggag | gagccgctgg | ctcccagccc | cgccgcgatg | agcctcggcc | 120 |
| gcctttgccg | cctactgaag | ccggcgctgc | tctgtggggc | tctggccgcg | cctggcctgg | 180 |
| ccgggaccat | gtgcgcgtcc | cggacgact | ggcgctgtgc | gcgctccatg | cacgagtttt | 240 |
| ccgccaagga | catcgacggg | cacatggtta | acctggacaa | gtaccggggc | ttcgtgtgca | 300 |
| tcgtcaccaa | cgtggcctcc | cagtgaggca | agaccgaagt | aaactacact | cagctcgtcg | 360 |
| acctgcacgc | ccgatacgct | gagtgtggtt | tgcggatcct | ggccttcccg | tgtaaccagt | 420 |
| tcgggaagca | ggagccaggg | agtaacgaag | agatcaaaga | gttcgccgcg | ggctacaacg | 480 |

-continued

```
tcaaattcga tatgttcagc aagatctgcg tgaacgggga cgacgcccac ccgctgtgga    540
agtggatgaa gatccaaccc aagggcaagg gcatcctggg aaatgccatc aagtggaact    600
tcaccaagtt tggacaccgt ctctccacag ttcctcatcg acaagaacgg ctgcgtggtg    660
aagcgctacg gacccatgga ggagcccctg gtgatagaga aggacctgcc ccactatttc    720
tagctccaca agtgtgtggc cccgcccgag cccctgccca cgcccttgga gccttccacc    780
ggcactcatg acgcctgcc tgcaaacctg ctggtggggc agacccgaaa atccagcgtg    840
caccccgccg gaggaaggtc ccatggcctg ctgggcttgg ctcggcgccc ccaccctgg    900 ctaccttgtg ggaataaaca gacaaattag cctgctggaa aaaaaaaaa aaaaaaaaa    960 aaaa                                                                964
```

<210> SEQ ID NO 85
<211> LENGTH: 1031
<212> TYPE: DNA
<213> ORGANISM: Homo sapiens

<400> SEQUENCE: 85

```
agtcctgact acggcctccg ggccctttgt ccccgctagc ggcgctcggg gtggggagc    60 caggagggc gggagacggg cgggtatggg ccgcgcgggc gcaggctccc ccgggcgccg    120
caggcagcgg tgccagagcc ggggcaggcg gcggccgcga gccctcggc ggcggaaggc    180 cccagcgtgc aggcgcagga gggcgcggcg ccggcggaag aagccctgtc cccgcagctt    240
gcgaccggag atccacgaat gtcccaagtc ccaggacccg tgcgcgtccc gggacgactg    300
gcgctgtgcg cgctccatgc acgagttttc cgccaaggac atcgacgggc acatggttaa    360
cctggacaag taccgggct tcgtgtgcat cgtcaccaac gtggcctccc agtgaggcaa    420
gaccgaagta aactacactc agctcgtcga cctgcacgcc cgatacgctg agtgtggttt    480
gcggatcctg gccttcccgt gtaaccagtt cgggaagcag gagccaggga gtaacgaaga    540
gatcaaagag ttcgccgcgg gctacaacgt caaattcgat atgttcagca agatctgcgt    600
gaacggggac gacgcccacc cgctgtggaa gtggatgaag atccaaccca agggcaaggg    660
catcctggga aatgccatca gtggaactt caccaagttc ctcatcgaca agaacggctg    720
cgtggtgaag cgctacggac ccatggagga gcccctggtg atagagaagg acctgcccca    780
ctatttctag ctccacaagt gtgtggcccc gcccgagccc ctgccacgc ccttggagcc    840 ttccaccggc actcatgacg gcctgcctgc aaacctgctg gtggggcaga cccgaaaatc    900
cagcgtgcac cccgccggag gaaggtccca tggcctgctg ggcttggctc ggcgccccca    960
cccctggcta ccttgtggga ataaacagac aaattagcct gctggaaaaa aaaaaaaaaa    1020 aaaaaaaaa a                                                         1031
```

METHOD FOR DIAGNOSING HEMATOLOGICAL DISORDERS

The present invention relates to a method for diagnosing hematological disorders in a patient.

The great quantity of hematopoietic cells and the many stages of differentiation through which they pass further complicate the classification of the neoplasis originating from this type of cells. Despite the efforts to establish a classification based on "real" entities, some of the categories are ambiguous and in many cases contain very heterogeneous groups as regards a response to therapy of clinical course. This heterogeneity is that responsible for, on the one hand, the incessant search for markers capable of differentiating some behaviours from others and, on the other hand, that the disputed classification of this type of neoplasia is subjected to continuous revisions.

An ideal classification system should be precise, reproducible, easy to use and should especially have biological and clinical significance (Chan W C et al., *Croat Med J.* 2005; 46:349-59). The current diagnosis systems and the classification of the hematological neoplasias are based on the recognition of histological and morphological, immunophenotypical and cytogenetic characteristics and study of a molecular marker with prognostic value. However, in some of the diagnostic categories defined in this way, the following is observed:

A marked heterogeneous therapy response: within the same disease, patients either reach full remission, or partial remission, or do not respond, or relapse after a certain therapy. The capacity to predict a response is especially important in this type of neoplasias since the transplant of stem cells is an effective but toxic alternative response. The capacity to determine which patients would respond to a conventional therapy before giving it may be beneficial to be able to apply the most effective treatment to each patient.

A variable clinical behaviour: within this category for some patients the disease is going to remain stable for long periods of time and that are not going to need therapy and whereas for others the disease is going to progress rapidly requiring aggressive therapy.

These variations point to the existence of molecular heterogeneity within the diagnostic categories, differences which the conventional methods of diagnosis are not capable of determining and hence, the search for new forms of analysis which provide a greater resolution in the characterization of this type of neoplasias.

In this line, the use of expression arrays have demonstrated being effective not only in deciphering the biological and clinical diversity which is found in many tumours, but in understanding the biological and pathological processes which affect many symptoms and, in particular, the hematopoietic system. The expression arrays are ordered arrays of sequences associated to a solid support, complementary to mRNA or to its corresponding cDNA or cRNA, which allow the analysis of the differential expression of hundreds or thousands of genes simultaneously. One of the supports to which they are frequently bound is to rectangular fragments of glass similar to slides, a format which is frequently alluded to by the terms microarray, biochip or, simply, chip. Their use is becoming increasingly frequent for the diagnosis of various diseases or for the evolution of the evaluation of the susceptibility of suffering from them.

In 1999, the Golub group published one of the first articles referring to the role of arrays in the classification of hematological neoplasias (Golub T R et al., *Science.* 1999; 286:531-7). An array with 6817 genes represented was used for the study of expression profiles in acute myeloid leukemia (AML) and acute lymphoid leukemia (ALL). A group of 50 genes was selected with the capacity of predicting the type of leukemia (class predictor) and they were used to classify a group of unknown samples in the correct categories. The study of the expression of these 50 genes is sufficient for the classification of a sample of AML or ALL. Despite the fact that the distinction between AML and ALL is well established with the current diagnostic methods, the study revealed the existence of specific expression patterns associated with each type of acute leukemia and proved the use.

The European patent application EP1947194 has proposed the use of specific oligonucleotides for diagnosing chronic lymphoid leukemia (CLL) diseases.

The international application WO 2005/080601 discloses methods of genetic analysis for the classification, diagnosis and prognosis of acute myeloid leukemia (AML). This application provides a method for differentiating AML subtypes, but never provides methods for the discrimination between preleukemic and leukemic states.

The international application WO 2006/125195 discloses a group of 24 genes whose expression allows to classify a sample as myelodysplastic syndrome (MDS), AML, or not diseased. However, this document does not provide a method for classifying different grade of MDS.

So there is a need to provide a new method for diagnosing, classifying the malignant and premalignant states of cancer.

Oxidative stress is generally defined as an imbalance between the generation of reactive oxygen species (ROS) and impaired antioxidant defence systems. It has long been known to be involved in the pathophysiology of cancer.

High level of ROS produced either endogenously or exogenously can attack lipids, proteins, and nucleic acids simultaneously in living cells. This has led to cells developing various antioxidant defense mechanisms to both prevent the excessive formation of ROS and limit their harmful effects. The appropriate redox balance is maintained via the combined action of antioxidant enzymes.

Myelodysplastic syndroma and acute leukemia are characterized by a pathological hematopoieisis. ROS certainly plays an important role in human hematopoiesis. For example, it is well established in murine models that ROS-induced p38 MAPK activation is crucial in hematopoiesis and increased ROS levels are required to trigger hematopoietic stem cells (HSC) exit from quiescence and to drive maturation and differentiation. Moreover, a high ROS level induces a perturbation in the self-renewal activity of HSC. It is now well established that the progression of normal cells to neoplastic transformation results from the accumulation of mutations in genes that control cellular proliferation, survival, and differentiation. Approximately, 30% myelodysplastic syndroma cases progress to acute leukemia. Indirect evidences suggest a role for oxidant DNA damage in the pathogenesis of myelodysplasia. Moreover, the flow cytometric quantification of ROS in bone marrow cells from myelodysplastic and leukemic patients reveals an increase in ROS level in all cases.

So, studying the antioxidant response in premalignant and malignant state seems to be a good start for providing a new useful method.

The cancer stem cell (CSC) hypothesis suggests that a subset of cells within a tumor has the ability to recapitulate the generation of a continuously growing tumor (Clarke M F et al., *Cancer Research.* 2006; 66: 9339-44). CSCs are best described in human in which the rare so-called leukemia stem cells (L-HSCs) can be prospectively isolated and shown to transmit the disease when introduced into immuno-compromised mice (Lapdot T et al., *Nature*. 1994; 645-8). Cells which do not share this phenotype often represent the bulk of the leukemic clone, but fail to transmit the disease upon transplantation. The early work on L-HSC has now been extended to a list of tumors which is rapidly expanding (Bomken S, *Br. J. Cancer* 2010; 103:439-45). Because they appear to be resistant to drugs that are commonly used to treat leukemia in humans, L-HSCs may be responsible for relapse in some patients (Ishikawa F, *Nat. Biotechnol* 2007; 25:1315-21). Genes which are functionally significant for L-HSC expansion may therefore represent the ultimate therapeutic targets. This raises the possibility that other ROS scavenging systems are of regulatory importance in other cancer stem cells. Indeed a low ROS level in breast CSCs has recently been reported, where it was associated with increased expression of the glutathione biosynthesis genes (Diehn M, *Nature*. 2009; 458:780-3).

Therefore, one aim of the invention is to provide a new method for diagnosing cancer.

Another aim of the invention is to provide a rapid efficient method for classifying pathologic sample, which cannot be classified by other method.

Another aim of the invention is to provide a kit for the implementation of the above methods.

Another aim of the invention is to provide composition allowing the implementation of the above method.

The invention relates to a method for the diagnosis, and/or the classification, preferably in vitro, of an hematological disorder, in particular myeloid and/or lymphoid hematological disorder, preferably myeloid hematological disorder, said method comprising the steps of:

a). measuring, from cells contained in a biological sample of a subject, preferably from blood cells or bone marrow cells containing sample, the expression level of at least the genes of a sub-group of 6 genes belonging to a set of genes chosen among a group of 24 genes, said group of 24 genes comprising or being constituted by the nucleic acid sequences SEQ ID NO:1 to 24, wherein said subject is suspected to be afflicted by an hematological disorder, in particular myeloid and/or lymphoid hematological disorder, preferably myeloid hematological disorder, said 6 genes belonging to said sub-group comprising or being constituted by the nucleic acid sequences SEQ ID NO: 1 to 6, b). comparing the expression level of each genes measured in step a)., with the expression level of the same respective genes from cells contained in a control sample preferably from blood cells or bone marrow cells containing sample, said control sample being of the same nature than said biological sample, to establish a gene expression level ratio for each genes of said sub-group, and c). determining the status of said biological sample such that if the ratio established in step b). for each genes of any combination of at least 3 genes from said sub-group is either ≥2 or ≤0.5, said biological sample is representative of an hematological disorder cells.

In other words, the step b). according to the invention consists of:

comparing the expression level of each genes measured in step a)., with the expression level of the same respective genes from cells contained in a control sample, preferably from a control sample containing blood cells or bone marrow cells, said control sample being of the same nature than said biological sample, to establish a gene expression level ratio $R_i$ between the expression level of each genes i measured in step a) and the expression level of the same respective genes i from cells contained in a control sample, for each genes of said sub-group.

The step c). according to the invention consists of determining the status of said biological sample such that if the ratio $R_i$ for each genes of any combination of 3 genes from said sub-group is either ≥2, or ≤0.5, said biological sample is representative of an haematological disorder cells.

The invention is based on the unexpected observation made by the Inventors that at least 6 specific genes, i.e. the genes comprising or being constituted by the nucleic acid sequences SEQ ID NO 1-6, belonging to a group of 24 specific genes comprising or being constituted by the nucleic acid sequences SEQ ID NO 1-24 are sufficient to determine the status a of an hematological disorder.

The invention is preferably carried out with sample from patients who have not been previously treated for an hematological disorder.

These genes are specifically genes coding for enzymes involved in the detoxification of cells, in which ROS accumulate.

The natural process involved in the elimination of ROS is represented in FIG. 1.

According to the invention the group (C) of 24 genes comprises a set (B) of genes, said set comprising the subgroup (A) of 6 specific genes as defined above. The imbrications of the group/set/subgroup according to the invention are represented in FIG. 2.

The method according to the invention is thus carried out as follows:

from a sample of a patient, the nucleic acid molecules contained in said sample are extracted, preferably the RNA molecules, according to extraction methods known in the art, the amount of specific nucleic acid molecules, corresponding to the nucleic acid molecules comprising or being constituted by at least SEQ ID NO: 1-6, is quantified, by well known techniques as illustrated hereafter, the amount quantified in the above step is compared with the amount of the same nucleic acid molecules contained in a control sample, and a ratio is established.

Accordingly, the control sample, which is used as reference, is a sample of an healthy individual, said healthy sample being of the same nature than the sample of the patient. Advantageously, the control sample corresponds to a pool of numerous samples of different healthy individuals, i.e. the control sample represents the mean of numerous healthy individual.

As mentioned above, the sample of the patient and the control sample are of the same origin. This means that if the sample of the patient is originated from blood of the patient, the control sample is originated from blood of one or many healthy individuals. Blood, in the invention, means total blood, plasma, serum, peripheral blood mononuclear cells (PBMC) . . . .

In the same way, if the sample of the patient is originated from bone marrow, the control sample is originated from bone marrow of one or many healthy individuals.

In the invention, the biological of the patient, from whom the biological sample is used, is suspected to be afflicted by an hematological disorder, in particular myeloid and/or lymphoid hematological disorder, preferably myeloid hematological disorder.

This means that the pathological status of the patient is:
either undetermined (the pathologist does not know if said patient is afflicted by an hematological disorder),
or determined (the pathologist knows that the patient is afflicted by an hematological disorder).

This also means that the pathological status of the patient is:
first determined (the pathologist identify if the patient is afflicted by an hematological disorder, or not),
and if the patient is afflicted by an hematological disorder, said hematological disorder is classified.

If the pathological status is undetermined, then the pathologist measure the expression levels of the genes consisting of SEQ ID NO: 1-6 in a biological sample from said patient and compare said expression levels with the expression levels of the same genes (i.e. genes SEQ ID NO: 1-6) in a control sample of the same nature, as defined above, (for instance a pool of cells from healthy donors that is used as control sample or reference), in order to establish the ratios Ri, and to determine if the patient is afflicted by hematological disorder or not.

If the pathological status is determined (for instance by cytological studies), the pathologist measures the expression levels of the genes consisting of SEQ ID NO: 1-6 in a biological sample from said patient and compares said expression levels with the expression levels of the same genes (i.e. genes SEQ ID NO: 1-6) in a control sample of the same nature, as defined above, (for instance a pool of cells from healthy donors that is used as control sample or reference), in order to establish the ratios Ri, and can classify the hematological disorder according to the method of the invention.

The method according to the invention provides an easy to use, rapid and efficient process to evaluate the status of a sample identified as, or suspected to be, a sample corresponding to an hematological disorder, in particular a myeloid disorder.

If the ratio between the expression level of at least 3 genes, of the above 6 genes belonging to the above defined subgroup, of a patient sample and the expression level of the same at least 3 genes of a control sample is either ≥2 or ≤0.5, then the sample of the patient would be considered as presenting the features of a sample corresponding to an hematological disorder.

Above and hereafter, the ratio is defined as follows:

$Ri$=[Amount(expression level)of a gene $i$ of SEQ ID NO: $i$ in the patient sample]/[Amount(expression level)of a gene $i$ of SEQ ID NO: $i$ in the control sample]

i varying from 1 to 24.

Therefore $R_3$ represents the ratio as defined above, relative to the gene SEQ ID NO: 3, and thus $R_i$ represents the ratio as defined above, relative to the gene SEQ ID NO: i, i varying from 1 to 24.

In the invention, "the ratio $R_i$ of each gene of any combination of at least 3 genes of the 6 genes of said subgroup is ≥2 or ≤0.5" means that the ratio $R_i$ of each gene of any combination of 3, or 4 or 5 or 6 genes is ≥2 or ≤0.5.

All the 20 combinations of 3 genes chosen among the 6 genes are listed hereafter:
SEQ ID NO: 1+SEQ ID NO: 2+SEQ ID NO: 3,
SEQ ID NO: 1+SEQ ID NO: 2+SEQ ID NO: 4,
SEQ ID NO: 1+SEQ ID NO: 2+SEQ ID NO: 5,
SEQ ID NO: 1+SEQ ID NO: 2+SEQ ID NO: 6,
SEQ ID NO: 1+SEQ ID NO: 3+SEQ ID NO: 4,
SEQ ID NO: 1+SEQ ID NO: 3+SEQ ID NO: 5,
SEQ ID NO: 1+SEQ ID NO: 3+SEQ ID NO: 6,
SEQ ID NO: 1+SEQ ID NO: 4+SEQ ID NO: 5,
SEQ ID NO: 1+SEQ ID NO: 4+SEQ ID NO: 6,
SEQ ID NO: 1+SEQ ID NO: 5+SEQ ID NO: 6,
SEQ ID NO: 2+SEQ ID NO: 3+SEQ ID NO: 4,
SEQ ID NO: 2+SEQ ID NO: 3+SEQ ID NO: 5,
SEQ ID NO: 2+SEQ ID NO: 3+SEQ ID NO: 6,
SEQ ID NO: 2+SEQ ID NO: 4+SEQ ID NO: 5,
SEQ ID NO: 2+SEQ ID NO: 4+SEQ ID NO: 5,
SEQ ID NO: 2+SEQ ID NO: 5+SEQ ID NO: 6,
SEQ ID NO: 3+SEQ ID NO: 4+SEQ ID NO: 5,
SEQ ID NO: 3+SEQ ID NO: 4+SEQ ID NO: 6,
SEQ ID NO: 3+SEQ ID NO: 5+SEQ ID NO: 6 and
SEQ ID NO: 4+SEQ ID NO: 5+SEQ ID NO: 6.

All the 15 combinations of 4 genes among the 6 genes are the following ones:
SEQ ID NO: 1+SEQ ID NO: 2+SEQ ID NO: 3+SEQ ID NO: 4,
SEQ ID NO: 1+SEQ ID NO: 2+SEQ ID NO: 3+SEQ ID NO: 5,
SEQ ID NO: 1+SEQ ID NO: 2+SEQ ID NO: 3+SEQ ID NO: 6,
SEQ ID NO: 1+SEQ ID NO: 3+SEQ ID NO: 4+SEQ ID NO: 5,
SEQ ID NO: 1+SEQ ID NO: 3+SEQ ID NO: 4+SEQ ID NO: 6,
SEQ ID NO: 1+SEQ ID NO: 2+SEQ ID NO: 4+SEQ ID NO: 5,
SEQ ID NO: 1+SEQ ID NO: 2+SEQ ID NO: 4+SEQ ID NO: 6,
SEQ ID NO: 1+SEQ ID NO: 2+SEQ ID NO: 5+SEQ ID NO: 6,
SEQ ID NO: 1+SEQ ID NO: 2+SEQ ID NO: 3+SEQ ID NO: 5,
SEQ ID NO: 1+SEQ ID NO: 2+SEQ ID NO: 3+SEQ ID NO: 6,
SEQ ID NO: 2+SEQ ID NO: 3+SEQ ID NO: 4+SEQ ID NO: 5,
SEQ ID NO: 2+SEQ ID NO: 3+SEQ ID NO: 4+SEQ ID NO: 6,
SEQ ID NO: 2+SEQ ID NO: 3+SEQ ID NO: 5+SEQ ID NO: 6,
SEQ ID NO: 2+SEQ ID NO: 4+SEQ ID NO: 5+SEQ ID NO: 6 and
SEQ ID NO: 3+SEQ ID NO: 4+SEQ ID NO: 5+SEQ ID NO: 6.

All the 6 combinations of 5 genes among 6 genes are the following ones:
SEQ ID NO: 1+SEQ ID NO: 2+SEQ ID NO: 3+SEQ ID NO: 4+SEQ ID NO: 5,
SEQ ID NO: 1+SEQ ID NO: 2+SEQ ID NO: 3+SEQ ID NO: 4+SEQ ID NO: 6,
SEQ ID NO: 1+SEQ ID NO: 2+SEQ ID NO: 3+SEQ ID NO: 5+SEQ ID NO: 6,
SEQ ID NO: 1+SEQ ID NO: 2+SEQ ID NO: 4+SEQ ID NO: 5+SEQ ID NO: 6,
SEQ ID NO: 1+SEQ ID NO: 3+SEQ ID NO: 4+SEQ ID NO: 5+SEQ ID NO: 6 and SEQ ID NO: 2+SEQ ID NO: 3+SEQ ID NO: 4+SEQ ID NO: 5+SEQ ID NO: 6.

Finally, the combination of the six genes is SEQ ID NO: 1+SEQ ID NO: 2+SEQ ID NO: 3+SEQ ID NO: 4+SEQ ID NO: 5+SEQ ID NO: 6.

According to the invention, a sample of a patient wherein the ratio $R_i$ of each gene belonging to any combination of least 3 genes of the subgroup of 6 genes is ≥2 or ≤0.5 will be considered as a sample corresponding to an hematological disorder.

For instance, if the combination SEQ ID NO: 1+SEQ ID NO: 2+SEQ ID NO: 3 is studied, if the respective ratios $R_1$, $R_2$ and $R_3$ as described above are as follows:

R1≥2 and R2≥2 and R3≥2, or
R1≤0.5 and R2≥2 and R3≥2, or
R1≥2 and R2≤0.5 and R3≥2, or
R1≥2 and R2≥2 and R3≤0.5, or
R1≤0.5 and R2≤0.5 and R3≥2, or
R1≤0.5 and R2≥2 and R3≤0.5, or
R1≥2 and R2≤0.5 and R3≤0.5, or
R1≤0.5 and R2≤0.5 and R3≤0.5, then the sample of the patient in which the ratios are calculated will be considered as a sample corresponding to an hematological disorder.

The above example applies mutatis mutandis to the combinations of at least 3 genes mentioned above.

Consequently, if the combination SEQ ID NO: 1+SEQ ID NO: 2+SEQ ID NO: 3+SEQ ID NO: 4 is studied, 4 combinations of 3 genes exist:

SEQ ID NO: 1+SEQ ID NO: 2+SEQ ID NO: 3,
SEQ ID NO: 1+SEQ ID NO: 2+SEQ ID NO: 4,
SEQ ID NO: 1+SEQ ID NO: 3+SEQ ID NO: 4, and
SEQ ID NO: 2+SEQ ID NO: 3+SEQ ID NO: 4.

Therefore, if the respective ratios $R_1$, $R_2$, $R_3$ and $R_4$ are as follows:

for combination 1:
R1≥2 and R2≥2 and R3≥2, or
R1≤0.5 and R2≥2 and R3≥2, or
R1≥2 and R2≤0.5 and R3≥2, or
R1≥2 and R2≥2 and R3≤0.5, or
R1≤0.5 and R2≤0.5 and R3≥2, or
R1≤05 and R2≥2 and R3≤0.5, or
R1≥2 and R2≤0.5 and R3≤0.5, or
R1≤0.5 and R2≤0.5 and R3≤0.5,
for combination 2
R1≥2 and R3≥2 and R4≥2, or
R1≤0.5 and R3≥2 and R4≥2, or
R1≥2 and R3≤0.5 and R4≥2, or
R1≥2 and R3≥2 and R4≤0.5, or
R1≤0.5 and R3≤0.5 and R4≥2, or
R1≤0.5 and R3≥2 and R4≤0.5, or
R1≥2 and R3≤0.5 and R4≤0.5, or
R1≤0.5 and R3≤0.5 and R4≤0.5,
for combination 3,
R1≥2 and R2≥2 and R4≥2, or
R1≤0.5 and R2≥2 and R4≥2, or
R1≥2 and R2≤0.5 and R4≥2, or
R1≥2 and R2≥2 and R4≤0.5, or
R1≤0.5 and R2≤0.5 and R4≥2, or
R1≤0.5 and R2≥2 and R4≤0.5, or
R1≥2 and R2≤0.5 and R4≤0.5, or
R1≤0.5 and R2≤0.5 and R4≤0.5,
for combination 4
R2≥2 and R3≥2 and R4≥2, or
R2≤0.5 and R3≥2 and R4≥2, or
R2≥2 and R3≤0.5 and R4≥2, or
R2≥2 and R3≥2 and R4≤0.5, or
R2≤0.5 and R3≤0.5 and R4≥2, or
R2≤0.5 and R3≥2 and R4≤0.5, or
R2≥2 and R3≤0.5 and R4≤0.5, or
R2≤0.5 and R3≤0.5 and R4≤0.5, then the sample of the patient in which the ratios are calculated will be considered as a sample corresponding to an hematological disorder.

In the invention, the genes for which the expression level is measured are represented by the RNA molecules obtained by the transcription of said genes. The transcription process is well known in the art.

Therefore, the invention relates to a process as defined above, in which the expression level of the above genes is measured by determining the amount of RNA molecules that are the products of the transcription of said genes, i.e. which are the products of the expression of said genes.

Some genes in the invention are able to express many variants, i.e. many RNA molecules that differ in their sequences. Theses variants generally differ in there sequence after alternative splicing, said alternative splicing having as consequence to add, to delete and/or to modify one or more parts of the nucleic acid sequence contained in the gene in the resulting RNA molecule. The skilled person knows the mechanisms of alternative splicing.

Therefore some genes according to the invention can express more than one RNA molecule, and provide variants.

The PRDX gene is able to express 3 different variants: the first variant comprising or consisting of the nucleic acid sequence SEQ ID NO: 5, a second variant comprising or consisting of the nucleic acid sequence SEQ ID NO: 73 and a third variant comprising or consisting of the nucleic acid sequence SEQ ID NO: 74.

The SOD2 gene is able to express 3 different variants: the first variant comprising or consisting of the nucleic acid sequence SEQ ID NO: 7, a second variant comprising or consisting of the nucleic acid sequence SEQ ID NO: 75 and a third variant comprising or consisting of the nucleic acid sequence SEQ ID NO: 76.

The GSR gene is able to express 4 different variants: the first variant comprising or consisting of the nucleic acid sequence SEQ ID NO: 8, a second variant comprising or consisting of the nucleic acid sequence SEQ ID NO: 77, a third variant comprising or consisting of the nucleic acid sequence SEQ ID NO: 78 and a fourth variant comprising or consisting of the nucleic acid sequence SEQ ID NO: 79.

The GLRX gene is able to express 2 different variants: the first variant comprising or consisting of the nucleic acid sequence SEQ ID NO: 9 and a second variant comprising or consisting of the nucleic acid sequence SEQ ID NO: 80.

The PDRX5 gene is able to express 3 different variants: the first variant comprising or consisting of the nucleic acid sequence SEQ ID NO: 11, a second variant comprising or consisting of the nucleic acid sequence SEQ ID NO: 81 and a third variant comprising or consisting of the nucleic acid sequence SEQ ID NO: 82.

The GPX4 gene is able to express 3 different variants: the first variant comprising or consisting of the nucleic acid sequence SEQ ID NO: 14, and a second variant comprising or consisting of the nucleic acid sequence SEQ ID NO: 83.

The PDRX5 gene is able to express 3 different variants: the first variant comprising or consisting of the nucleic acid sequence SEQ ID NO: 16, a second variant comprising or consisting of the nucleic acid sequence SEQ ID NO: 84 and a third variant comprising or consisting of the nucleic acid sequence SEQ ID NO: 85.

Thus, according to the invention, the measure of the expression level of the gene comprising or being constituted by SEQ ID NO: 5, can be evaluated by the measure of the expression level of the gene comprising or being constituted by SEQ ID NO: 73 or SEQ ID NO: 74.

In the same manner, the measure of the expression level of the gene comprising or being constituted by SEQ ID NO: 7, can be evaluated by the measure of the expression level of the gene comprising or being constituted by SEQ ID NO: 75 or SEQ ID NO: 76.

Moreover, the measure of the expression level of the gene comprising or being constituted by SEQ ID NO: 8, can be evaluated by the measure of the expression level of the gene comprising or being constituted by SEQ ID NO: 77, SEQ ID NO: 78 or SEQ ID NO: 79.

Moreover, the measure of the expression level of the gene comprising or being constituted by SEQ ID NO: 9, can be evaluated by the measure of the expression level of the gene comprising or being constituted by SEQ ID NO: 80.

Moreover, the measure of the expression level of the gene comprising or being constituted by SEQ ID NO: 11, can be evaluated by the measure of the expression level of the gene comprising or being constituted by SEQ ID NO: 81 or SEQ ID NO: 82.

Moreover, the measure of the expression level of the gene comprising or being constituted by SEQ ID NO: 14, can be evaluated by the measure of the expression level of the gene comprising or being constituted by SEQ ID NO: 83.

Moreover, the measure of the expression level of the gene comprising or being constituted by SEQ ID NO: 16, can be evaluated by the measure of the expression level of the gene comprising or being constituted by SEQ ID NO: 84 or SEQ ID NO: 85.

Therefore, as disclosed before and hereafter in the invention, the genes comprising or being constituted by the following sequences: SEQ ID NO: 5, SEQ ID NO: 7, SEQ ID NO: 8, SEQ ID NO: 9, SEQ ID NO: 11, SEQ ID NO: 14 and SEQ ID NO: 16 can be replaced by their respective variants, as defined above.

The genes used according to the invention are represented in the following table 1:

TABLE 1

| Gene name | SEQ ID |
|---|---|
| GPX3 | SEQ ID NO: 1 |
| GPX1 (1) | SEQ ID NO: 2 |
| GLRX2 (2) | SEQ ID NO: 3 |
| CAT | SEQ ID NO: 4 |
| PRDX (1-2-3) | SEQ ID NO: 5 |
|  | SEQ ID NO: 73 |
|  | SEQ ID NO: 74 |
| PRDX5 (2) | SEQ ID NO: 6 |
| SOD2 (1-2-3) | SEQ ID NO: 7 |
|  | SEQ ID NO: 75 |
|  | SEQ ID NO: 76 |
| GSR (1-2-3-4) | SEQ ID NO: 8 |
|  | SEQ ID NO: 77 |
|  | SEQ ID NO: 78 |
|  | SEQ ID NO: 79 |
| GLRX (1-2) | SEQ ID NO: 9 |
|  | SEQ ID NO: 80 |
| PRDX2 (1) | SEQ ID NO: 10 |
| PRDX5 (1-3) | SEQ ID NO: 11 |
|  | SEQ ID NO: 81 |
|  | SEQ ID NO: 82 |
| SOD1 | SEQ ID NO: 12 |
| TXN | SEQ ID NO: 13 |
| PRDX3 (1-2) | SEQ ID NO: 14 |
|  | SEQ ID NO: 83 |
| GPX7 | SEQ ID NO: 15 |
| GPX4 (1-2-3) | SEQ ID NO: 16 |
|  | SEQ ID NO: 84 |
|  | SEQ ID NO: 85 |
| TXN2 | SEQ ID NO: 17 |
| PRDX4 | SEQ ID NO: 18 |
| GPX1 (2) | SEQ ID NO: 19 |

TABLE 1-continued

| Gene name | SEQ ID |
|---|---|
| GLRX3 | SEQ ID NO: 20 |
| PRDX2 (3) | SEQ ID NO: 21 |
| PRDX6 | SEQ ID NO: 22 |
| GLRX5 | SEQ ID NO: 23 |
| GLRX2 (1) | SEQ ID NO: 24 |

Table 1 represents SEQ ID of the genes, and the variant when they exist, used in the invention.

According to the invention, hematological disorders correspond to disorders which primarily affect the blood. In particular, hematological disorders according to the invention encompass all cytopenias (anemia: decrease in red blood cell count or hemoglobin, thrombopenias: decrease in blood platelet count, and leukopenias: decrease in leukocyte count) whatever the mechanism such as hemoglobinopathies and myelodysplastic syndrome, myeloproliferative disorders (increased numbers of myeloid cells or myelofibrosis, including chronic myeloid leukemia, polycythemia vera, essential thrombocythemia, idiopathic myelofibrosis), lymphoproliferative disorders (increased numbers of lymphoid cells, including chronic lymphocytic leukemia, lymphomas, myeloma, plasmacytoma), acute leukemias and coagulopathies (disorders of bleeding and coagulation).

In one advantageous embodiment, the invention relates to a method as defined above, wherein if the ratio established in step b). is
  ≤0.3, for the gene comprising or being constituted by the nucleic acid sequence SEQ ID NO: 1, and
  ≥3.0, for the genes comprising or being constituted by the nucleic acid sequences SEQ ID NO: 2 and 3,
then said biological sample is representative of an acute myeloid leukemia.

In other words, an embodiment of the invention relates to a method as defined above, wherein if
  the ratio $R_1$ is ≤0.3, for the gene comprising or being constituted by the nucleic acid sequence SEQ ID NO: 1, and
  the ratios $R_2$ and $R_3$ are ≥3.0, for the genes comprising or being constituted by the nucleic acid sequences SEQ ID NO: 2 and 3, then said biological sample is representative of an acute myeloid leukemia.

In an embodiment of the invention, when the ratio $R_1$ is ≤0.3 and the ratios $R_2$ and $R_3$ are both ≥3, the sample originating from the patient is representative of an acute myeloid leukemia (AML). Said 3 criterions are cumulative.

AML are clonal proliferation of immature cells of the myeloid origin. They may appear de novo or secondary in patients with myelodysplastic syndrome (MDS). The classification prepared by the French-American-British group (FAB) considers eight varieties (M0-M7) based on morphological criteria and on the immunophenotype of the neoplastic cells (Bennett J M, et al., 1976).

The World Health Organisation (WHO) classifies AML by incorporating morphological, immunophenotypical, genetic and clinical data to be able to define biological homogeneous entities and with clinical relevance. Thus, AML is classified into four large categories:
  1. —AML with recurrent genetic anomalies,
  2. —AML with multilineage dysplasia,
  3. —AML related to treatment and
  4. —non-classifiable AML.

Before the invention, the cytogenetic analysis represented the most powerful prognosis factor. It is used to identify subgroups of AML with different prognosis: low risk with favourable response to treatment (t(8;21), t(15;17) or inv (16)), intermediate risk (normal karyotype or t(9;11) or high risk (inv(3), del(5q) or del(7q), or more than three alterations). There is molecular heterogeneity within the risk group. In some cases of patients with normal karyotype, the presence of mutations has been found in some genes.

Advantageously, the invention relates to the method as defined above, wherein if the ratio established in step b). is ≤0.3, for the gene comprising or being constituted by the nucleic acid sequence SEQ ID NO: 1, and ≥3.0, for the genes comprising or being constituted by the nucleic acid sequences SEQ ID NO: 2 and 3, and further wherein the ratio R10 between the expression level of the gene consisting of SEQ ID NO: 10 measured in said sample and in said control sample is lower than 0.5, (R10≤0.5), preferably is lower than 0.3, (R10≤0.3)

then said biological sample is representative of an acute myeloid leukemia.

In another embodiment, the invention relates to a method as defined above, wherein step c.) is such that if the ratio established in step b). for each genes of any combination of at least 3 genes from said sub-group is either ≥2 or ≤0.5, provided that the ratio between the expression level of the gene comprising or being constituted by the nucleic acid sequence SEQ ID NO: 1 measured in said biological sample and measured in said control sample, is not ≤0.3, or the ratios between the expression level of each of genes comprising or being constituted by the nucleic acid sequences SEQ ID NO: 2 or 3 measured in said biological sample and measured in said control sample, is not ≥3, then said biological sample is representative of a myelodysplasic disorder, in particular myelodysplasia chosen among refractory anemia (RA), refractory anemia with ringed sideroblasts (RARS), refractory cytopenia with multilineage dysplasia (RCMD), refractory anemia with excess of blasts (RAEB), 5q-syndrome and myelodysplasia unclassifiable.

In other words, in another advantageous embodiment, the invention relates to a method as defined above, wherein if the ratio established in step b). for each genes of any combination of at least 3 genes from said sub-group is either ≥2 or ≤0.5, provided that if the combination of at least 3 genes corresponds to the genes comprising or being constituted by the nucleic acid sequence SEQ ID NO: 1, 2 and 3, wherein the ratio RI is ≤0.3, for the gene comprising or being constituted by the nucleic acid sequence SEQ ID NO: 1, and the ratios RI are ≥3.0, for the genes comprising or being constituted by the nucleic acid sequences SEQ ID NO: 2 and 3, this combination is excluded then said biological sample is representative of a myelodysplasic disorder, in particular myelodysplasia chosen among refractory anemia with ringed sideroblasts (RARS), refractory cytopenia with multilineage dysplasia (RCMD), refractory anemia with excess of blasts (RAEB) or 5q-syndrome and unclassifiable myelodysplasia.

According to the invention, if the ratio of at least 3 genes belonging to the sub-group constituted by the genes comprising or being constituted by the nucleic acid SEQ ID NO: 1-6 is either ≥2 or ≤0.5, excluding the particular combination of SEQ ID NO: 1, SEQ ID NO: 2 and SEQ ID NO: 2 wherein the ratio of SEQ ID NO: 1 is ≤0.3 and the ratios of SEQ ID NO: 2 and 3 are ≥3, then biological sample is representative of a myelodysplasic disorder, in particular myelodysplasia chosen among refractory anemia with ringed sideroblasts (RARS), refractory cytopenia with multilineage dysplasia (RCMD), refractory anemia with excess of blasts (RAEB) or 5q-syndrome and unclassifiable myelodysplasia.

According to the invention, myelodysplasic disorders are defined as preleukemia, and correspond to diverse collection of hematological conditions united by ineffective production (or dysplasia) of myeloid blood cells and risk of transformation to acute myelogenous leukemia (AML).

The French-American-British (FAB) classification has subdivided the myelodysplasic disorders as follows:

Refractory anemia (RA), characterized by less than 5% primitive blood cells (myeloblasts) in the bone marrow and pathological abnormalities primarily seen in red cell precursors, Refractory anemia with ringed sideroblasts (RARS), also characterized by less than 5% myeloblasts in the bone marrow, but distinguished by the presence of 15% or greater red cell precursors in the marrow being abnormal iron-stuffed cells called "ringed sideroblasts", Refractory anemia with excess blasts (RAEB), characterized by 5-20% myeloblasts in the marrow, Refractory anemia with excess blasts in transformation (RAEB-T), characterized by 21-30% myeloblasts in the marrow (>30% blasts is defined as acute myeloid leukemia), and Chronic myelomonocytic leukemia (CMML), not to be confused with chronic myelogenous leukemia or CML, characterized by less than 20% myeloblasts in the bone marrow and greater than $1000 \times 10^9/\mu L$ monocytes (a type of white blood cell) circulating in the peripheral blood.

More recently, the World Health Organization (WHO) has classified dysplastic syndromes as follows:

TABLE 2

| Old system | New system |
|---|---|
| Refractory anemia (RA) | Refractory cytopenia with unilineage dysplasia (Refractory anemia, Refractory neutropenia, and Refractory thrombocytopenia) |
| Refractory anemia with ringed sideroblasts (RARS) | Refractory anemia with ring sideroblasts (RARS) Refractory anemia with ring sideroblasts - thrombocytosis (RARS-t) (provisional entity) which is in essence a myelodysplastic/myeloproliferative disorder and usually has a JAK2 mutation (janus kinase) - New WHO classification 2008 |
| Refractory cytopenia with multilineage dysplasia (RCMD) | Refractory cytopenia with multilineage dysplasia (RCMD) includes the subset Refractory cytopenia with multilineage dysplasia and ring sideroblasts (RCMD-RS). RCMD includes patients with pathological changes not restricted to red cells (i.e., prominent white cell precursor and platelet precursor (megakaryocyte) dysplasia. |
| Refractory anemia with excess blasts (RAEB) | Refractory anemia with excess blasts I and II. RAEB was divided into RAEB-I (5-9% blasts) and RAEB-II (10-19%) blasts, which has a poorer prognosis than |

TABLE 2-continued

| Old system | New system |
|---|---|
| | RAEB-I. Auer rods may be seen in RAEB-II which may be difficult to distinguish from acute myeloid leukemia. |
| Refractory anemia with excess blasts in transformation (RAEB-T) | The category of RAEB-T was eliminated; such patients are now considered to have acute leukemia. 5q-syndrome, typically seen in older women with normal or high platelet counts and isolated deletions of the long arm of chromosome 5 in bone marrow cells, was added to the classification. |
| Chronic myelomonocytic leukemia (CMML) | CMML was removed from the myelodysplastic syndromes and put in a new category of myelodysplastic-myeloproliferative overlap syndromes. 5q-syndrome Unclassifiable myelodysplasia (seen in those cases of megakaryocyte dysplasia with fibrosis and others) Refractory cytopenia of childhood (dysplasia in childhood) - New WHO classification 2008 |

Chromosome 5q deletion syndrome (chromosome 5q monosomy, 5q-syndrome) is a rare disorder caused by loss of part of the long arm (q arm) of human chromosome 5.

The 5q-syndrome is characterized by macrocytic anemia and often thrombocytosis, erythroblastopenia, megakaryocyte hyperplasia with nuclear hypolobation and an isolated interstitial deletion of chromosome 5. The 5q-syndrome is found predominantly in females of advanced age.

In still another embodiment, the invention relates to a method above defined, wherein said set comprises 10 genes, said 10 genes comprising or being constituted by the nucleic acid sequences SEQ ID NO: 1 to 10, and the step c). is such that if the ratio established in step b). for each genes of any combination of 3 genes from said sub-group is either ≥2 or ≤0.5, provided that the ratio between the expression level of the gene comprising or being constituted by the nucleic acid sequence SEQ ID NO: 1 measured in said biological sample and measured in said control sample, is not ≤0.3, or the ratios between the expression level of each of genes comprising or being constituted by the nucleic acid sequences SEQ ID NO: 2 or 3 measured in said biological sample and measured in said control sample, is not ≥3 and further if the ratio established in step b) for at least one gene of said set that does not belong to said subgroup is ≥2 and the ratio established in step b) of at least one other gene of said set that does not belong to said subgroup is ≤0.5, then said biological sample is representative of a refractory anemia with excess of blast or of a 5q-syndrome.

In other words, in still another advantageous embodiment, the invention relates to a method above defined, wherein said set comprises 10 genes, said 10 genes comprising or being constituted by the nucleic acid sequences SEQ ID NO: 1 to 10, and the step c). is such that if the ratio established in step b). for each genes of any combination of 3 genes from said sub-group is either ≥2 or ≤0.5, provided that if the combination of at least 3 genes corresponds to the genes comprising or being constituted by the nucleic acid sequence SEQ ID NO: 1, 2 and 3, wherein the ratio RI is ≤0.3, for the gene comprising or being constituted by the nucleic acid sequence SEQ ID NO: 1, and the ratios RI are ≥3.0, for the genes comprising or being constituted by the nucleic acid sequences SEQ ID NO: 2 and 3, this combination is excluded, and further if the ratio established in step b) for at least one gene of said set that does not belong to said subgroup is ≥2 and the ratio established in step b) of at least one other gene of said set that does not belong to said subgroup is ≤0.5, then said biological sample is representative of a refractory anaemia with excess of blast or of a 5q-syndrome.

In this advantageous embodiment of the invention, the genes belonging to the set (i.e. genes comprising or being constituted by SEQ ID NO: 1 to 10) are helpful for discriminating the myelodysplastic disorders.

More precisely, the genes belonging to the set but that do not belong to the sub group (i.e. genes comprising or being constituted by SEQ ID NO: 7 to 10—D in FIG. 2) are helpful for discriminating the myelodysplastics disorders.

Then, if, by measuring the expression level of the genes SEQ ID NO: 1-6, the biological sample is considered to be representative of myelodyplastic disorder, it is possible according to the invention to separate refractory anemia with excess of blast and of a 5q-syndrome from the other pathologies, when the ratio of the expression of at least one gene of the group consisting of SEQ ID NO: 7 to 10 is ≥2 and when the ratio of the expression of at least one gene of the group consisting of SEQ ID NO: 7 to 10 is ≤0.5.

Another advantageous embodiment of the invention relates to a method previously defined, wherein said set comprises 10 genes, said 10 genes comprising or being constituted by the nucleic acid sequences SEQ ID NO: 1 to 10, and the step c). is such that if the ratio established in step b). for each genes of any combination of 3 genes from said sub-group is either ≥2 or ≤0.5, provided that the ratio between the expression level of the gene comprising or being constituted by the nucleic acid sequence SEQ ID NO: 1 measured in said biological sample and measured in said control sample, is not ≤0.3, or the ratios between the expression level of each of genes comprising or being constituted by the nucleic acid sequences SEQ ID NO: 2 or 3 measured in said biological sample and measured in said control sample, is not ≥3, and if the ratio established in step b) for at least one gene of said set that does not belong to said subgroup is ≥2 and the ratio established in step b) of at least one other gene of said set that does not belong to said subgroup is ≤0.5, and further if the ratio established in step b) for at least 4 genes of the group of 24 genes that does not belong to said set is ≥3, then said biological sample is representative of a refractory anemia with excess of blast.

In other words, another advantageous embodiment of the invention relates to a method previously defined, wherein
said set comprises 10 genes, said 10 genes comprising or being constituted by the nucleic acid sequences SEQ ID NO: 1 to 10, and the step c). is such that
if the ratio established in step b). for each genes of any combination of 3 genes from said sub-group is either ≥2 or ≤0.5,
provided that if the combination of at least 3 genes corresponds to the genes comprising or being constituted by the nucleic acid sequence SEQ ID NO: 1, 2 and 3, wherein
the ratio $R_i$ is ≤0.3, for the gene comprising or being constituted by the nucleic acid sequence SEQ ID NO: 1, and
the ratios $R_i$ are ≥3.0, for the genes comprising or being constituted by the nucleic acid sequences SEQ ID NO: 2 and 3,
this combination is excluded,
and
if the ratio established in step b) for at least one gene of said set that does not belong to said subgroup is ≥2 and the ratio established in step b) of at least one other gene of said set that does not belong to said subgroup is ≤0.5, and further
if the ratio established in step b) for at least 4 genes of the group of 24 genes that does not belong to said set is ≥3,
then said biological sample is representative of a refractory anaemia with excess of blast.

In this advantageous embodiment of the invention, the genes belonging to the group (i.e. genes comprising or being constituted by SEQ ID NO: 1 to 24) are helpful for discriminating between refractory anaemia with excess of blast and of a 5q-syndrome.

More precisely, the genes belonging to the group but that do not belong to the set (i.e. genes comprising or being constituted by SEQ ID NO: 11 to 24—E in FIG. 2) are helpful for the discrimination between refractory anaemia with excess of blast and of a 5q-syndrome.

The invention also relates to a method for the diagnosis, and/or the classification, preferably in vitro, of an hematological disorder, in particular myeloid and/or lymphoid hematological disorder, preferably myeloid hematological disorder,
said method comprising the steps of:
a). measuring, from cells contained in a biological sample of a subject, preferably from blood cells or bone marrow cells containing sample, the expression level of at least the genes of a sub-group of 6 genes belonging to a set of genes chosen among a group of 24 genes, said group of 24 genes comprising or being constituted by the nucleic acid sequences SEQ ID NO:1 to 24,
said 6 genes belonging to said sub-group comprising or being constituted by the nucleic acid sequences SEQ ID NO: 1 to 6,
b). comparing the expression level of each genes measured in step a)., with the expression level of the same respective genes from cells contained in a control sample, preferably from a control sample containing blood cells or bone marrow cells, said control sample being of the same nature than said biological sample, to establish a gene expression level ratio Ri between the expression level of each genes measured in step a) and the expression level of the same respective genes from cells contained in a control sample, for each genes of said sub-group, and c). determining the status of said biological sample such that if the ratio Ri for each genes of any combination of 3 genes from said sub-group is
either ≥2,
or ≤0.5,
said biological sample is representative of an hematological disorder cells.

An advantageous embodiment of the invention relates to a method as defined above, wherein if
the ratio $R_i$ is ≤0.3, for the gene comprising or being constituted by the nucleic acid sequence SEQ ID NO: 1, and
the ratios $R_i$ are ≥3.0, for the genes comprising or being constituted by the nucleic acid sequences SEQ ID NO: 2 and 3,
then said biological sample is representative of an acute myeloid leukemia.

In this advantageous embodiment of the method according to the invention, in step c). when the ratio Ri of the expression level of the genes GPX3 (SEQ ID NO: 1)≤0.3, the ratio of the expression level of the genes GPX1(1) (SEQ ID NO: 2) is ≥3.0 and the ratio of the expression level of the genes GLRX2(2) (SEQ ID NO: 3) is ≥3.0, then the biological sample is representative of an acute myeloid leukemia (AML).

In another advantageous embodiment, the invention relates to a method as defined above, wherein step c.) is such that
if the ratio $R_i$ established in step b). for each genes of any combination of at least 3 genes from said sub-group is either ≥2 or ≤0.5,
provided that if the combination of 3 genes corresponds to the genes comprising or being constituted by the nucleic acid sequence SEQ ID NO: 1, 2 and 3, wherein
the ratio $R_i$ is ≤0.3, for the gene comprising or being constituted by the nucleic acid sequence SEQ ID NO: 1, and
the ratios $R_i$ are ≥3.0, for the genes comprising or being constituted by the nucleic acid sequences SEQ ID NO: 2 and 3,
said combination is excluded
then said biological sample is representative of a myelodysplasic disorder, in particular myelodysplasia chosen among refractory anaemia with ringed sideroblasts (RARS), refractory cytopenia with multilineage dysplasia (RCMD), refractory anemia with excess of blasts (RAEB) or 5q-syndrome and unclassifiable myelodysplasia.

In other words, when the ratio Ri, established in step c)., of the expression level of each gene of any combination of at least 3 genes chosen among the genes comprising or being constituted by SEQ ID NO: 1-6 is either ≥2 or ≤0.5, and said combination does not corresponds to the combination that defines a biological sample as representative of an AML, then said sample is representative of a myelodysplastic disorder or syndrome.

Another advantageous embodiment of the invention relates to a method previously defines, wherein
said set comprises 10 genes, said 10 genes comprising or being constituted by the nucleic acid sequences SEQ ID NO: 1 to 10, and further, in step c.)
if the ratio Ri of all the genes of said set that do not belong to said subgroup is comprised between 0.3 to 2, the extremity of the interval being excluded
then said biological sample is representative of a refractory anemia with ringed sideroblasts or a refractory cytopenia with multilineage dysplasia.

In the invention "the genes of said set that do not belong to said subgroup" corresponds to the genes belonging to the group D as defined in FIG. 2.

Since the subgroup consists of the genes comprising or being constituted by the nucleic acid sequences SEQ ID NO: 1-6 and the set consists of the genes comprising or being constituted by the nucleic acid sequences SEQ ID NO: 1-10, consequently, the genes of said set that do not belong to said subgroup correspond to the genes comprising or being constituted by the nucleic acid sequences SEQ ID NO: 7-10.

In the above embodiment, if the ratio $R_i$ for each gene represented by the nucleic acid sequences SEQ ID NO: 7, SEQ ID NO: 8, SEQ ID NO: 9 and SEQ ID NO: 10, i.e. all the ratios of said genes, is comprised between 0.3 and 2, 0.3 and 2 being excluded from the interval, said biological sample is representative of a refractory anemia with ringed sideroblasts or a refractory cytopenia with multilineage dysplasia.

It is possible to write that if 0.3<R7<2, and 0.3<R8<2, and 0.3<R9<2, and 0.3<R10<2, R7, R8, R9 and R10 representing the respective ratio for the genes represented by SEQ ID NO: 7, 8, 9 and 10), further to the evaluation of the ratio of the genes SEQ ID NO: 1-6, then said biological sample is representative of a refractory anemia with ringed sideroblasts or a refractory cytopenia with multilineage dysplasia.

The terms "comprised between 0.3 to 2, the extremity of the interval being excluded" refer to the interval represented by the mathematical symbol: ]0.3;2.0[. This interval includes all the values comprised between 0.3 and 2.0, but excludes the specific values 0.3 and 2.

If Ri=0.3, or Ri=2.0, Ri does not belong to the interval ]0.3;2.0[.

The evaluation of the ratio of the expression level of the genes represented by SEQ ID NO: 7-10, in a specific interval, allows to discriminate some myelodysplastic syndrome.

To summarise,
if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and the ratio of each gene represented by SEQ ID NO: 7, 8, 9 and 10 is comprised in the interval ]0.3; 2.0[, then the biological sample is representative of a refractory anemia with ringed sideroblasts or a refractory cytopenia with multilineage dysplasia.

In one another advantageous embodiment, the invention relates to a method according the definition mentioned above, wherein further, in step c.)
if the ratio Ri of at least one gene belonging to said group of genes that does not belong to said set is ≤0.3, then said biological sample is representative of a refractory anemia with ringed sideroblasts, and
if the ratio RI of at least one gene belonging to said group of genes that do not belong to said set is ≥3.0,
then said biological sample is representative of a refractory cytopenia with multilineage dysplasia.

In the invention "gene belonging to said group of genes that does not belong to said set" corresponds to the genes belonging to the group E as defined in FIG. 2.

Since the subgroup consists of the genes comprising or being constituted by the nucleic acid sequences SEQ ID NO: 1-6, the set consists of the genes comprising or being constituted by the nucleic acid sequences SEQ ID NO: 1-10, and the group consists of the genes comprising or being constituted by the nucleic acid sequences SEQ ID NO: 1-24, consequently, the genes of said group that do not belong to said set correspond to the genes comprising or being constituted by the nucleic acid sequences SEQ ID NO: 11-24.

In the above embodiment, the genes represented by SEQ ID NO: 11, 12, 13, 14, 15, 16, 17, 18, 19, 20, 21, 22, 23 and 24 provide supplemental information regarding the nature of the tested biological sample.

To summarise,
1) a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and
b) the ratio of each gene represented by SEQ ID NO: 7, 8, 9 and 10 is comprised in the interval ]0.3; 2.0[, and
c) the ratio of at least 1 gene, i.e. 1, or 2, or 3, or 4, or 5, or 6, or 7, or 8, or 9, or 10, or 11, or 12, or 13, or 14 genes, represented by SEQ ID NO: 11, 12, 13, 14, 15, 16, 17, 18, 19, 20, 21, 22, 23 and 24 is ≥3.0, then said biological sample is representative of a refractory cytopenia with multilineage dysplasia, and 2)) a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and
b) the ratio of each gene represented by SEQ ID NO: 7, 8, 9 and 10 is comprised in the interval ]0.3; 2.0[, and
c) the ratio of at least 1 gene, i.e. 1, or 2, or 3, or 4, or 5, or 6, or 7, or 8, or 9, or 10, or 11, or 12, or 13, or 14 genes, represented by SEQ ID NO: 11, 12, 13, 14, 15, 16, 17, 18, 19, 20, 21, 22, 23 and 24 is ≤0.3, then said biological sample is representative of a refractory anemia with ringed sideroblasts.

In one other embodiment, the invention relates to a method as defined above, wherein
said set comprises 10 genes, said 10 genes comprising or being constituted by the nucleic acid sequences SEQ ID NO: 1 to 10,
and further
if
the ratio $R_i$ of at least one gene of said set that does not belong to said subgroup is ≥2.0, or
the ratio $R_i$ of at least one gene of said set that does not belong to said subgroup is ≤0.3, or
the ratio $R_i$ of at least one gene of said set that does not belong to said subgroup is ≥2.0 and the ratio Ri of another gene that does not belong to said subgroup is ≤0.3,
then said biological sample is representative of chosen among refractory cytopenia with multilineage dysplasia, refractory anemia with excess of blasts, 5 q-syndroma and unclassified myelodysplasia.

In this advantageous embodiment, it is taking account of the case wherein at least one gene represented by SEQ ID NO: 7, 8 9 or 10 does not belong to the interval ]0.3; 2.0[ as defined above.

In a first case, at least one gene has a ratio ≥2.0, whatsoever the ratio of the other genes. In a second case at least one gene has a ratio ≤0.3, whatsoever the ratio of the other genes. In a third case, both at least one gene has a ratio ≥2.0 and another gene has a ratio ≤0.3, whatsoever the ratio of the other genes.

In one other advantageous embodiment, the invention relates to a method previously defined, wherein
if the ratio $R_i$ of at least one gene of said set that does not belong to said subgroup is ≥2.0 and the ratio $R_i$ of at least another gene of said set that does not belong to said subgroup is ≤0.5, then said biological sample is a representative refractory anemia with excess of blasts or of 5q-syndrome.

This embodiment concerns the case in which at least one gene has a ratio ≥2.0, whatsoever the ratio of the other genes, and in particular the case in which at least one gene has a ratio ≥2.0 and another gene has a ratio ≤0.5, and therefore possibly ≤0.3.

This particular situation allows to detect, or to identify, myelodysplastic syndromes that are representative refractory anemia with excess of blasts or of 5q-syndrome.

In one other advantageous embodiment, the invention relates to a method previously defined, wherein if the ratio $R_i$ of at least one gene of said set that does not belong to said subgroup is ≥2.0 and the ratio $R_i$ of at least another gene of said set that does not belong to said subgroup is ≤0.5, then said biological sample is a representative refractory anemia with excess of blast or 5q-syndrome, and further if the ratios $R_i$ of at least four genes belonging to said group of genes that do not belong to said set are ≥3.0, then said biological sample is representative of a refractory anemia with excess of blasts, and if the ratios $R_i$ of at most three genes belonging to said group of genes that do not belong to said set are ≥3.0, then said biological sample is representative of a 5q-syndrome.

To summarise, 1) a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and b) the ratio of at least one gene represented by SEQ ID NO: 7, 8, 9 and 10 is ≥2.0, and at least one other gene represented by SEQ ID NO: 7, 8, 9 and 10 is ≤0.5, and c) the ratios of at least 4 genes, i.e. 4, or 5, or 6, or 7, or 8, or 9, or 10, or 11, or 12, or 13, or 14 genes, represented by SEQ ID NO: 11, 12, 13, 14, 15, 16, 17, 18, 19, 20, 21, 22, 23 and 24 are ≥3.0, then said biological sample is representative of refractory anemia with excess of blasts, and 2)) a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and b) the ratio of at least one gene represented by SEQ ID NO: 7, 8, 9 and 10 is ≥2.0, and at least one other gene represented by SEQ ID NO: 7, 8, 9 and 10 is ≤0.5, and c) the ratios of at most 3 genes, i.e. 0, or 1, or 2, or 3, genes, represented by SEQ ID NO: 11, 12, 13, 14, 15, 16, 17, 18, 19, 20, 21, 22, 23 and 24 are ≥3.0, then said biological sample is representative of a 5q-syndrome.

In one other advantageous embodiment, the invention relates to a method according the above definition, wherein if the ratio $R_i$ of at least one gene of said set that does not belong to said subgroup is ≥2.0 and the ratio $R_i$ of no gene of said set that does not belong to said subgroup is ≤0.5, then said biological sample is representative of a refractory cytopenia with multilineage dysplasia, In this specific embodiment, if the ratio of at least one gene represented by SEQ ID NO: 7, 8 9 or 10 is ≥2.0 and the ratio of the other genes is included in the interval [0.5; +∞[, then said biological sample is representative of a refractory cytopenia with multilineage dysplasia.

To summarize:

a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and b) the ratio of at least one gene represented by SEQ ID NO: 7, 8, 9 and 10 is ≥2.0, and the ratio of no gene represented by SEQ ID NO: 7, 8, 9 and 10 is ≤0.5, then said biological sample is representative of a refractory cytopenia with multilineage dysplasia.

In one other advantageous embodiment, the invention relates to a method according the above definition, wherein further if the ratio $R_i$ of at least one gene of said set that does not belong to said subgroup is ≤0.5 and the ratio RI of no gene of said set that does not belong to said subgroup is ≥2.0, then said biological sample is representative of refractory anemia with ringed sideroblasts, refractory cytopenia with multilineage dysplasia, refractory anemia with excess of blasts, 5q-syndrome or unclassified myelodysplasia, In this specific embodiment, if the ratio of at least one gene represented by SEQ ID NO: 7, 8 9 or 10 is ≤0.5 and the ratio of the other genes is included in the interval]–∞; 2.0], then said biological sample is representative of refractory anemia with ringed sideroblasts, refractory cytopenia with multilineage dysplasia, refractory anemia with excess of blasts, 5q-syndrome or unclassified myelodysplasia.

To summarize:

a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and b) the ratio of at least one gene represented by SEQ ID NO: 7, 8, 9 and 10 is ≤0.5, and the ratio of no gene represented by SEQ ID NO: 7, 8, 9 and 10 is ≥2.0, then said biological sample is representative of refractory anemia with ringed sideroblasts, refractory cytopenia with multilineage dysplasia, refractory anemia with excess of blasts, 5q-syndrome or unclassified myelodysplasia.

In one other advantageous embodiment, the invention relates to a method as defined above, wherein, in step c.)

if the ratio $R_i$ of at least one gene of said set that does not belong to said subgroup is ≤0.5 and the ratio $R_i$ of no gene of said set that does not belong to said subgroup is ≥2.0, and further if the ratios $R_i$ of all the genes belonging to said group of genes that do not belong to said set are comprised between 0.5 to 2, the extremity of the interval being excluded, then said biological sample is representative of a unclassified myelodysplasia, In this advantageous embodiment the genes represented by SEQ ID NO: 11, 12, 13, 14, 15, 16, 17, 18, 19, 20, 21, 22, 23 or 24 are useful for discriminate unclassified myelodysplasia from refractory anemia with ringed sideroblasts, refractory cytopenia with multilineage dysplasia and 5q-syndrome.

In one other advantageous embodiment, the invention relates to a method as defined above, wherein, in step c.)

if the ratio $R_i$ of at least one gene of said set that does not belong to said subgroup is ≤0.3 and the ratio $R_i$ of no gene of said set that does not belong to said subgroup is ≥2.0, and further if the ratios $R_i$ of at least one gene belonging to said group of genes that do not belong to said set is ≥2.0, then said biological sample is representative of a 5q-syndrome or refractory cytopenia with multilineage dysplasia.

To summarize:

a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and b) the ratio of at least one gene represented by SEQ ID NO: 7, 8, 9 and 10 is ≤0.3, and the ratio of no gene represented by SEQ ID NO: 7, 8, 9 and 10 is ≥2.0, and c) the ratios RI of at least one gene represented by SEQ ID NO: 11, 12, 13, 14, 15, 16, 17, 18, 19, 20, 21, 22, 23 or 24 is ≥2.0, then said biological sample is representative of a 5q-syndrome or refractory cytopenia with multilineage dysplasia.

Another advantageous embodiment of the invention relates to a method as defined above, wherein if the ratio $R_i$ of at least one gene of said set that does not belong to said subgroup is ≤0.3 and the ratio $R_i$ of no gene that does not belong to said subgroup is ≥2.0, then said biological sample is representative of a unclassified myelodysplasia, a 5q-syndrome, or of a refractory cytopenia with multilineage dysplasia.

To summarize:

a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and b) the ratio of at least one gene represented by SEQ ID NO: 7, 8, 9 and 10 is ≤0.3, and the ratio of no gene represented by SEQ ID NO: 7, 8, 9 and 10 is ≥2.0, said biological sample is representative of a unclassified myelodysplasia, a 5q-syndrome, or of a refractory cytopenia with multilineage dysplasia.

Another advantageous embodiment of the invention relates to a method as defined above, wherein if the ratio $R_i$ of at least one gene of said set that does not belong to said subgroup is ≤0.3 and the ratio $R_i$ of no gene that does not belong to said subgroup is ≥2.0, and further if the ratios $R_i$ of at least two genes of said set that do not belong to said subgroup are ≤0.3 and the ratio $R_i$ of no gene of said set that does not belong to said subgroup is ≥2.0, then said biological sample is representative of a 5q-syndrome, or of refractory cytopenia with multilineage dysplasia.

To summarize:

a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and b) the ratio of at least one gene represented by SEQ ID NO: 7, 8, 9 and 10 is ≤0.3, the ratio of at least one other gene represented by SEQ ID NO: 7, 8, 9 and 10 is ≤0.3 and the ratio of no gene represented by SEQ ID NO: 7, 8, 9 and 10 is ≥2.0, said biological sample is representative of a 5q-syndrome, or of a refractory cytopenia with multilineage dysplasia.

Another advantageous embodiment of the invention relates to a method as defined above, wherein if the ratio $R_i$ of at least one gene of said set that does not belong to said subgroup is ≤0.3 and the ratio $R_i$ of no gene that does not belong to said subgroup is ≥2.0, and if the ratios $R_i$ of at least two genes of said set that do not belong to said subgroup are ≤0.3 and the ratio $R_i$ of no gene of said set that does not belong to said subgroup is ≥2.0, then said biological sample is representative of a 5q-syndrome, or of refractory cytopenia with multilineage dysplasia.

and if further the ratios $R_i$ of at least two genes belonging to said group of genes that do not belong to said set are ≥2.0, then said biological sample is representative of a 5q-syndrome.

To summarize:

a) if the ratio for each gene of any combination of 3 genes chosen among the 6 genes represented by SEQ ID NO: 1, 2, 3, 4, 5 and 6, is either ≥2.0 or ≤0.5, excluding the combination that defines leukemia, and b) the ratio of at least one gene represented by SEQ ID NO: 7, 8, 9 and 10 is ≤0.3, the ratio of at least one other gene represented by SEQ ID NO: 7, 8, 9 and 10 is ≤0.3 and the ratio of no gene represented by SEQ ID NO: 7, 8, 9 and 10 is ≥2.0, and c) the ratios of at least two genes represented by SEQ ID NO: 11, 12, 13, 14, 15, 16, 17, 18, 19, 20, 21, 22, 23 or 24 are ≥2.0, said biological sample is representative of a 5q-syndrome.

The invention also relates to a method for the diagnosis, and/or the classification, preferably in vitro, of an hematological disorder, in particular myeloid and/or lymphoid hematological disorder, preferably myeloid hematological disorder, said method comprising the steps of:

a). measuring, from cells contained in a biological sample of a subject, preferably from blood cells or bone marrow cells containing sample, the expression level 24 genes, said 24 genes comprising or being constituted by the nucleic acid sequences SEQ ID NO:1 to 24, b). comparing the expression level of each genes measured in step a)., with the expression level of the same respective genes from cells contained in a control sample preferably from blood cells or bone marrow cells containing sample, said control sample being of the same nature than said biological sample, to establish a gene expression level ratio for each genes of said sub-group, and c). determining the status of said biological sample such that if the ratio established in step b).

More advantageously, the invention relates to a method previously defined, wherein the expression level of the genes is measured by a method allowing the determination of the amount of the mRNA or of the cDNA corresponding to said genes. Preferably said method is a quantitative method.

Levels of mRNA can be quantitatively measured by northern blotting which gives size and sequence information about the mRNA molecules. A sample of RNA is separated on an agarose gel and hybridized to a radio-labeled RNA probe that is complementary to the target sequence. The radio-labeled RNA is then detected by an autoradiograph. Northern blotting is widely used as the additional mRNA size information allows the discrimination of alternately spliced transcripts.

Another approach for measuring mRNA abundance is reverse transcription quantitative polymerase chain reaction (RT-PCR followed with qPCR). RT-PCR first generates a DNA template from the mRNA by reverse transcription, which is called cDNA. This cDNA template is then used for qPCR where the change in fluorescence of a probe changes as the DNA amplification process progresses. With a carefully constructed standard curve qPCR can produce an absolute measurement such as number of copies of mRNA, typically in units of copies per nanolitre of homogenized tissue or copies per cell. qPCR is very sensitive (detection of a single mRNA molecule is possible), but can be expensive due to the fluorescent probes required.

Northern blots and RT-qPCR are good for detecting whether a single gene or few genes are expressed.

Other methods known for one skilled in the art include DNA microarrays or technologies like Serial Analysis of Gene Expression (SAGE).

SAGE can provide a relative measure of the cellular concentration of different messenger RNAs. The great advantage of tag-based methods is the "open architecture", allowing for the exact measurement of any transcript are present in cells, the sequence of said transcripts could be known or unknown.

The preferred method used according to the invention is RT-qPCR.

In still another advantageous embodiment, the invention relates to a method above defined, wherein the measure of the expression level of the genes is carried out by using the at least 6 pairs of oligonucleotides belonging to a group of 24 pairs of oligonucleotides comprising or being constituted by the nucleic acid sequences SEQ ID NO: 25 to 72, said at least 6 pairs of oligonucleotides comprising or being constituted by the nucleic acid sequences SEQ ID NO: 25 to 36.

In the invention:
the pair of oligonucleotides comprising of being constituted by the nucleic acid sequences SEQ ID NO: 25 and SEQ ID NO: 26, are used for measuring the expression level of the gene comprising or being constituted by the nucleic acid sequence SEQ ID NO: 1,
the pair of oligonucleotides comprising of being constituted by the nucleic acid sequences SEQ ID NO: 27 and SEQ ID NO: 28, are used for measuring the expression level of the gene comprising or being constituted by the nucleic acid sequence SEQ ID NO: 2,
the pair of oligonucleotides comprising of being constituted by the nucleic acid sequences SEQ ID NO: 29 and SEQ ID NO: 30, are used for measuring the expression level of the gene comprising or being constituted by the nucleic acid sequence SEQ ID NO: 3,
the pair of oligonucleotides comprising of being constituted by the nucleic acid sequences SEQ ID NO: 31 and SEQ ID NO: 32, are used for measuring the expression level of the gene comprising or being constituted by the nucleic acid sequence SEQ ID NO: 4,
the pair of oligonucleotides comprising of being constituted by the nucleic acid sequences SEQ ID NO: 33 and SEQ ID NO: 34, are used for measuring the expression level of the gene comprising or being constituted by the nucleic acid sequence SEQ ID NO: 5,
the pair of oligonucleotides comprising of being constituted by the nucleic acid sequences SEQ ID NO: 35 and SEQ ID NO: 36, are used for measuring the expression level of the gene comprising or being constituted by the nucleic acid sequence SEQ ID NO: 6.

In one advantageous embodiment, the inventions relates to the method as defined above,
using the at least 10 pairs of oligonucleotides belonging to a group of 24 pairs of oligonucleotides comprising or being constituted by the nucleic acid sequences SEQ ID NO: 25 to 72, said at least 6 pairs of oligonucleotides comprising or being constituted by the nucleic acid sequences SEQ ID NO: 25 to 44.

In the invention:
the pair of oligonucleotides comprising of being constituted by the nucleic acid sequences SEQ ID NO: 36 and SEQ ID NO: 37, are used for measuring the expression level of the gene comprising or being constituted by the nucleic acid sequence SEQ ID NO: 7,
the pair of oligonucleotides comprising of being constituted by the nucleic acid sequences SEQ ID NO: 38 and SEQ ID NO: 39, are used for measuring the expression level of the gene comprising or being constituted by the nucleic acid sequence SEQ ID NO: 8,
the pair of oligonucleotides comprising of being constituted by the nucleic acid sequences SEQ ID NO: 41 and SEQ ID NO: 42, are used for measuring the expression level of the gene comprising or being constituted by the nucleic acid sequence SEQ ID NO: 9,
the pair of oligonucleotides comprising of being constituted by the nucleic acid sequences SEQ ID NO: 43 and SEQ ID NO: 44, are used for measuring the expression level of the gene comprising or being constituted by the nucleic acid sequence SEQ ID NO: 10.

In one advantageous embodiment, the inventions relates to the method as defined above,
using 24 pairs of oligonucleotides comprising or being constituted by the nucleic acid sequences SEQ ID NO: 25 to 72.

In the invention:
the pair of oligonucleotides comprising of being constituted by the nucleic acid sequences SEQ ID NO: 45 and SEQ ID NO: 46, are used for measuring the expression level of the gene comprising or being constituted by the nucleic acid sequence SEQ ID NO: 11,
the pair of oligonucleotides comprising of being constituted by the nucleic acid sequences SEQ ID NO: 47 and SEQ ID NO: 48, are used for measuring the expression level of the gene comprising or being constituted by the nucleic acid sequence SEQ ID NO: 12,
the pair of oligonucleotides comprising of being constituted by the nucleic acid sequences SEQ ID NO: 49 and SEQ ID NO: 50, are used for measuring the expression level of the gene comprising or being constituted by the nucleic acid sequence SEQ ID NO: 13,
the pair of oligonucleotides comprising of being constituted by the nucleic acid sequences SEQ ID NO: 51 and SEQ ID NO: 52, are used for measuring the expression level of the gene comprising or being constituted by the nucleic acid sequence SEQ ID NO: 14,
the pair of oligonucleotides comprising of being constituted by the nucleic acid sequences SEQ ID NO: 53 and SEQ ID NO: 54, are used for measuring the expression level of the gene comprising or being constituted by the nucleic acid sequence SEQ ID NO: 15,
the pair of oligonucleotides comprising of being constituted by the nucleic acid sequences SEQ ID NO: 55 and SEQ ID NO: 56, are used for measuring the expression level of the gene comprising or being constituted by the nucleic acid sequence SEQ ID NO: 16,
the pair of oligonucleotides comprising of being constituted by the nucleic acid sequences SEQ ID NO: 57 and SEQ ID NO: 58, are used for measuring the expression level of the gene comprising or being constituted by the nucleic acid sequence SEQ ID NO: 17,
the pair of oligonucleotides comprising of being constituted by the nucleic acid sequences SEQ ID NO: 59 and SEQ ID NO: 60, are used for measuring the expression level of the gene comprising or being constituted by the nucleic acid sequence SEQ ID NO: 18, the pair of oligonucleotides comprising of being constituted by the nucleic acid sequences SEQ ID NO: 61 and SEQ ID NO: 62, are used for measuring the expression level of the gene comprising or being constituted by the nucleic acid sequence SEQ ID NO: 19, the pair of oligonucleotides comprising of being constituted by the nucleic acid sequences SEQ ID NO: 63 and SEQ ID NO: 64, are used for measuring the expression level of the gene comprising or being constituted by the nucleic acid sequence SEQ ID NO: 20, the pair of oligonucleotides comprising of being constituted by the nucleic acid sequences SEQ ID NO: 65 and SEQ ID NO: 66, are used for measuring the expression level of the gene comprising or being constituted by the nucleic acid sequence SEQ ID NO: 21, the pair of oligonucleotides comprising of being constituted by the nucleic acid sequences SEQ ID NO: 67 and SEQ ID NO: 68, are used for measuring the expression level of the gene comprising or being constituted by the nucleic acid sequence SEQ ID NO: 22, the pair of oligonucleotides comprising of being constituted by the nucleic acid sequences SEQ ID NO: 69 and SEQ ID NO: 70, are used for measuring the expression level of the gene comprising or being constituted by the nucleic acid sequence SEQ ID NO: 23, the pair of oligonucleotides comprising of being constituted by the nucleic acid sequences SEQ ID NO: 71 and SEQ ID NO: 72, are used for measuring the expression level of the gene comprising or being constituted by the nucleic acid sequence SEQ ID NO: 24.

The following table 3 represents genes/variants/oligonucleotides used according to the invention.

TABLE 3

| Gene name | SEQ ID | SEQ ID variant | SEQ ID Oligo forward | SEQ ID Oligo reverse |
|---|---|---|---|---|
| GPX3 | SEQ ID NO: 1 | — | SEQ ID NO: 25 | SEQ ID NO: 26 |
| GPX1 (1) | SEQ ID NO: 2 | — | SEQ ID NO: 27 | SEQ ID NO: 28 |
| GLRX2 (2) | SEQ ID NO: 3 | — | SEQ ID NO: 29 | SEQ ID NO: 30 |
| CAT | SEQ ID NO: 4 | — | SEQ ID NO: 31 | SEQ ID NO: 32 |
| PRDX (1-2-3) | SEQ ID NO: 5 | SEQ ID NO: 73 or SEQ ID NO: 74 | SEQ ID NO: 33 | SEQ ID NO: 34 |
| PRDX5 (2) | SEQ ID NO: 6 | — | SEQ ID NO: 35 | SEQ ID NO: 36 |
| SOD2 (1-2-3) | SEQ ID NO: 7 | SEQ ID NO: 75 or SEQ ID NO: 76 | SEQ ID NO: 37 | SEQ ID NO: 38 |
| GSR (1-2-3-4) | SEQ ID NO: 8 | SEQ ID NO: 77 or SEQ ID NO: 78 or SEQ ID NO: 79 | SEQ ID NO: 39 | SEQ ID NO: 40 |
| GLRX (1-2) | SEQ ID NO: 9 | SEQ ID NO: 80 | SEQ ID NO: 41 | SEQ ID NO: 42 |
| PRDX2 (1) | SEQ ID NO: 10 | — | SEQ ID NO: 43 | SEQ ID NO: 44 |
| PRDX5 (1-3) | SEQ ID NO: 11 | SEQ ID NO: 81 or SEQ ID NO: 82 | SEQ ID NO: 45 | SEQ ID NO: 46 |
| SOD1 | SEQ ID NO: 12 | — | SEQ ID NO: 47 | SEQ ID NO: 48 |

TABLE 3-continued

| Gene name | SEQ ID | SEQ ID variant | SEQ ID Oligo forward | SEQ ID Oligo reverse |
|---|---|---|---|---|
| TXN | SEQ ID NO: 13 | — | SEQ ID NO: 49 | SEQ ID NO: 50 |
| PRDX3 (1-2) | SEQ ID NO: 14 | SEQ ID NO: 83 | SEQ ID NO: 51 | SEQ ID NO: 52 |
| GPX7 | SEQ ID NO: 15 | — | SEQ ID NO: 53 | SEQ ID NO: 54 |
| GPX4 (1-2-3) | SEQ ID NO: 16 | SEQ ID NO: 84 or SEQ ID NO: 85 | SEQ ID NO: 55 | SEQ ID NO: 56 |
| TXN2 | SEQ ID NO: 17 | — | SEQ ID NO: 57 | SEQ ID NO: 58 |
| PRDX4 | SEQ ID NO: 18 | — | SEQ ID NO: 59 | SEQ ID NO: 60 |
| GPX1 (2) | SEQ ID NO: 19 | — | SEQ ID NO: 61 | SEQ ID NO: 62 |
| GLRX3 | SEQ ID NO: 20 | — | SEQ ID NO: 63 | SEQ ID NO: 64 |
| PRDX2 (3) | SEQ ID NO: 21 | — | SEQ ID NO: 65 | SEQ ID NO: 66 |
| PRDX6 | SEQ ID NO: 22 | — | SEQ ID NO: 67 | SEQ ID NO: 68 |
| GLRX5 | SEQ ID NO: 23 | — | SEQ ID NO: 69 | SEQ ID NO: 70 |
| GLRX2 (1) | SEQ ID NO: 24 | — | SEQ ID NO: 71 | SEQ ID NO: 72 |
| GPX3 | SEQ ID NO: 1 | — | SEQ ID NO: 25 | SEQ ID NO: 26 |
| GPX1 (1) | SEQ ID NO: 2 | — | SEQ ID NO: 27 | SEQ ID NO: 28 |
| GLRX2 (2) | SEQ ID NO: 3 | — | SEQ ID NO: 29 | SEQ ID NO: 30 |
| CAT | SEQ ID NO: 4 | — | SEQ ID NO: 31 | SEQ ID NO: 32 |
| PRDX (1-2-3) | SEQ ID NO: 5 | SEQ ID NO: 73 or SEQ ID NO: 74 | SEQ ID NO: 33 | SEQ ID NO: 34 |
| PRDX5 (2) | SEQ ID NO: 6 | — | SEQ ID NO: 35 | SEQ ID NO: 36 |
| SOD2 (1-2-3) | SEQ ID NO: 7 | SEQ ID NO: 75 or SEQ ID NO: 76 | SEQ ID NO: 37 | SEQ ID NO: 38 |

The oligonucleotides defined above are preferably used for carrying out a qPCR reaction.

qPCR is well known in the art, and can be carried out by using, in association with oligonucleotides allowing a specific amplification of the target gene, either with dyes or with reporter probe.

Both techniques are briefly summarized hereafter.

Real-Time PCR with Double-Stranded DNA-Binding Dyes as Reporters:

A DNA-binding dye binds to all double-stranded (ds) DNA in PCR, causing fluorescence of the dye. An increase in DNA product during PCR therefore leads to an increase in fluorescence intensity and is measured at each cycle, thus allowing DNA concentrations to be quantified.

However, dsDNA dyes such as SYBR Green will bind to all dsDNA PCR products, including nonspecific PCR products (such as Primer dimer). This can potentially interfere with or prevent accurate quantification of the intended target sequence.

The reaction is prepared as usual, with the addition of fluorescent dsDNA dye.

The reaction is run in a Real-time PCR instrument, and after each cycle, the levels of fluorescence are measured with a detector; the dye only fluoresces when bound to the dsDNA (i.e., the PCR product). With reference to a standard dilution, the dsDNA concentration in the PCR can be determined.

Like other real-time PCR methods, the values obtained do not have absolute units associated with them (i.e., mRNA copies/cell). As described above, a comparison of a measured DNA/RNA sample to a standard dilution will only give a fraction or ratio of the sample relative to the standard, allowing only relative comparisons between different tissues or experimental conditions. To ensure accuracy in the quantification, it is usually necessary to normalize expression of a target gene to a stably expressed gene (see below). This can correct possible differences in RNA quantity or quality across experimental samples.

Fluorescent Reporter Probe Method

Fluorescent reporter probes detect only the DNA containing the probe sequence; therefore, use of the reporter probe significantly increases specificity, and enables quantification even in the presence of non-specific DNA amplification. Fluorescent probes can be used in multiplex assays—for detection of several genes in the same reaction—based on specific probes with different-coloured labels, provided that all targeted genes are amplified with similar efficiency. The specificity of fluorescent reporter probes also prevents interference of measurements caused by primer dimers, which are undesirable potential by-products in PCR. However, fluorescent reporter probes do not prevent the inhibitory effect of the primer dimers, which may depress accumulation of the desired products in the reaction.

The method relies on a DNA-based probe with a fluorescent reporter at one end and a quencher of fluorescence at the opposite end of the probe. The close proximity of the reporter to the quencher prevents detection of its fluorescence; breakdown of the probe by the 5' to 3' exonuclease activity of the Taq polymerase breaks the reporter-quencher proximity and thus allows unquenched emission of fluorescence, which can be detected after excitation with a laser. An increase in the product targeted by the reporter probe at each PCR cycle therefore causes a proportional increase in fluorescence due to the breakdown of the probe and release of the reporter.

The PCR is prepared as usual, and the reporter probe is added.

During the annealing stage of the PCR both probe and primers anneal to the DNA target.

Polymerisation of a new DNA strand is initiated from the primers, and once the polymerase reaches the probe, its 5'-3'-exonuclease degrades the probe, physically separating the fluorescent reporter from the quencher, resulting in an increase in fluorescence.

Fluorescence is detected and measured in the real-time PCR thermocycler, and its geometric increase corresponding to exponential increase of the product is used to determine the threshold cycle (CT) in each reaction.

In one particular embodiment, the measure of the expression level of the genes as defined above is achieved, in addition to the above defined specific oligonucleotides, by using a probe commercially available. Each gene for which the expression level is expected is associated with a specific probe, a probe recognizing one gene is not able to recognize another gene. Moreover a probe specific of one gene can also detect, when they exist, variants of said genes.

The advantageous probes used in the invention are listed in the table A.

The association between gene/variant/oligonucleotides and probes are represented in the following table 4.

TABLE 4

| Gene name | SEQ ID | SEQ ID variant | SEQ ID Oligo forward | SEQ ID Oligo reverse | SEQ probes |
|---|---|---|---|---|---|
| GPX3 | SEQ ID NO: 1 | — | SEQ ID NO: 25 | SEQ ID NO: 26 | CCAGCCGC |
| GPX1 (1) | SEQ ID NO: 2 | — | SEQ ID NO: 27 | SEQ ID NO: 28 | GGTGGTGG |
| GLRX2 (2) | SEQ ID NO: 3 | — | SEQ ID NO: 29 | SEQ ID NO: 30 | GGCGGCGG |
| CAT | SEQ ID NO: 4 | — | SEQ ID NO: 31 | SEQ ID NO: 32 | TGCTGGAG |
| PRDX (1-2-3) | SEQ ID NO: 5 | SEQ ID NO: 73 or SEQ ID NO: 74 | SEQ ID NO: 33 | SEQ ID NO: 34 | CTGGCTGG |
| PRDX5 (2) | SEQ ID NO: 6 | — | SEQ ID NO: 35 | SEQ ID NO: 36 | GGAAGGAG |
| SOD2 (1-2-3) | SEQ ID NO: 7 | SEQ ID NO: 75 or SEQ ID NO: 76 | SEQ ID NO: 37 | SEQ ID NO: 38 | CTGCTGGG |
| GSR (1-2-3-4) | SEQ ID NO: 8 | SEQ ID NO: 77 or SEQ ID NO: 78 or SEQ ID NO: 79 | SEQ ID NO: 39 | SEQ ID NO: 40 | GCTGGAAG |
| GLRX (1-2) | SEQ ID NO: 9 | SEQ ID NO: 80 | SEQ ID NO: 41 | SEQ ID NO: 42 | GGTGGCTG |
| PRDX2 (1) | SEQ ID NO: 10 | — | SEQ ID NO: 43 | SEQ ID NO: 44 | TGGGGAAG |
| PRDX5 (1-3) | SEQ ID NO: 11 | SEQ ID NO: 81 or SEQ ID NO: 82 | SEQ ID NO: 45 | SEQ ID NO: 46 | GGAAGGAG |
| SOD1 | SEQ ID NO: 12 | — | SEQ ID NO: 47 | SEQ ID NO: 48 | TGGGGAAG |
| TXN | SEQ ID NO: 13 | — | SEQ ID NO: 49 | SEQ ID NO: 50 | CAGCAGCC |
| PRDX3 (1-2) | SEQ ID NO: 14 | SEQ ID NO: 83 | SEQ ID NO: 51 | SEQ ID NO: 52 | CTGCTTCC |
| GPX7 | SEQ ID NO: 15 | — | SEQ ID NO: 53 | SEQ ID NO: 54 | GGAAGGAG |
| GPX4 (1-2-3) | SEQ ID NO: 16 | SEQ ID NO: 84 or SEQ ID NO: 85 | SEQ ID NO: 55 | SEQ ID NO: 56 | CTGCCCCA |
| TXN2 | SEQ ID NO: 17 | — | SEQ ID NO: 57 | SEQ ID NO: 58 | GGCCCCAG |
| PRDX4 | SEQ ID NO: 18 | — | SEQ ID NO: 59 | SEQ ID NO: 60 | ACTGGGAA |
| GPX1 (2) | SEQ ID NO: 19 | — | SEQ ID NO: 61 | SEQ ID NO: 62 | CTCCTCCT |
| GLRX3 | SEQ ID NO: 20 | — | SEQ ID NO: 63 | SEQ ID NO: 64 | TGGTGGAA |
| PRDX2 (3) | SEQ ID NO: 21 | — | SEQ ID NO: 65 | SEQ ID NO: 66 | GGAGGCTG |
| PRDX6 | SEQ ID NO: 22 | — | SEQ ID NO: 67 | SEQ ID NO: 68 | CCTGGAGC |
| GLRX5 | SEQ ID NO: 23 | — | SEQ ID NO: 69 | SEQ ID NO: 70 | TGCTGGAG |
| GLRX2 (1) | SEQ ID NO: 24 | — | SEQ ID NO: 71 | SEQ ID NO: 72 | GGATGGAG |

Table 4 can be read as follows: The expression level of GPX3 (SEQ ID NO: 1) can be quantitatively measured by using the oligonucleotides SEQ ID NO: 24 and 25, and using as probe, coupled with a fluorescent dye and a quencher, having the following sequence CCAGCCGC.

Also, another example: The expression level of PDRX (SEQ ID NO: 5), or one of its variants (SEQ ID NO 73 or 74) can be quantitatively measured by using the oligonucleotides SEQ ID NO: 33 and 34, and using as probe, coupled with a fluorescent dye and a quencher, having the following sequence CTGGCTGG.

The above definitions apply mutatis mutandis for the other genes.

Quencher and dye mentioned above can be chosen by the skilled person, depending of the assay.

In another advantageous embodiment, the invention relates to the method as defined above, using at least one of the oligonucleotide allowing the measurement of the expression level of each of at least 6 genes comprising or being constituted by the nucleic acid sequences SEQ ID NO: 1-6, preferably using at least one of the oligonucleotide allowing the measurement of the expression level of each of at least 10 genes comprising or being constituted by the nucleic acid sequences SEQ ID NO: 1-10, in particular using at least one of the oligonucleotide allowing the measurement of the expression level of each of the 24 genes comprising or being constituted by the nucleic acid sequences SEQ ID NO: 1-24.

In this embodiment, the method is adapted for northern blot assay.

The invention also relates to a composition comprising oligonucleotides allowing the measure of the expression of at least the genes of a sub-group of 6 genes belonging to a set of genes chosen among a group of 24 genes, said group of 24 genes comprising or being constituted by the nucleic acid sequences SEQ ID NO:1 to 24, said 6 genes belonging to said sub-group comprising or being constituted by the nucleic acid sequences SEQ ID NO: 1 to 6.

In one advantageous embodiment, the invention relates to a composition as defined above, comprising oligonucleotides allowing the measure of the expression of at least the genes of a set of 10 genes chosen among a group of 24 genes, said group of 24 genes comprising or being constituted by the nucleic acid sequences SEQ ID NO:1 to 24, said 10 genes belonging to said set comprising or being constituted by the nucleic acid sequences SEQ ID NO: 1 to 10.

In one other advantageous embodiment, the invention relates to a composition as defined above, comprising oligonucleotides allowing the measure of the expression of the 24 of said group of 24 genes.

In one other advantageous embodiment, the invention relates to a composition as defined above, said composition comprising at least 12 oligonucleotides chosen among a library of 48 oligonucleotides comprising or consisting of the nucleic acid sequences SEQ ID NO: 25-72, allowing the measure of the expression of at least the genes of a sub-group of 6 genes belonging to a set of genes chosen among a group of 24 genes comprising or being constituted by the nucleic acid sequences SEQ ID NO:1 to 24, said at least 12 oligonucleotides comprising or consisting of the nucleic acid sequences SEQ ID NO: 25-36.

In one other advantageous embodiment, the invention relates to a composition as defined above, said composition comprising at least 20 oligonucleotides chosen among a library of 48 oligonucleotides comprising or consisting of the nucleic acid sequences SEQ ID NO: 25-72, allowing the measure of the expression of at least the genes a set of 10 genes chosen among a group of 24 genes comprising or being constituted by the nucleic acid sequences SEQ ID NO:1 to 24, said at least 20 oligonucleotides comprising or consisting of the nucleic acid sequences SEQ ID NO: 25-44.

In one other advantageous embodiment, the invention relates to a composition as defined above, said composition comprising 48 oligonucleotides comprising or consisting of the nucleic acid sequences SEQ ID NO: 25-72, allowing the measure of the expression of a group of 24 genes comprising or being constituted by the nucleic acid sequences SEQ ID NO:1 to 24.

The above composition may further comprise probes as defined above in Table 4.

In another aspect, the invention relates to the composition as mentioned above, for its use for the diagnosis, and/or the classification, preferably in vitro, of an hematological disorder, in particular myeloid and/or lymphoid hematological disorder, preferably myeloid hematological disorder.

Therefore, the invention relates to the above composition per se, and relates to said composition for its use as mentioned above.

The invention relates to a kit comprising at least 12 oligonucleotides chosen among a group of 48 oligonucleotides comprising or consisting of the nucleic acid sequences SEQ ID NO: 25-72, said at least 12 oligonucleotides comprising or consisting of the nucleic acid sequences SEQ ID NO: 25-36.

In one advantageous embodiment, the invention relates to the kit as defined above, comprising at least 20 oligonucleotides, said at least 20 oligonucleotides comprising or consisting of the nucleic acid sequences SEQ ID NO: 25-44.

In one advantageous embodiment, the invention relates to a kit as defined above comprising 48 oligonucleotides comprising or consisting of the nucleic acid sequences SEQ ID NO: 25-72.

The invention also relates to, in one advantageous embodiment, a kit as defined above, further comprising at least 6 specific probes that respectively interact the nucleic acid molecules comprising or consisting of SEQ ID NO: 1-6, preferably further comprising at least 10 specific probes that respectively interact the nucleic acid molecules comprising or consisting of SEQ ID NO: 1-10, in particular further comprising at least 24 specific probes that respectively interact the nucleic acid molecules comprising or consisting of SEQ ID NO: 1-24.

In one another advantageous embodiment, the invention relates to a kit as defined above, further comprising nucleic acid molecules corresponding to the genes SEQ ID NO: 1-24, in an amount representative at least one pathology chosen among: acute myeloid leukemia (AML), refractory anemia with ringed sideroblasts (RARS), refractory cytopenia with multilineage dysplasia (RCMD), refractory anemia with excess of blasts (RAEB) or 5q-syndrome and unclassifiable myelodysplasia.

In another advantageous embodiment, the invention also relates to the kit as defined above, further comprising nucleic acid molecules of a control sample as defined above.

The invention also relates to a positive control sample comprising or being constituted by at least the nucleic acid molecules corresponding to the genes represented by SEQ ID NO: 1-6, chosen among the group of 24 genes represented by SEQ ID NO: 1-24, said nucleic acid molecules being present in said sample in an amount as represented in the 6 first lines of table 5 or table 6, compared to an healthy sample in which each of the respective nucleic acid molecules are present in an amount of 1.

TABLE 5

Table 5

| | RARS | RCMD | RAEB | AML |
|---|---|---|---|---|
| SEQ ID NO: 1 | 1.32-2.62 | 0.01-1.67 | 0.43-2.88 | 0.03-0.30 |
| SEQ ID NO: 2 | 2.32-2.98 | 0.12-9.95 | 4.48-18.89 | 2.98-6.98 |
| SEQ ID NO: 3 | 3.74-9.79 | 0.08-10.50 | 0.14-10.87 | 3.12-15.80 |
| SEQ ID NO: 4 | 1.28-2.20 | 0.02-3.94 | 0.99-8.75 | 0.32-10.20 |
| SEQ ID NO: 5 | 1.25-3.68 | 0.18-5.77 | 4.59-10.04 | 2.00-13.34 |
| SEQ ID NO: 6 | 1.84-6.09 | 0.00-10.24 | 0.05-5.53 | 1.72-5.56 |

TABLE 5-continued

Table 5

| | RARS | RCMD | RAEB | AML |
|---|---|---|---|---|
| SEQ ID NO: 7 | 0.65-0.95 | 0.54-4.37 | 0.85-2.13 | 0.08-0.79 |
| SEQ ID NO: 8 | 0.67-1.09 | 0.00-1.18 | 0.44-1.15 | 0.20-0.58 |
| SEQ ID NO: 9 | 0.90-1.25 | 0.43-2.05 | 0.07-1.05 | 0.08-0.79 |
| SEQ ID NO: 10 | 0.48-1.87 | 0.02-2.13 | 0.49-4.41 | 0.04-0.25 |
| SEQ ID NO: 11 | 0.81-1.69 | 0.00-2.01 | 1.19-1.47 | 0.65-1.76 |
| SEQ ID NO: 12 | 0.64-2.12 | 0.23-3.74 | 1.48-2.74 | 0.45-2.94 |
| SEQ ID NO: 13 | 0.96-2.43 | 0.63-4.99 | 1.14-4.22 | 0.42-5.34 |
| SEQ ID NO: 14 | 1.20-2.02 | 0.16-3.16 | 0.63-1.47 | 0.70-2.15 |
| SEQ ID NO: 15 | 0.63-1.44 | 0.09-1.18 | 0.00-1.37 | 0.55-3.71 |
| SEQ ID NO: 16 | 0.94-2.53 | 0.10-3.29 | 2.58-6.22 | 1.35-4.25 |
| SEQ ID NO: 17 | 1.07-2.22 | 0.15-2.58 | 2.30-2.85 | 0.90-3.89 |
| SEQ ID NO: 18 | 1.48-2.79 | 0.37-2.86 | 3.31-4.99 | 1.10-6.67 |
| SEQ ID NO: 19 | 1.04-5.32 | 0.49-3.87 | 1.96-8.77 | 0.64-5.18 |
| SEQ ID NO: 20 | 1.49-5.23 | 0.09-2.58 | 1.81-11.93 | 0.84-7.09 |
| SEQ ID NO: 21 | 0.93-8.83 | 0.01-2.87 | 0.15-3.76 | 0.08-0.63 |
| SEQ ID NO: 22 | 0.81-3.63 | 0.14-36.64 | 0.25-12.98 | 0.98-5.93 |
| SEQ ID NO: 23 | 1.47-3.45 | 0.19-7.04 | 2.80-53.30 | 0.26-3.65 |
| SEQ ID NO: 24 | 0.78-2.25 | 0.35-1.60 | 0.40-0.87 | 0.18-0.83 |

Table 5 represents, for each gene of SEQ ID NO: 1-24, the specific interval corresponding to the mentioned pathology.

TABLE 6

Table 6

| | RARS | RCMD | RAEB | AML |
|---|---|---|---|---|
| SEQ ID NO: 1 | 2.14 ± 0.71 | 0.76 ± 0.56 | 1.60 ± 1.23 | 0.16 ± 0.13 |
| SEQ ID NO: 2 | 2.64 ± 0.33 | 3.65 ± 3.95 | 18.89 ± 17.93 | 4.95 ± 1.70 |
| SEQ ID NO: 3 | 5.97 ± 3.33 | 4.04 ± 3.49 | 5.47 ± 5.36 | 9.73 ± 5.24 |
| SEQ ID NO: 4 | 1.63 ± 0.50 | 1.46 ± 1.64 | 4.31 ± 4.00 | 4.01 ± 3.73 |
| SEQ ID NO: 5 | 2.52 ± 1.22 | 1.89 ± 2.14 | 7.40 ± 2.73 | 5.03 ± 4.74 |
| SEQ ID NO: 6 | 4.55 ± 2.36 | 3.64 ± 4.01 | 5.30 ± 5.13 | 4.19 ± 1.67 |
| SEQ ID NO: 7 | 0.84 ± 0.17 | 1.80 ± 1.61 | 1.32 ± 0.70 | 0.33 ± 0.27 |
| SEQ ID NO: 8 | 0.85 ± 0.22 | 0.76 ± 0.42 | 0.78 ± 0.35 | 0.40 ± 0.18 |
| SEQ ID NO: 9 | 1.07 ± 0.18 | 1.22 ± 0.67 | 0.54 ± 0.49 | 0.45 ± 0.26 |
| SEQ ID NO: 10 | 1.06 ± 0.72 | 0.74 ± 0.73 | 2.40 ± 1.96 | 0.11 ± 0.08 |
| SEQ ID NO: 11 | 1.33 ± 0.46 | 0.93 ± 0.83 | 1.47 ± 0.29 | 1.11 ± 0.44 |
| SEQ ID NO: 12 | 1.31 ± 0.75 | 1.12 ± 1.30 | 1.92 ± 0.71 | 1.27 ± 0.97 |
| SEQ ID NO: 13 | 1.51 ± 0.80 | 2.06 ± 1.70 | 2.32 ± 1.67 | 2.52 ± 1.87 |
| SEQ ID NO: 14 | 1.68 ± 0.43 | 1.64 ± 1.21 | 1.17 ± 0.46 | 1.70 ± 0.59 |
| SEQ ID NO: 15 | 0.99 ± 0.41 | 0.79 ± 0.39 | 0.70 ± 0.68 | 2.57 ± 1.32 |
| SEQ ID NO: 16 | 1.61 ± 0.82 | 1.58 ± 1.28 | 6.22 ± 4.17 | 2.62 ± 1.37 |
| SEQ ID NO: 17 | 1.69 ± 0.58 | 1.15 ± 0.96 | 2.79 ± 0.47 | 2.40 ± 1.33 |
| SEQ ID NO: 18 | 2.17 ± 0.65 | 1.19 ± 0.88 | 4.36 ± 0.91 | 2.59 ± 2.33 |
| SEQ ID NO: 19 | 2.59 ± 2.37 | 1.67 ± 1.25 | 4.89 ± 3.50 | 2.12 ± 1.80 |
| SEQ ID NO: 20 | 2.75 ± 2.15 | 1.27 ± 1.12 | 5.31 ± 5.74 | 3.96 ± 2.61 |
| SEQ ID NO: 21 | 3.80 ± 4.37 | 1.38 ± 1.18 | 2.41 ± 1.97 | 0.36 ± 0.23 |
| SEQ ID NO: 22 | 1.83 ± 1.56 | 7.33 ± 14.42 | 5.69 ± 6.56 | 2.90 ± 2.21 |
| SEQ ID NO: 23 | 2.76 ± 1.12 | 2.60 ± 2.88 | 21.67 ± 27.56 | 1.49 ± 1.34 |
| SEQ ID NO: 24 | 1.56 ± 0.74 | 0.95 ± 0.46 | 0.87 ± 0.62 | 0.41 ± 0.25 |

Table 6 represents, for each gene of SEQ ID NO: 1-24, the mean±the standard deviation corresponding to the mentioned pathology.

The invention also relates to a method for determining the efficacy of a treatment of an hematological disorder, said treatment being liable to be administered to a patient, said method comprising a). a step of contacting, preferably in vitro, a biological sample of a subject afflicted by an hematological disorder, preferably a myeloid and/or a lymphoid hematological disorder, more preferably myeloid hematological disorder, with a drug liable to be used to treat, or liable to treat, said hematological disorder, b). a step of measuring, in the biological sample contacted with a drug in step a)., the expression level of at least the genes of a sub-group of 6 genes belonging to a set of genes chosen among a group of 24 genes, said group of 24 genes comprising or being constituted by the nucleic acid sequences SEQ ID NO:1 to 24, said 6 genes belonging to said sub-group comprising or being constituted by the nucleic acid sequences SEQ ID NO: 1 to 6, and c). a step of comparing the expression level of said at least the genes of a sub-group of 6 genes belonging to a set of genes chosen among a group of 24 genes obtained in step b). with the expression level of said at least the genes of a sub-group of 6 genes belonging to a set of genes chosen among a group of 24 genes obtained measured in said biological sample which has not been contacted with said drug liable to be used to treat, or liable to treat, said hematological disorder.

The above method is easy to carry out, and allows to evaluate the AML sample susceptibility to a drug. This is very important to reduce the cost of treatments, that can be ineffective in patient, because the tumor is resistant to the drug.

The above method is advantageously used to screen, in vitro, drugs having an effect on AML progression, and that could be used in vivo for the treatment of the patient.

This is more advantageous important for screening drugs, or compounds that are able to modulate the epigenetic modification, in particular demethylating agents such as azacytidine (5-azacytidine) or decitabine (5-azadeoxycytidine).

Azacytidine and decitabine are powerful chemotherapeutic agents used for treating AML and high grade MDS, but only about 30% of AML and high grade MDS are sensitive to their effects. Thus, in order to reduce the costs, and the side effects of ineffective treatment, it is advantageous to verify in vitro, if the AML and high grade MDS that has to be treated is responsive to these compounds.

The example 9 shows that the treatment of AML sample with azacytidine can modulate the expression ratio of the genes SEQ ID NO: 1-24, (and consequently at the genes SEQ ID NO: 1-6) demonstrating that azacytidine, in this particular patient from which the AML sample derives, would be effective if it is used in vivo.

Advantageously, the invention relates to a method as defined above, wherein said set consists of 10 genes consisting of the nucleic acid sequences SEQ ID NO: 1-10.

Advantageously, the invention relates to a method as defined above, the expression level of the 24 genes consisting of SEQ ID NO: 1-24 is measured.

LEGEND OF THE FIGURES

FIG. 1 represents the natural mechanism used in cell for eliminating reactive oxide species (ROS, $O_2^{\bullet-}$). $O_2^{\bullet-}$ were converted into $H_2O_2$ molecules, said $H_2O_2$ being themselves either converted into $H_2O$ and $O_2$ as a detoxifying process, or into $^{\bullet}OH$ and $OH^-$ that exert biological effects in cells.

FIG. 2 represents the imbrications between the subgroup (A), the set (B) and the group (C) of the genes according to the invention. D represents the ensemble corresponding to the genes belonging to the set but that do not belong to the sub-group. E represents the ensemble corresponding to the genes belonging to the group but that do not belong to the set.

FIGS. 3 A-E represent the schematic representation of the expression level of each genes represented by SEQ ID NO: 1-24, for each pathologies: RARS, RCMD, RAEB and AML.

FIG. 3A represents an histogram showing the expression level of the genes indicated in the x-axis, obtained by qRT-PCR, compared to the housekeeping gene GAPDH, by using 5 healthy bone marrow samples (control sample).

Y-axis represents the ratio $\Delta CT_{gene}$ ($\Delta CT_{gene} = CT_{gene} - CT_{GAPDH}$).

Figures 4A, 4B, 4C, 4D:
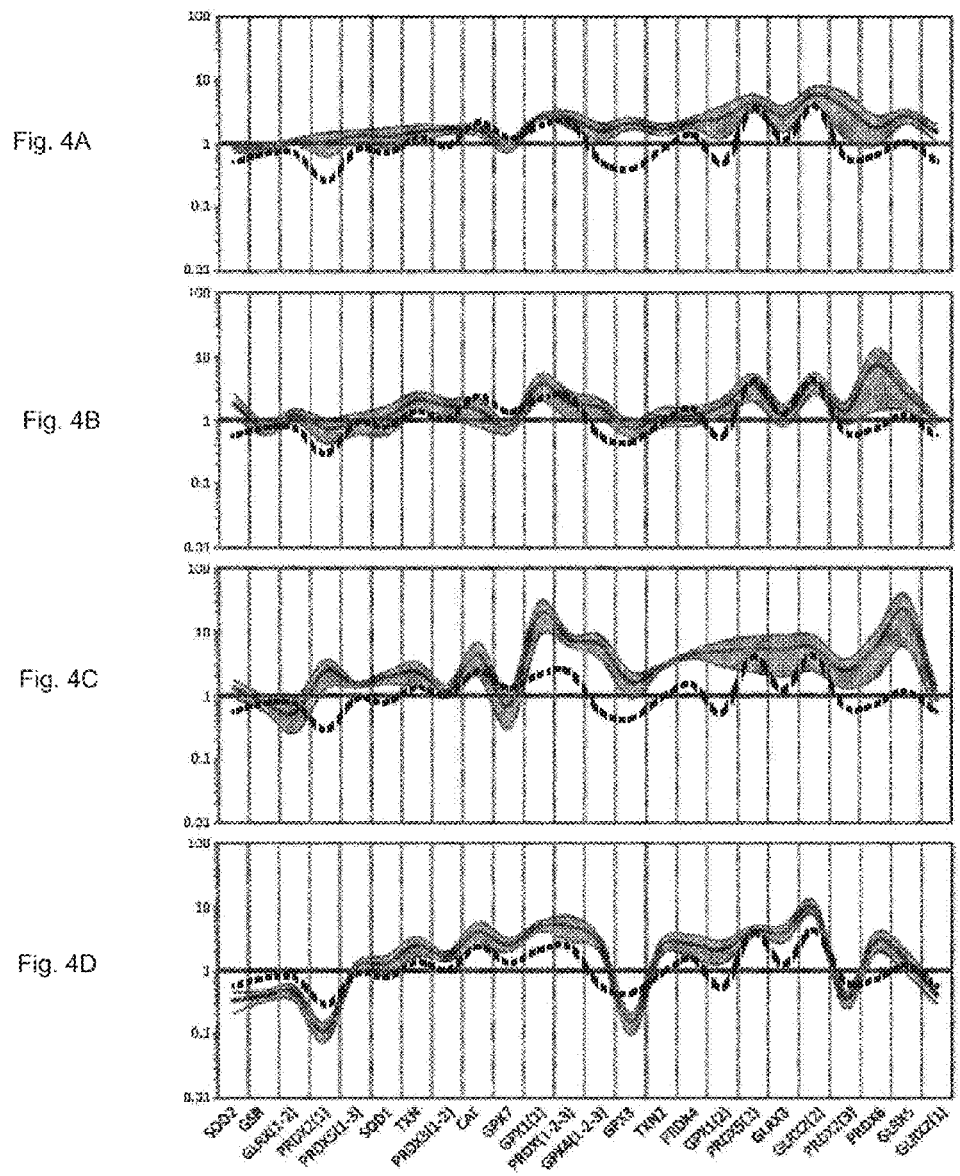

FIGS. 4A-D represent the schematic representation of the expression level of each of the genes represented by SEQ ID NO: 1-24, for each pathologies: RARS (FIG. 4A), RCMD (FIG. 4B), RAEB (FIG. 4C) and AML (FIG. 4D). Representation of the expression level of each genes represented by SEQ ID NO: 1-24 of an unclassifiable myelodysplastic syndroma sample is represented in each FIGS. 4A-D by hashed line.

FIGS. 5A and B represent the schematic representation of the expression level of each of the genes represented by SEQ ID NO: 1-24 of two independent unclassifiable myelodysplastic syndroma samples (FIG. 5B), said expression being similar to the expression level observed in RCMD samples (FIG. 5A)

FIG. 6 represents the schematic representation of the expression level of each of the genes represented by SEQ ID NO: 1-24 of two independent chronic myelomonocytic leukemia samples (FIG. 6B) said expression being different from the expression level observed in RAEB samples (FIG. 6A)

Figure 7:
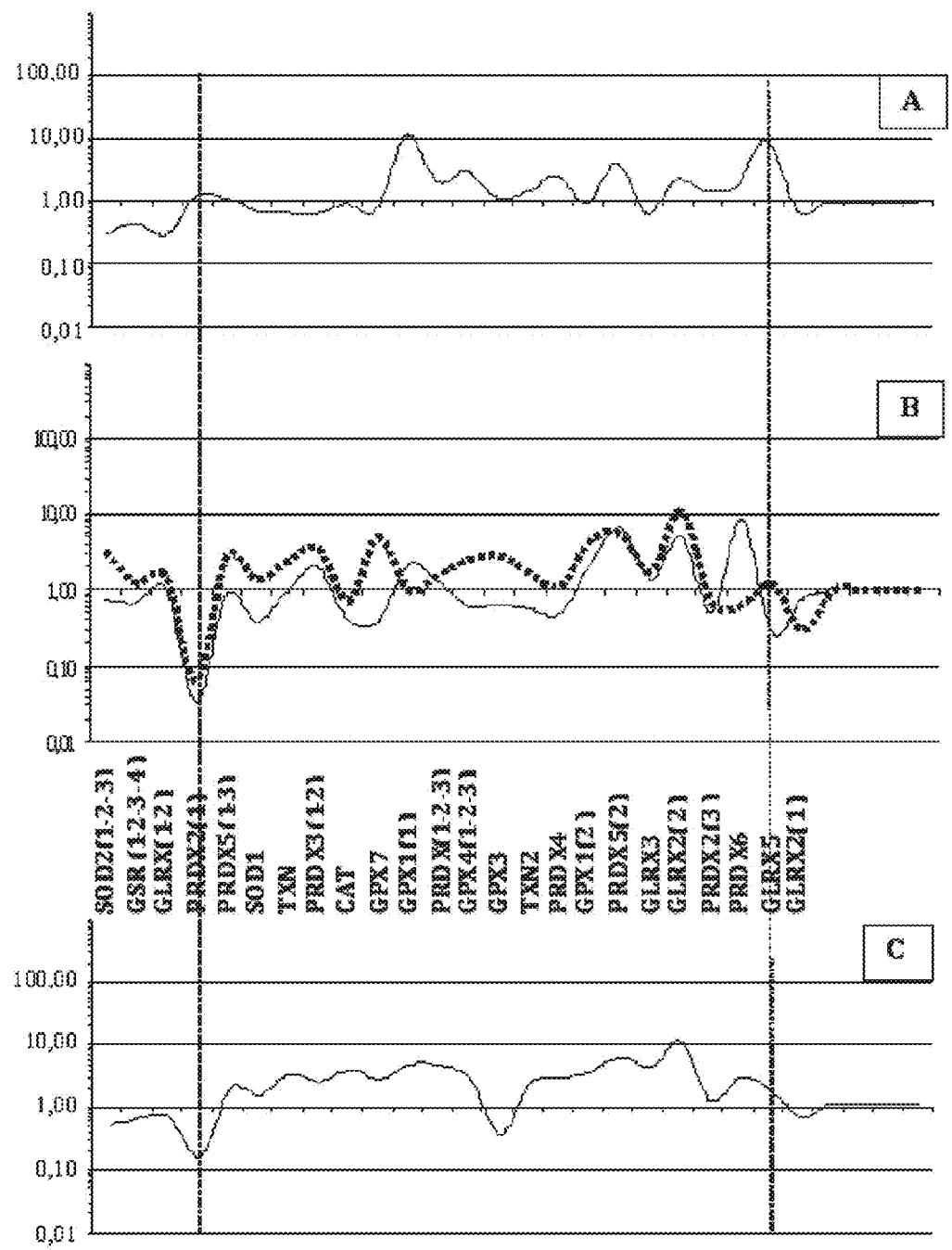

FIG. 7 represents the schematic representation of the expression level of each of the genes represented by SEQ ID NO: 1-24 of a patient at diagnosis of RCMD (panel B) and after 12 months (panel B, hatched line). The sample at diagnosis is similar to RCMD sample (panel A) and the sample after 12 months has acquired characteristics of RAEB (see PDRX2(1) and GLRX5 in panel B and panel C).

Figure 8:
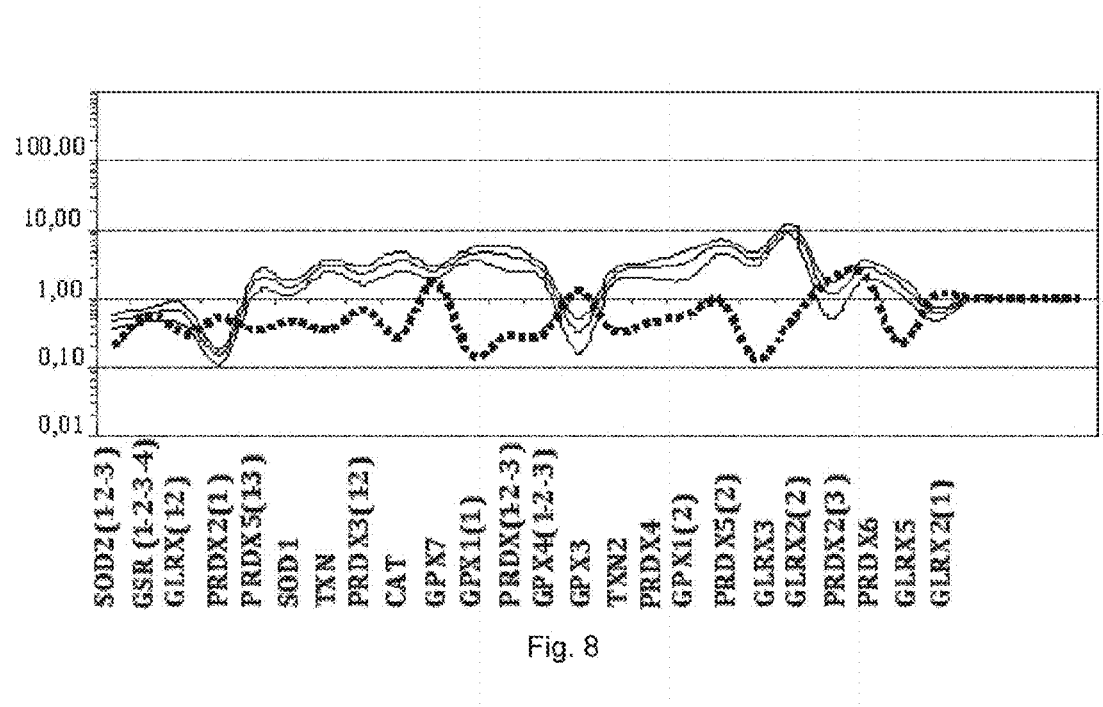

FIG. 8 represents the schematic representation of the expression level of each of the genes represented by SEQ ID NO: 1-24 of AML, compared to same AML after treatment with azacytidine (hatched line).

EXAMPLES

Preliminary Comment

All the samples used in the following examples have been first tested according to the invention, in a blind test, and compared with control samples.

All the SMD and leukemic samples satisfy the provisions of the method according to the invention, i.e. in each of the samples at least 3 genes of the genes SEQ ID NO: 1-6 are expressed such that their ratio compared to the expression of the same corresponding genes in control samples is either lower than 0.5 or higher to 2.

Example 1

In the following examples, the patient's samples and the analysis genes expressions are analysed as follows.

Material and Methods

Sample Harvest

Normal bone marrow (BM) samples (used as a reference) were obtained from patients undergoing orthopedic surgery. Bone marrow samples from MDS and AML patients were obtained at the time of diagnosis and during the follow up. AML and MDS cells were classified according to morphological, cytochemical and cytogenetical findings. Patients were informed and consenting following a procedure approved by the ethical committee. BM samples were aspirated into heparinized syringes and transferred to EDTA tubes.

Erythrocyte Lysis

Lysis was performed in 47 mL lysis buffer containing EDTA (0.12 mM), potassium bicarbonate ($KHCO_3$) (10 mM), and ammonium chloride ($NH_4Cl$) (150 mM) for 3 mL of BM. Following incubation at room temperature for 15 min, cells were centrifuged at 700 g for 10 min, and washed, twice, in 20 mL of Phosphate Buffered Saline (PBS) (Invitrogen). The pellet was resuspended in Trizol® (Invitrogen) (1 mL/8.10⁶ cells), mixed vigorously for 15 minutes. The lysate was stored at −80° C. until the RNA extraction step.

RNA Extraction

Total RNA extraction was performed according to the chloroform/isopropanol/ethanol method. The phase separation was obtained by adding chloroform (0.2 mL per 1 mL of TRIzol® purchased from Invitrogen) to the lysate. After mixing for 50 sec, the solution was separated into three phases by centrifugation at 12,000 g for 15 min at 4° C. RNA was precipitated, from the aqueous phase, by adding isopropanol (0.5 mL per 1 mL of TRIzol®). Following incubation at room temperature for 10 min and centrifugation at 12,000 g for 10 min at 4° C., RNA was washed in 75% ethanol (1 mL per 1 mL of TRIzol®) and centrifugated at 7500 g for 5 min at 4° C. This step was performed twice. After removing ethanol supernatant, the RNA pellet was air-dried for 20 min. Then, RNA was dissolved in 50 μL of UltraPure™ DEPC-treated water (Invitrogen) and stored at −80° C.

RNA Quantification and Qualification

Total cellular RNA was quantified using a Nano-Drop 1000 spectrophotometer (Nano-Drop Technologies) and RNA purity was analyzed using an Agilent 2100 Bioanalyzer (Agilent Technologies).

Reverse Transcription and Quantitative Real-Time PCR (qRT-PCR) Analysis

Three micrograms of total RNA from each sample were reverse transcribed using the SuperScript® VILO™ cDNA Synthesis kit (Invitrogen) according to the protocol of the supplier. The relative quantification of gene expression was done by real-time PCR on the LightCycler® 480 microwell plate-based cycler platform (Roche Applied Science) using Universal ProbeLibrary assays designed with the ProbeFinder software (Roche Applied Science, www.roche-applied-science.com/sis/rtper/upl/ezhome.html). Primers were purchased from Invitrogen and Universal ProbeLibrary probes from Roche Applied Science. The nucleotide sequences of the primers and probes of each target are shown in Table A. All targets were concomitantly analyzed. qRT-PCR reactions were carried out in a total volume of 10 μL on 20 ng of cDNA using LightCycler® 480 Probes Master (Roche Applied Science). The LightCycler® 480 was programmed to an initial denaturation (95° C., 10 min) following by 45 cycles of 10 sec at 95° C., 30 sec at 60° C., 1 sec at 72° C. and a final cooling step at 40° C. for 10 sec. All reactions were run in triplicate, and average values were used for quantification. Results were analyzed by the relative quantification method ($\Delta\Delta CT = \Delta CT_{patient} - \Delta CT_{reference}$) using the Cycle threshold (CT) values determined with the LightCycler® 480 software (release 1.5.0) from Roche Applied Science. The human glyceraldehyde-3-phosphate dehydrogenase gene (GAPDH) was used as the endogenous control to normalize the expression of the target ($\Delta CT = CT_{target} - CT_{endogenous\ control}$). Change of relative mRNA expression between a patient and the reference was determined for each target using the 2exp(−ΔΔCT) method (Livak K J and Schmittgen T D. Analysis of relative gene expression data using real time quantitative PCR and the 2exp(−ΔΔCT) method. *Methods* 2001; 25:402-408).

Example 2

Use of 6 Genes for Diagnosing Myelodysplasia and Leukemia

In order to test the validity of the method, patient samples identified as representative of leukemic samples where used, and the expression level of each of the genes represented by SEQ ID NO: 1 to SEQ ID NO: 6 was evaluated by RT-qPCR as disclosed in Example 1, by using oligonucleotides and probes of the Table 4.

The results are represented in the following table 7:

TABLE 7

|  | AML # 1 | AML # 2 | AML # 3 | AML # 4 | AML # 5 |
|---|---|---|---|---|---|
| SEQ ID NO: 1 | 0.03 | 0.29 | 0.30 | 0.08 | 0.08 |
| SEQ ID NO: 2 | 3.54 | 6.16 | 6.98 | 2.98 | 5.10 |
| SEQ ID NO: 3 | 14.24 | 7.07 | 8.41 | 15.80 | 3.12 |
| SEQ ID NO: 4 | 10.20 | 4.06 | 3.32 | 2.17 | 0.32 |
| SEQ ID NO: 5 | 13.34 | 2.96 | 2.00 | 4.46 | 2.36 |
| SEQ ID NO: 6 | 5.56 | 3.22 | 5.12 | 5.34 | 1.72 |

Table 7 represents the ratio of the expression level of each indicated genes (SEQ ID NO: 1-6) for each AML sample #1-#5

The criterions defined in the invention are satisfied:

A sample is considered as representative of an hematological disorder when the ratio of the expression level of each genes of any combination of 3 genes among the genes represented by SEQ ID NO: 1-6 is either ≥2.0 or ≤0.5.

Whatever the combination of 3 genes taken in consideration, the above criterions are satisfied.

The other criterion is that: if ratio of SEQ ID NO: 1 is ≤0.3 and the ratio of both SEQ ID NO: 2 and 3 are ≥3.0, the sample is representative of an AML.

Again, for all the 5 above AML samples tested (Table 7), the criterions are satisfied.

All the tested samples satisfy the criterions regarding AML. Therefore, the method according to the invention allows the discrimination between AML and myelodysplastic disorders.

Example 3

Validation of the Method with Leukemic Cell Lines

In order to validate the method, the expression level of the genes represented by SEQ ID NO: 1-6 was evaluated in 11 cell lines corresponding to almost all the AML subtypes defined according to the FAB classification.

The following cell lines have been tested:

KG1a and KG1 (FAB M0/M1), HL60 (FAB M2), KASUMI-1 (FAB M2), ML-2 (FAB M4), MV4-11 (FAB M5), THP-1 (FAB M5), U937 (FAB M5), K562 (FAB M6), TF-1 (FAB M6) and UT7 (FAB M7).

The expression levels are indicated in the following table 8.

TABLE 8

| SEQ ID NO: | KG1a | KG1 | HL60 | Kasumi-1 | ML-2 | MV4-11 | THP-1 | U937 | K562 | TF-1 | UT7 |
|---|---|---|---|---|---|---|---|---|---|---|---|
| 1 | 0.05 | 006 | 0.05 | 0.04 | 0.06 | 0.03 | 0.15 | 0.07 | 0.10 | 0.03 | 0.30 |
| 2 | 3.42 | 5.26 | 4.74 | 6.23 | 5.61 | 17.95 | 45.70 | 12.20 | 4.58 | 7.92 | 48.90 |

TABLE 8-continued

| SEQ ID NO: | KG1a | KG1 | HL60 | Kasumi-1 | ML-2 | MV4-11 | THP-1 | U937 | K562 | TF-1 | UT7 |
|---|---|---|---|---|---|---|---|---|---|---|---|
| 3 | 37.71 | 54.38 | 33.49 | 14.34 | 34.17 | 17.19 | 77.40 | 45.84 | 69.24 | 18.38 | 53.66 |
| 4 | 0.53 | 0.91 | 2.73 | 1.25 | 2.13 | 5.19 | 8.80 | 1.91 | 2.08 | 1.54 | 2.44 |
| 5 | 197.83 | 39.98 | 14.21 | 9.46 | 6.10 | 8.08 | 29.76 | 17.93 | 48.00 | 31.97 | 33.70 |
| 6 | 30.91 | 32.92 | 13.85 | 12.11 | 9.14 | 5.84 | 20.37 | 10.29 | 24.11 | 13.99 | 30.32 |

Table 8 represents the ratios $R_i$ between the expression levels of the indicated gene in the corresponding cell line, compared to the expression levels of the corresponding gene in control samples (healthy bone marrow samples).

The criterions defined in the invention as satisfied:

A sample is considered as representative of an hematological disorder when the ratio of the expression level of each genes of any combination of 3 genes among the genes represented by SEQ ID NO: 1-6 is either $\geq 2.0$ or $\leq 0.5$.

Whatever the combination of 3 genes taken in consideration, the above criterions are satisfied.

The other criterion is that: if ratio of SEQ ID NO: 1 is $\leq 0.3$ and the ratio of both SEQ ID NO: 2 and 3 are $\geq 3.0$, the sample is representative of an AML.

Again, for all the 11 above cell lines tested (Table 3), the criterions are satisfied, and the method confirm that these results obtained with this cell lines correspond to those obtained with primary leukemic cells.

Example 4

Classification of Myelodyplastic Sample

As defined above, it has been proposed that the measure of the expression level of the genes represented by SEQ ID NO: 1-24 allows to identify subtype of myelodysplastic syndrome.

A panel of patient sample, classified by other techniques, has been tested to validate the method according to the invention.

3 RARS, 6 RCMD and 3 RAEB have been used, and the expression level of the genes represented by SEQ ID NO: 1-24 have been evaluated.

Results are presented hereafter:

TABLE 9

| | RARS #1 | RARS #2 | RARS #3 |
|---|---|---|---|
| SEQ ID NO: 1 | 2.48 | 1.32 | 2.62 |
| SEQ ID NO: 2 | 2.63 | 2.32 | 2.98 |
| SEQ ID NO: 3 | 9.79 | 3.74 | 4.38 |
| SEQ ID NO: 4 | 2.20 | 1.41 | 1.28 |
| SEQ ID NO: 5 | 3.68 | 2.64 | 1.25 |
| SEQ ID NO: 6 | 5.72 | 6.09 | 1.84 |
| SEQ ID NO: 7 | 0.65 | 0.93 | 0.95 |
| SEQ ID NO: 8 | 1.09 | 0.79 | 0.67 |
| SEQ ID NO: 9 | 1.25 | 1.06 | 0.90 |
| SEQ ID NO: 10 | 1.87 | 0.48 | 0.82 |
| SEQ ID NO: 11 | 1.69 | 1.50 | 0.81 |
| SEQ ID NO: 12 | 2.12 | 0.64 | 1.17 |
| SEQ ID NO: 13 | 2.43 | 1.16 | 0.96 |
| SEQ ID NO: 14 | 2.02 | 1.82 | 1.20 |
| SEQ ID NO: 15 | 1.44 | 0.89 | 0.63 |
| SEQ ID NO: 16 | 2.53 | 1.35 | 0.94 |
| SEQ ID NO: 17 | 2.22 | 1.07 | 1.79 |
| SEQ ID NO: 18 | 2.79 | 2.25 | 1.48 |
| SEQ ID NO: 19 | 1.43 | 5.32 | 1.04 |
| SEQ ID NO: 20 | 5.23 | 1.49 | 1.53 |

TABLE 9-continued

| | RARS #1 | RARS #2 | RARS #3 |
|---|---|---|---|
| SEQ ID NO: 21 | 1.64 | 8.83 | 0.93 |
| SEQ ID NO: 22 | 3.63 | 1.06 | 0.81 |
| SEQ ID NO: 23 | 3.35 | 3.45 | 1.47 |
| SEQ ID NO: 24 | 1.64 | 0.78 | 2.25 |

Table 9: RARS samples

TABLE 10

Table 10: RCMD samples

| | RCMD #1 | RCMD #2 | RCMD #3 | RCMD #4 | RCMD #4 | RCMD #5 |
|---|---|---|---|---|---|---|
| SEQ ID NO: 1 | 0.55 | 1.05 | 1.67 | 0.66 | 0.61 | 0.01 |
| SEQ ID NO: 2 | 0.52 | 9.95 | 5.75 | 0.54 | 0.12 | 5.05 |
| SEQ ID NO: 3 | 3.44 | 4.57 | 10.50 | 2.71 | 0.08 | 2.96 |
| SEQ ID NO: 4 | 2.07 | 2.53 | 3.94 | 0.06 | 0.02 | 0.13 |
| SEQ ID NO: 5 | 2.43 | 5.77 | 2.23 | 0.48 | 0.18 | 0.28 |
| SEQ ID NO: 6 | 3.96 | 6.09 | 10.24 | 1.46 | 0.10 | 0.00 |
| SEQ ID NO: 7 | 0.58 | 3.22 | 4.37 | 1.27 | 0.54 | 0.82 |
| SEQ ID NO: 8 | 0.91 | 1.05 | 1.18 | 0.84 | 0.57 | 0.00 |
| SEQ ID NO: 9 | 1.48 | 2.05 | 1.86 | 0.88 | 0.62 | 0.43 |
| SEQ ID NO: 10 | 0.68 | 2.13 | 0.75 | 0.31 | 0.53 | 0.02 |
| SEQ ID NO: 11 | 0.71 | 2.01 | 1.89 | 0.69 | 0.30 | 0.00 |
| SEQ ID NO: 12 | 0.72 | 3.74 | 0.78 | 0.55 | 0.71 | 0.23 |
| SEQ ID NO: 13 | 1.98 | 4.99 | 2.99 | 1.09 | 0.63 | 0.66 |
| SEQ ID NO: 14 | 1.81 | 3.16 | 2.89 | 0.69 | 1.10 | 0.16 |
| SEQ ID NO: 15 | 0.87 | 1.18 | 0.95 | 1.01 | 0.64 | 0.09 |
| SEQ ID NO: 16 | 1.43 | 3.29 | 2.80 | 0.35 | 0.10 | 1.48 |
| SEQ ID NO: 17 | 1.24 | 2.58 | 1.95 | 0.70 | 0.15 | 0.30 |
| SEQ ID NO: 18 | 1.08 | 2.86 | 1.23 | 0.37 | 0.95 | 0.64 |
| SEQ ID NO: 19 | 1.58 | 3.87 | 2.28 | 0.49 | 0.71 | 1.10 |
| SEQ ID NO: 20 | 2.58 | 2.46 | 1.71 | 0.47 | 0.09 | 0.31 |
| SEQ ID NO: 21 | 1.96 | 2.40 | 2.87 | 0.56 | 0.47 | 0.01 |
| SEQ ID NO: 22 | 0.59 | 3.60 | 2.49 | 0.51 | 0.14 | 36.64 |
| SEQ ID NO: 23 | 2.46 | 7.04 | 5.12 | 0.40 | 0.40 | 0.19 |

TABLE 10-continued

Table 10: RCMD samples

|  | RCMD #1 | RCMD #2 | RCMD #3 | RCMD #4 | RCMD #4 | RCMD #5 |
|---|---|---|---|---|---|---|
| SEQ ID NO: 24 | 0.81 | 1.60 | 1.37 | 0.67 | 0.93 | 0.35 |

Table 10: RCMD samples

TABLE 11

|  | RAEB #1 | RAEB #2 | RAEB #3 |
|---|---|---|---|
| SEQ ID NO: 1 | 1.49 | 0.43 | 2.88 |
| SEQ ID NO: 2 | 38.96 | 13.21 | 4.48 |
| SEQ ID NO: 3 | 5.40 | 10.87 | 0.14 |
| SEQ ID NO: 4 | 3.18 | 0.99 | 8.75 |
| SEQ ID NO: 5 | 4.59 | 7.56 | 10.04 |
| SEQ ID NO: 6 | 10.31 | 5.53 | 0.05 |
| SEQ ID NO: 7 | 0.85 | 2.13 | 0.99 |
| SEQ ID NO: 8 | 0.76 | 1.15 | 0.44 |
| SEQ ID NO: 9 | 0.50 | 1.05 | 0.07 |
| SEQ ID NO: 10 | 2.30 | 0.49 | 4.41 |
| SEQ ID NO: 11 | 1.76 | 1.19 | 1.46 |
| SEQ ID NO: 12 | 1.48 | 2.74 | 1.54 |
| SEQ ID NO: 13 | 1.59 | 1.14 | 4.22 |
| SEQ ID NO: 14 | 0.63 | 1.47 | 1.40 |
| SEQ ID NO: 15 | 0.72 | 1.37 | 0.00 |
| SEQ ID NO: 16 | 10.76 | 5.31 | 2.58 |
| SEQ ID NO: 17 | 3.23 | 2.85 | 2.30 |
| SEQ ID NO: 18 | 3.31 | 4.99 | 4.78 |
| SEQ ID NO: 19 | 1.96 | 3.95 | 8.77 |
| SEQ ID NO: 20 | 2.18 | 11.93 | 1.81 |
| SEQ ID NO: 21 | 3.32 | 3.76 | 0.15 |
| SEQ ID NO: 22 | 3.83 | 12.98 | 0.25 |
| SEQ ID NO: 23 | 8.91 | 2.80 | 53.30 |
| SEQ ID NO: 24 | 1.58 | 0.63 | 0.40 |

Table 11: RAEB samples

All the tested samples satisfy the criterions defined in the method according to the invention.

Example 5

Schematic Representation of RARS, RCMD, RAEB and AML Specific Profiles

The results corresponding to the above classification can be illustrated by an "antioxidogram", corresponding to areas representatives of a determined sample.

The expression of each gene of SEQ ID NO: 1-24 is measured by qRT-PCR as defined above, and compared to the expression level of an housekeeping gene GAPDH.

Figure 1:
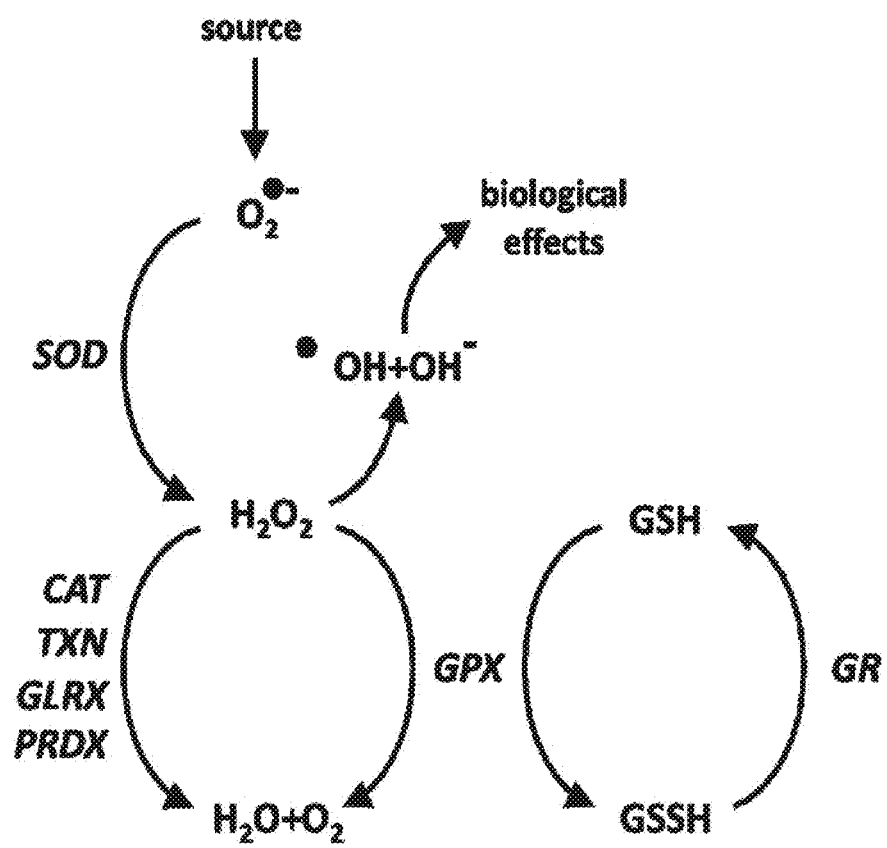
Figure 2:
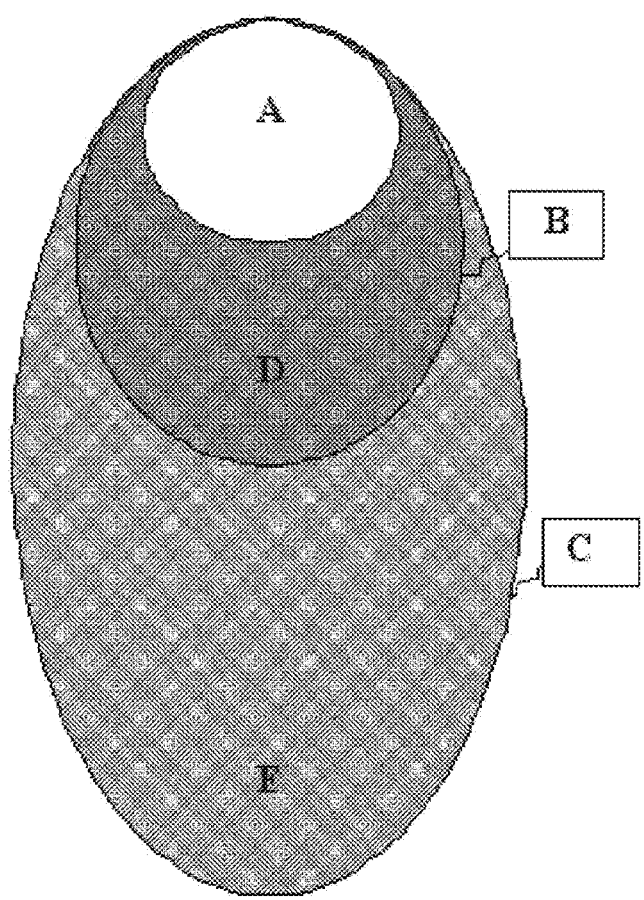
Figure 3A:
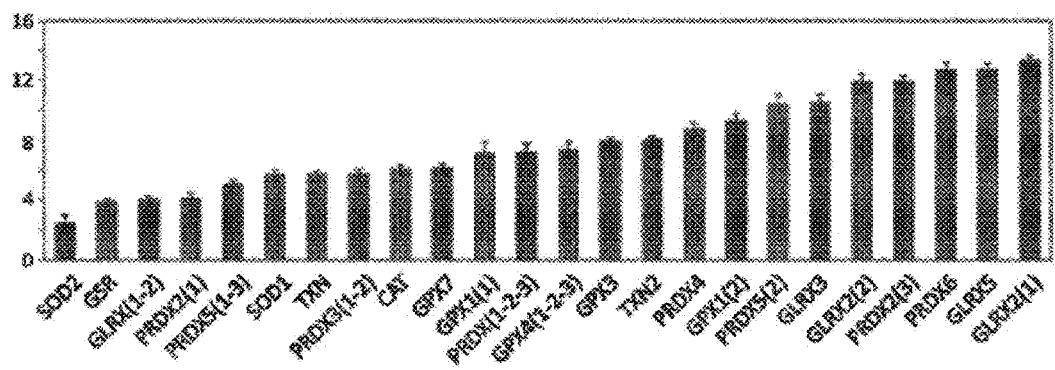
FIG. 3B is a graphic representation of the mean (black line) and standard error of the mean (grey area) of the variation of expression of each indicated genes (x-axis) in a RARS samples compared to control samples (healthy bone marrow samples). Y-axis represents the variation of the amount compared to control samples, expressed in $\log_{10}$.
FIG. 3C is a graphic representation of the mean (black line) and standard error of the mean (grey area) of the variation of expression of each indicated genes (x-axis) in RCMD samples compared to control samples (healthy bone marrow samples). Y-axis represents the variation of the amount compared to control samples, expressed in $\log_{10}$.
FIG. 3D is a graphic representation of the mean (black line) and standard error of the mean (grey area) of the variation of expression of each indicated genes (x-axis) in RAEB samples compared to control samples (healthy bone marrow samples). Y-axis represents the variation of the amount compared to control samples, expressed in $\log_{10}$.
FIG. 3E is a graphic representation of the mean (black line) and standard error of the mean (grey area) of the variation of expression of each indicated genes (x-axis) in AML samples compared to control samples (healthy bone marrow samples). Y-axis represents the variation of the amount compared to control samples, expressed in $\log_{10}$.

FIG. 3A represents the variation of expression of each genes of SEQ ID NO: 1-24 compared to GAPDH, classified according to their expression lever. The gene number is easily found by using the above Table 1.

Figure 3B:
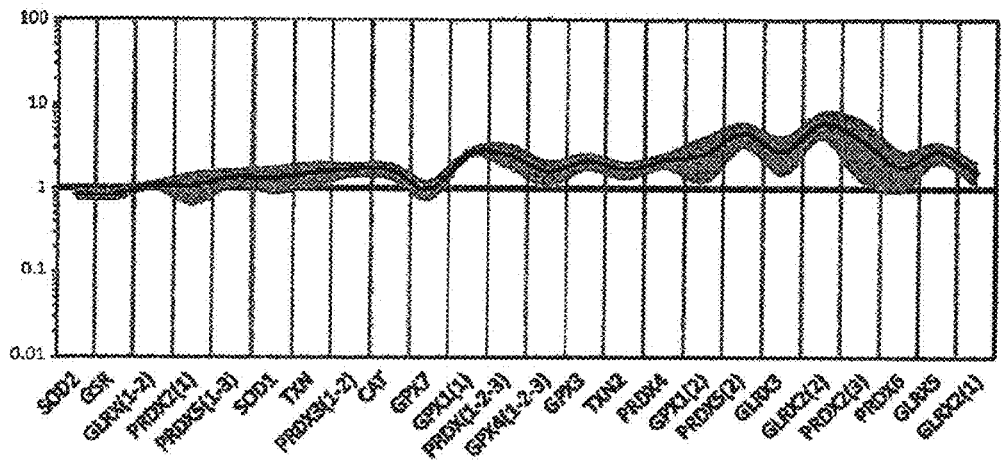
Figure 3C:
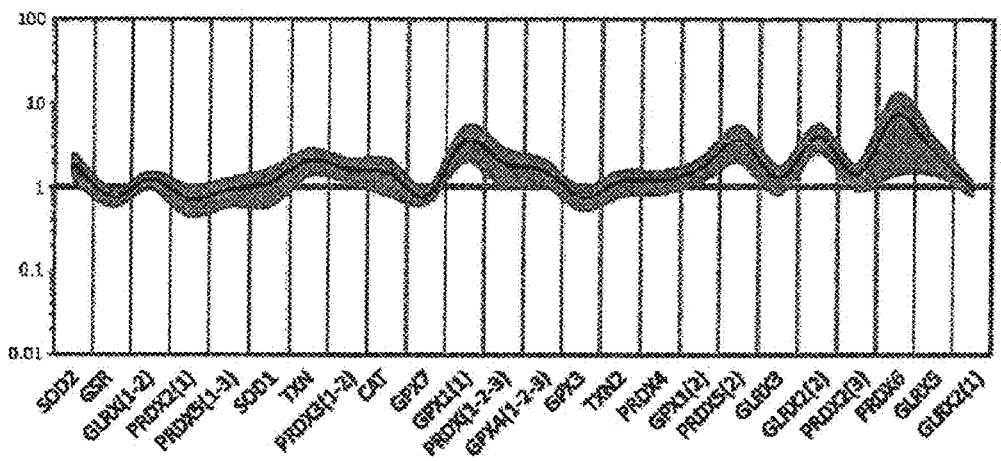
Figure 3D:
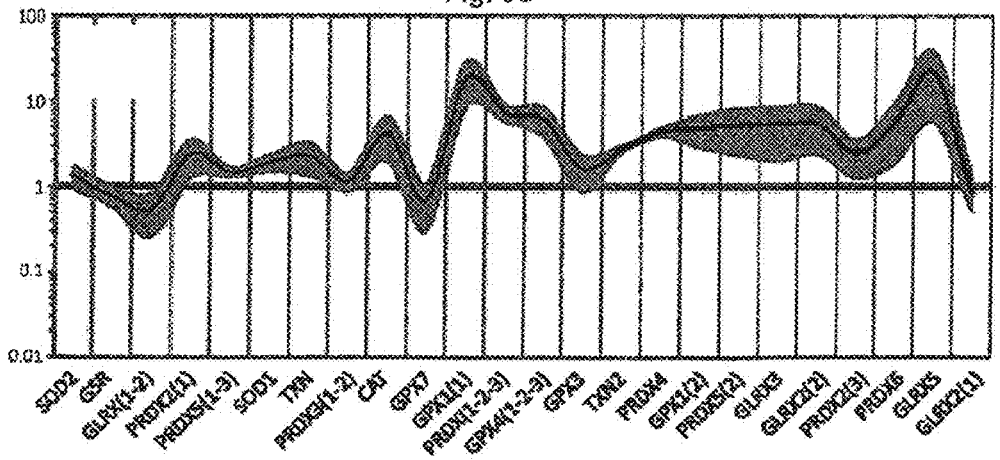
Figure 3E:
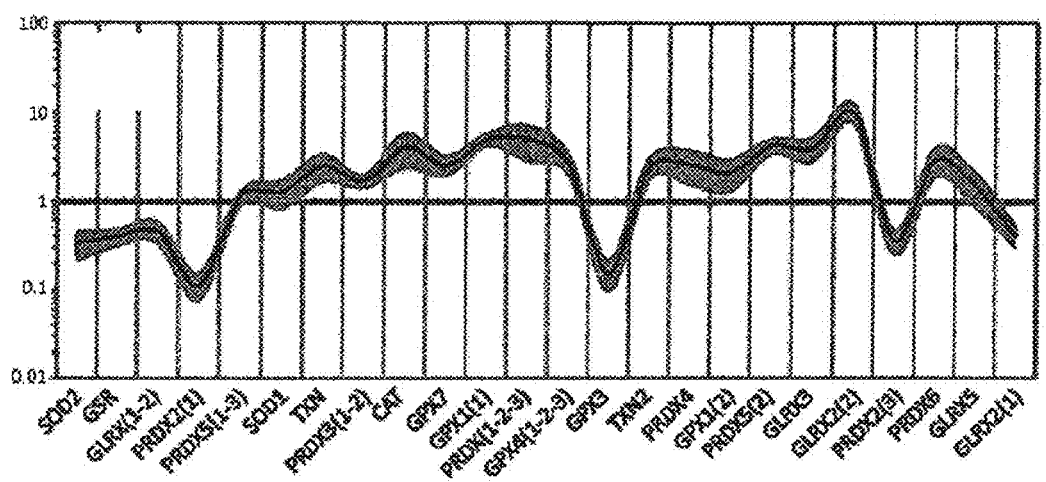

The antioxidogram for RARS sample (FIG. 3B), RCMD sample (FIG. 3C), RAEB samples (FIG. 3D) and AML samples (3E) can be used to classify a new sample.

Indeed, by measuring the ratio for each genes represented by SEQ ID NO: 1-24, a curve can be drawn. This curve can then be compared to the antioxidograms, and thus, it is easy to determine into what type of pathology belongs the studied sample.

Example 6

Classification of Unclassifiable Myelodysplastic Syndromes

The above antioxidogram can be used to classify myelodysplastic syndromes for which other classification techniques fails.

The expression level of each of the genes of SEQ ID NO: 1-24 has been measured according to the invention, and an curve has been established.

This curve (hashed line) has been then compared to the "specific" antioxidogram of RARS, RCDM, RAEB and AML.

FIG. 4 shows that most of the ratios $R_i$ of expression are close to those that are characteristic of an RCDM sample.

FIG. 5 shows that two independent samples of unclassifiable myelodysplastic syndrome presents similar expression level of the genes of SEQ ID NO: 1-24, and thus are close to those that are characteristic of an RCDM sample.

Example 7

Distinction of MDS by Using the Oxydograms

Chronic myelomonocytic leukemia (CMML) is a form of leukemia featuring monocytosis. The categorization of this disease has been controversial.

Patients with CMML can present with various clinical features, mimicking either myelodysplastic syndroms or myeloproliferative neoplasms depending upon a patient's specific presentation.

Due to this controversy it was classified by the World Health Organization in a "myelodysplastic/myeloproliferative" category of medical conditions in the early 2000s.

The oxydogram according to the invention can be helpful to determine the status of a CMML sample, which is close to RAEB by histological analysis.

As shown in FIG. 6, the expression level of the genes SEQ ID NO: 1-24 of samples of two patients with CMML is different from the expression level of the genes SEQ ID NO: 1-24 of RAEB.

These data demonstrate that CMML are distinct from SDM.

Example 8

Use of Oxydogram for the Follow-Up of Evolutive MDS

As mentioned previously, MDS evolve progressively toward AML. It is thus important to know if this progression is slow or rapid.

The oxydogram can be used to determine if the molecular expression of the genes SEQ ID NO: 1-24 has evolved from diagnosis to a determined date.

An example is shown in FIG. 7. A patient has been diagnosed at t=0, as having a RCMD.

Twelve months from the diagnosis, the expression level of the genes SEQ ID NO: 1-24 have also been measured.

The FIG. 7 shows a difference between the expression at the diagnosis and after twelve months. After twelve months, the oxydogram shows that the patient is becoming to evolved from RCMD toward RAEB, although the histological analysis does not any differences.

Example 9

In Vitro Measure of Antitumoral Effect of Demethylating Agent

New therapeutic agents are actively searched in order to treat AML. These compounds are expensive, due to extensive searches, and unfortunately are not universally effective in all AML samples.

An average of 30% of AML subtypes are responsive to the new therapeutic drugs, and could effectively be used in the patient, in order to slow down the leukemic progression.

However, positive or negative in vivo response to a drug cannot be obtained before 6 to 9 months after the beginning of the treatment.

The oxydogram according to the invention can be used to evaluate, in vitro, if the drug will be effective on the leukemic sample, by studying the modulation of the expression level of the genes SEQ ID NO: 1-24.

FIG. 8 show an example of an AML sample treated with the demethylating agent azacytidine. This figure demonstrates that, in this specific sample, treatment modify the expression level of the genes, and could be efficient in vivo for the patient.

The invention claimed is:

1. A method for the diagnosis in vitro, of an acute myeloid leukemia or a myelodysplastic disorder selected from the group consisting of refractory anemia with ringed sideroblasts (RARS), refractory cytopenia with multilineage dysplasia (RCMD), and refractory anemia with excess blasts (RAEB), said method comprising the steps of:
   a) obtaining a bone marrow sample from a human subject,
   b) extracting nucleic acid from said bone marrow sample,
   c) detecting the expression level of 6 genes in said nucleic acid, wherein said 6 genes consist of the nucleotide sequences of SEQ ID NOs: 1 to 6, and wherein said detecting is carried out by contacting said nucleic acid with SEQ ID NOs: 25 to 36,
   d) comparing the expression level of each of said 6 genes with the expression level of said 6 genes in control samples obtained from healthy bone marrow to establish a gene expression level ratio for each gene of said 6 genes,
   e) determining that the ratio established in step d) for at least 3 genes from said 6 genes is either ≥2 or ≤0.5, and
   f) diagnosing said human subject as having an acute myeloid leukemia or a myelodysplastic disorder selected from the group consisting of RARS, RCMD, and RAEB.

2. The method according to claim 1, wherein if the ratio established in step d) is
- ≤0.3, for the gene consisting of the nucleic acid sequence SEQ ID NO: 1, and
- ≥3.0, for the genes consisting of the nucleic acid sequences SEQ ID NO: 2 and 3,
- then said bone marrow sample is representative of an acute myeloid leukemia.

3. The method according to claim 2, wherein the expression level of the genes is measured by quantitative method, selected from the group consisting of RT-qPCR, northern-blotting, microarray and SAGE.

4. The method according to claim 1, wherein if the ratio established in step d) is
- >0.3, for the gene consisting of the nucleic acid sequence of SEQ ID NO: 1, or
- <3, for the genes consisting of the nucleic acid sequences of SEQ ID NOs: 2 or 3,
- then said bone marrow sample is representative of a myelodysplastic disorder selected from the group consisting of RARS, RCMD, and RAEB.

5. The method according to claim 4, wherein the expression level of the genes is measured by quantitative method, selected from the group consisting of RT-qPCR, northern-blotting, microarray and SAGE.

6. The method according to claim 1, wherein the expression level of the genes is measured by quantitative method.

7. The method according to claim 1, wherein the expression level of the genes is measured by quantitative method, selected from the group consisting of RT-qPCR, northern-blotting, microarray and SAGE.

* * * * *